United States Patent
Kirkland et al.

(10) Patent No.: US 10,139,400 B2
(45) Date of Patent: *Nov. 27, 2018

(54) CARBOXY X RHODAMINE ANALOGS

(71) Applicant: PROMEGA CORPORATION, Madison, WI (US)

(72) Inventors: Thomas A. Kirkland, Atascadero, CA (US); Mark G. McDougall, Arroyo Grande, CA (US); Stephen J. Dwight, Arroyo Grande, CA (US)

(73) Assignee: Promega Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/724,111

(22) Filed: May 28, 2015

(65) Prior Publication Data

US 2015/0260725 A1    Sep. 17, 2015

Related U.S. Application Data

(63) Continuation of application No. 13/682,589, filed on Nov. 20, 2012, now Pat. No. 9,056,885.

(60) Provisional application No. 61/562,021, filed on Nov. 21, 2011.

(51) Int. Cl.

| | |
|---|---|
| *G01N 33/542* | (2006.01) |
| *C07D 491/147* | (2006.01) |
| *C07D 223/16* | (2006.01) |
| *C07D 491/16* | (2006.01) |
| *C07D 491/22* | (2006.01) |
| *C09B 11/24* | (2006.01) |
| *C07F 9/6558* | (2006.01) |
| *C07D 471/06* | (2006.01) |
| *C07H 19/073* | (2006.01) |
| *C07H 19/10* | (2006.01) |
| *C12Q 1/686* | (2018.01) |
| *G01N 33/58* | (2006.01) |
| *G01N 33/68* | (2006.01) |

(52) U.S. Cl.
CPC ......... *G01N 33/542* (2013.01); *C07D 223/16* (2013.01); *C07D 471/06* (2013.01); *C07D 491/147* (2013.01); *C07D 491/16* (2013.01); *C07D 491/22* (2013.01); *C07F 9/65586* (2013.01); *C07H 19/073* (2013.01); *C07H 19/10* (2013.01); *C09B 11/24* (2013.01); *C12Q 1/686* (2013.01); *G01N 33/582* (2013.01); *G01N 33/6845* (2013.01); *G01N 2333/90241* (2013.01)

(58) Field of Classification Search
None
See application file for complete search history.

(56) References Cited

U.S. PATENT DOCUMENTS

| | | | |
|---|---|---|---|
| 4,900,686 A | 2/1990 | Amost et al. | |
| 4,997,928 A | 3/1991 | Hobbs, Jr. | |
| 5,171,534 A | 12/1992 | Smith et al. | |
| 5,304,644 A | 4/1994 | Husa et al. | |
| 5,332,666 A | 7/1994 | Prober et al. | |
| 5,863,753 A | 1/1999 | Haugland et al. | |
| 6,080,852 A | 6/2000 | Lee et al. | |
| 7,018,431 B2 | 3/2006 | Menchen et al. | |
| 7,667,024 B2 | 2/2010 | Mao et al. | |
| 7,867,726 B2 | 1/2011 | Wood et al. | |
| 8,669,103 B2 | 3/2014 | Binkowski et al. | |
| 9,056,885 B2 * | 6/2015 | Kirkland | C07D 471/06 |
| 2001/0007905 A1 | 7/2001 | Lam et al. | |
| 2001/0011139 A1 | 8/2001 | Benson et al. | |
| 2004/0198717 A1 | 10/2004 | Coleman et al. | |
| 2009/0263843 A1 | 10/2009 | Anderson et al. | |
| 2010/0173384 A1 | 7/2010 | Johnsson et al. | |
| 2010/0281552 A1 | 11/2010 | Encell et al. | |
| 2011/0130384 A1 | 6/2011 | Setoh et al. | |
| 2012/0237961 A1 | 9/2012 | Gautier et al. | |
| 2013/0317207 A1 | 11/2013 | Kirkland | |

FOREIGN PATENT DOCUMENTS

| | | |
|---|---|---|
| EP | 1475368 | 11/2004 |
| EP | 2298731 | 3/2011 |
| GB | 926816 | 5/1963 |
| JP | H1-503488 | 11/1989 |
| JP | 2003-501539 | 1/2003 |
| JP | 2004-107331 | 4/2004 |
| JP | 2005-509629 | 4/2005 |
| WO | 88/07682 | 10/1988 |
| WO | WO 94/05688 | 3/1994 |

(Continued)

OTHER PUBLICATIONS

"Antibody structure" http://www.biology.arizona.edu/immunology/tutorials/antibody/structure.html, accessed Sep. 8, 2016.*
Adams et al., "Davidson's the Biochemistry of the Nucleic Acids," Eighth Edition, Academic Press, 1976 (2 pages).
Beija et al., "Synthesis and applications of Rhodamine derivatives as fluorescent probes," Chem. Soc. Rev., 2009, 38, 2410-2433.
Benink et al., "autofluoDirect pH measurements by using subcellular targeting of 5(and 6-) carboxyseminaphthorhodafluor in mammalian cells," Sep. 2009, BioTechniques 47:769-774.
Chemical Abstracts Service, Columbus, Ohio, US; Feb. 9, 2011, XP002590844.
Chemical Abstracts Service, Columbus, Ohio, US; Valderrama, Jaime A. et al: "Studies on quinones. Part 22. Synthesis of 1-benzazepine-6,9-quinone derivatives" XP002690843, retrieved from STN Database accession No. 1992:194129.

(Continued)

Primary Examiner — Noble E Jarrell
(74) Attorney, Agent, or Firm — Michael Best & Friedrich LLP

(57) ABSTRACT

The present invention provides novel fluorescent dyes and kits containing the same, which are useful for labeling a wide variety of biomolecules, cells and microorganisms. The present invention also provides various methods of using the fluorescent dyes for research and development, forensic identification, environmental studies, diagnosis, prognosis and/or treatment of disease conditions.

19 Claims, 38 Drawing Sheets

(56) References Cited

FOREIGN PATENT DOCUMENTS

| WO | WO 00/07992 | 2/2000 | | |
|---|---|---|---|---|
| WO | WO 08/58486 | 10/2000 | | |
| WO | WO 00/75236 | 12/2000 | | |
| WO | WO 034987 | 5/2003 | | |
| WO | 2009/157196 | 12/2009 | | |
| WO | WO 2013/078244 | 5/2013 | | |
| WO | 2014093671 | * | 6/2014 | ............ A61K 39/00 |

OTHER PUBLICATIONS

Fieser, "Reagents for Organic Synthesis," vol. Seven, John Wiley & Sons, Inc., 1994, (4 pages).

Greene and Wuts, "Protective Groups in Organic Synthesis," Third Edition, 1999 John Wiley & Sons, Inc., (52 pages).

Huffman et al., "Lithium Alkoxides of Cinchona Alkaloids as Chiral Controllers for Enantioselective Acetylide Addition to Cyclic N-Acyl Ketimines," J. Org. Chem. 1995, 60, 1590-1594.

Larock, "Comprehensive Organic Transformations. A Guide to Functional Group Preparations," Second Edition, Wiley-VCH, 22 pages, 1999.

Malik, Farnaz et al: "Syntheses and CD studies of new optically active substituted 1,5-benzodiazepine derivatives" Liebigs Annalen, (1), 127-34 CODEN: Lanaem; ISSN: 0947-3440, 1996.

Ohno M et al: "Development of 3,4-dihydro-2H-benzo[1,4]oxazine derivatives as dual thromboxane A2 receptor antagonists and prostacyclin receptor agonists" Bioorganic & Medicinal Chemistry, Pergamon, GB, vol. 14, No. 6, Mar. 15, 2006, pp. 2005-2021.

Paquette, "Encyclopedia of Reagents for Organic Synthesis," John Wiley & Sons, 1995, (18 pages).

Saha et al., "Influence of the Structure of the Amino Group and Polarity of the Medium on the Photophysical Behavior of 4-Amino-1,8-naphthalimide Derivatives," J. Phys. Chem. A 2002, 106, 4763-4771.

Tecle et al., "The Design, Synthesis and Potential Utility of Fluorescence Probes that Target DFG-out Conformation of p38a for High Throughput Screening Binding Assay," Chem Biol Drug Des 2009; 74: 547-559.

Tucker et al., "Synthesis of a Series of 4-(Arylethynyl)-6-chloro-4-cyclopropyl-3,4-dihydroquinazolilHn-)2-(ones as Novel Non-nucleoside HIV-1 Reverse Transcriptase Inhibitors," J. Med. Chem. 1994, 37, 2437-2444.

White et al., "Amino Analogs of Firefly Luciferin and Biological Activity Thereof," Journal of the American Chemical Society, 88:9, May 5, 1966, 2015-2019.

Wittung et al., "DNA-like double helix formed by peptide nucleic acid," Letters to Nature, vol. 368, Apr. 7, 1994, 561-563.

Wu et al., "Synthesis and Spectroscopic Properties of Rosamines with Cyclic Amine Substituents," J. Org. Chem. 2008, 73, 8711-8718.

Xia et al., "Biosensing and imaging based on bioluminescence resonance energy transfer," Current Opinion in Biotechnology 2009, 20:37-44.

Zachariasse et al., "Photoinduced intramolecular charge transfer and internal conversion in molecules all energy gap between S1 and S2. Dynamics and structure," Journal of Photochemistry and Photobiology A: Chemistry 105 (1997) 373-383.

PCT/US2012/066139 International Search Report and Written Opinion dated Feb. 7, 2013 (17 pages).

United States Patent Office Action for U.S. Appl. No. 13/682,589 dated May 15, 2014 (6 pages).

United States Patent Office Action for U.S. Appl. No. 3/682,589 dated Sep. 11, 2014 (8 pages).

United States Patent Office Notice of Allowance for U.S. Appl. No. 13/682,589 dated Jan. 2, 2015 (6 pages).

European Patent Office Action for Application No. 12798535.6 dated Jun. 13, 2016 (4 pages).

Japanese Patent Office Action for Application No. 2014-543546 dated Jul. 7, 2016 (15 pages including translation).

Japanese Patent Office Action for Application No. 2014-543546 dated May 24, 2017 (8 pages including translation).

Glen Research, 5'-TFA-Amino-Modifiers, 2012, 1 page.

United States Patent Office Action for U.S. Appl. No. 15/204,664 dated Mar. 26, 2018 (9 pages).

Japanese Patent Office Action for Application No. 2014-543546 dated May 14, 2018 (28 pages, English translation included).

\* cited by examiner

| Structure | | | | |
|---|---|---|---|---|
| 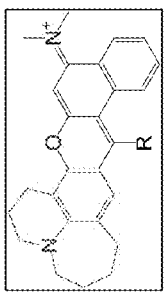 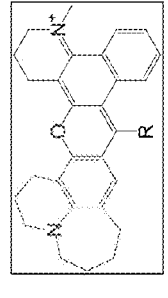 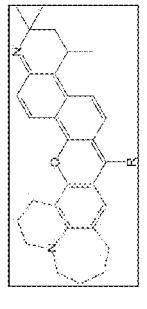 | 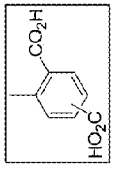 | 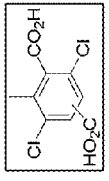 | 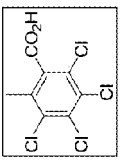 | 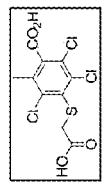 |
| | | 6: PBI 4497<br>6-SE: PBI 4509 | PBI 4464 | 1120-82 |
| | | | PBI 4484 | |
| | | | PBI 4273 | |
FIG. 1D Structure
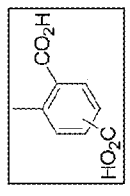
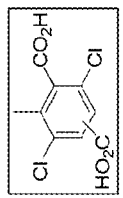
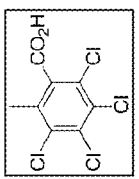
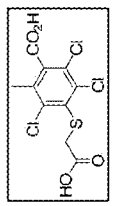
PBI 4302
1178-54a
SE: 1178-61a
O2 HT: PBI 4356
O4 HT: PBI 4357
6: PBI 4351
PBI 4335
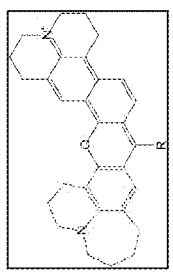
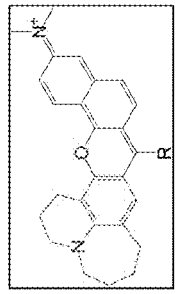
FIG. 1E Structure
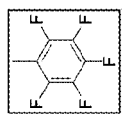
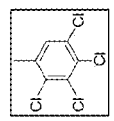
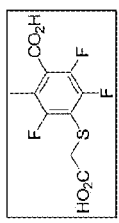
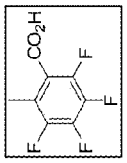
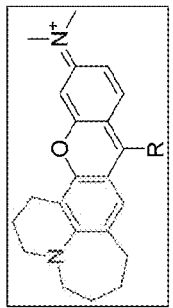
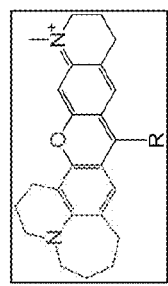
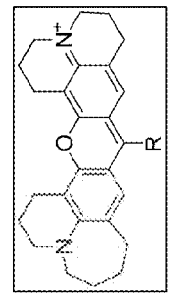
FIG. 2A Structure
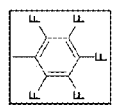
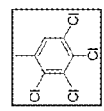
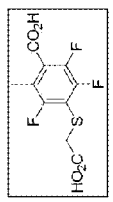
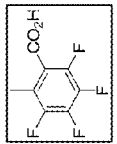
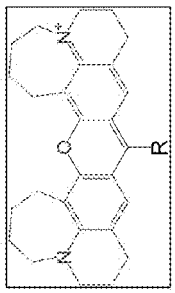
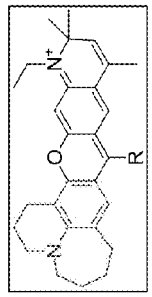
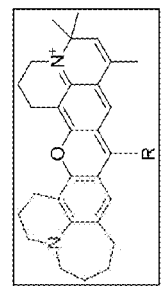
1207-57a
PBI 4568
SE: PBI 4563
FIG. 2C Structure
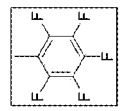
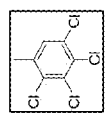
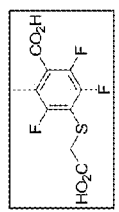
PBI 4559
SE: PBI 4566
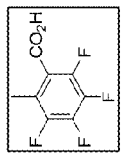
1207-54a
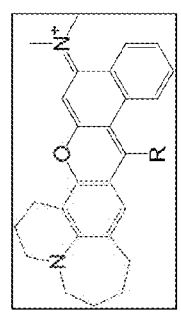
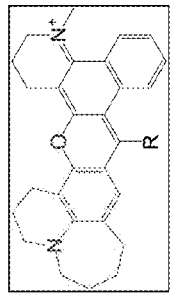
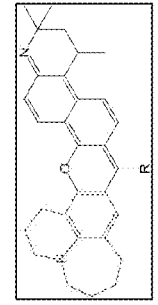
FIG. 2D Structure
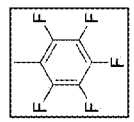
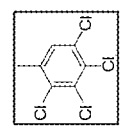
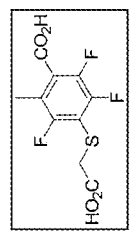
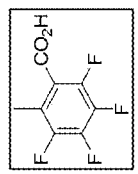
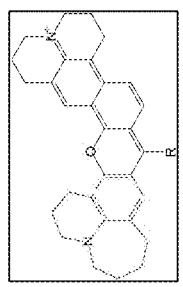
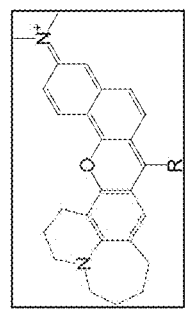
FIG. 2E Structure
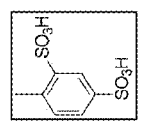
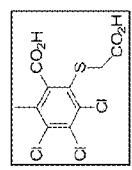
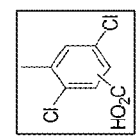
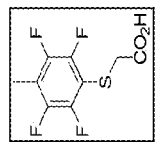
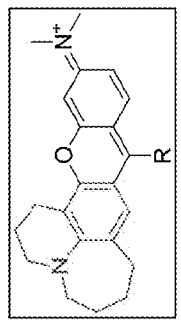
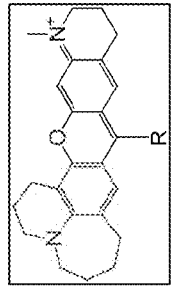
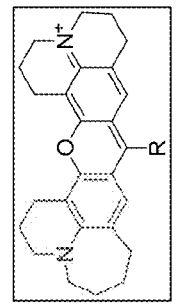
FIG. 3A Structure 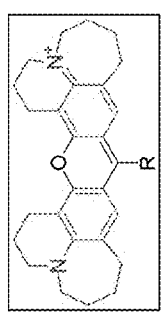 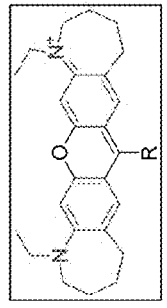 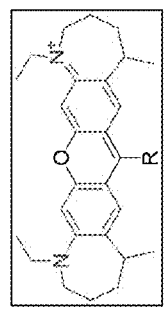
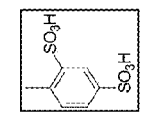 PBI 3904
O2 HT: PBI 3909
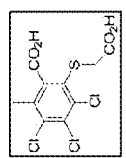 PBI 4124
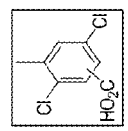
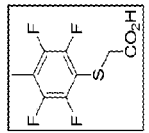 PBI 3865
FIG. 3B

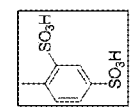
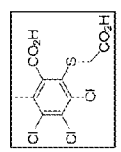
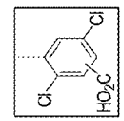
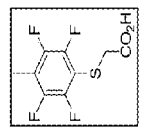
5: PBI 3971
Structure
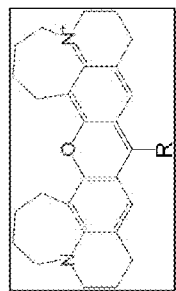
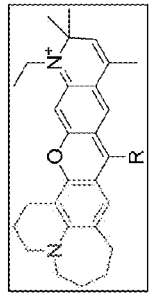
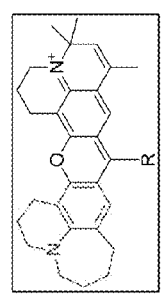
FIG. 3C Structure
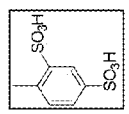
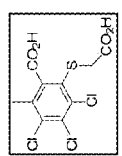
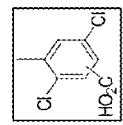
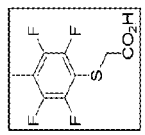
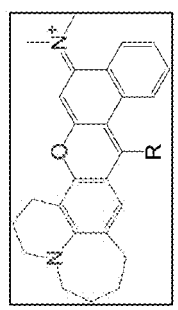 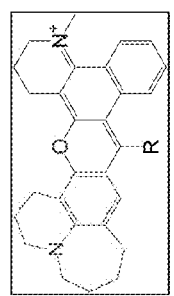 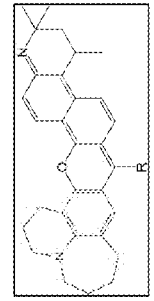
FIG. 3D

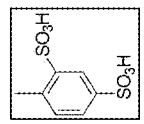
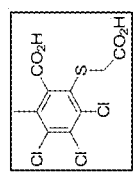
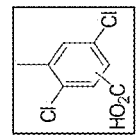
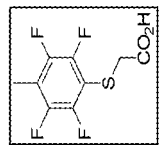
Structure
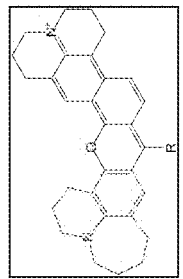
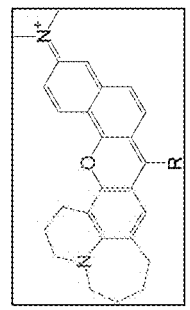
FIG. 3E

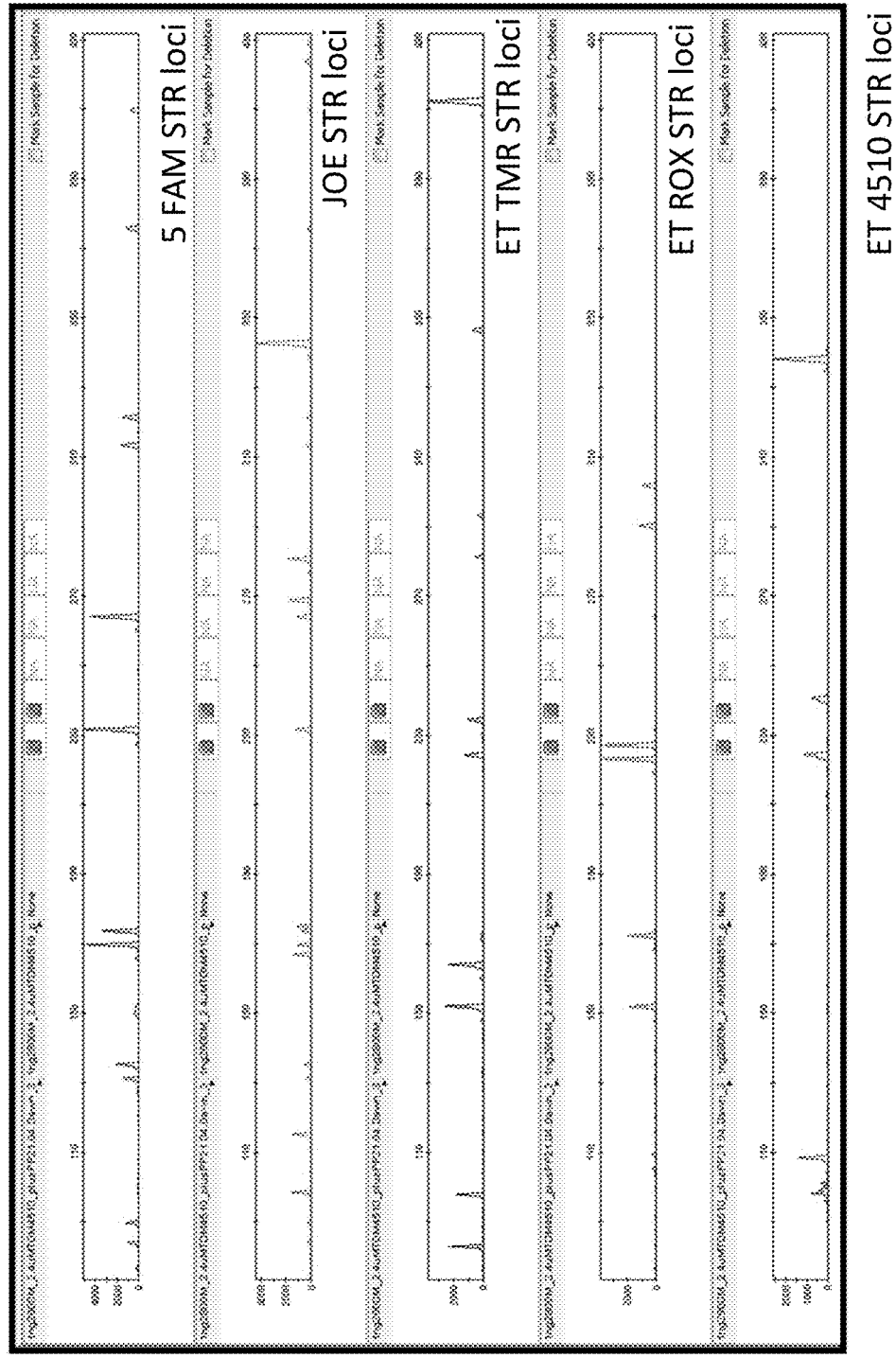
Figure 4: 1ng 2800M DNA

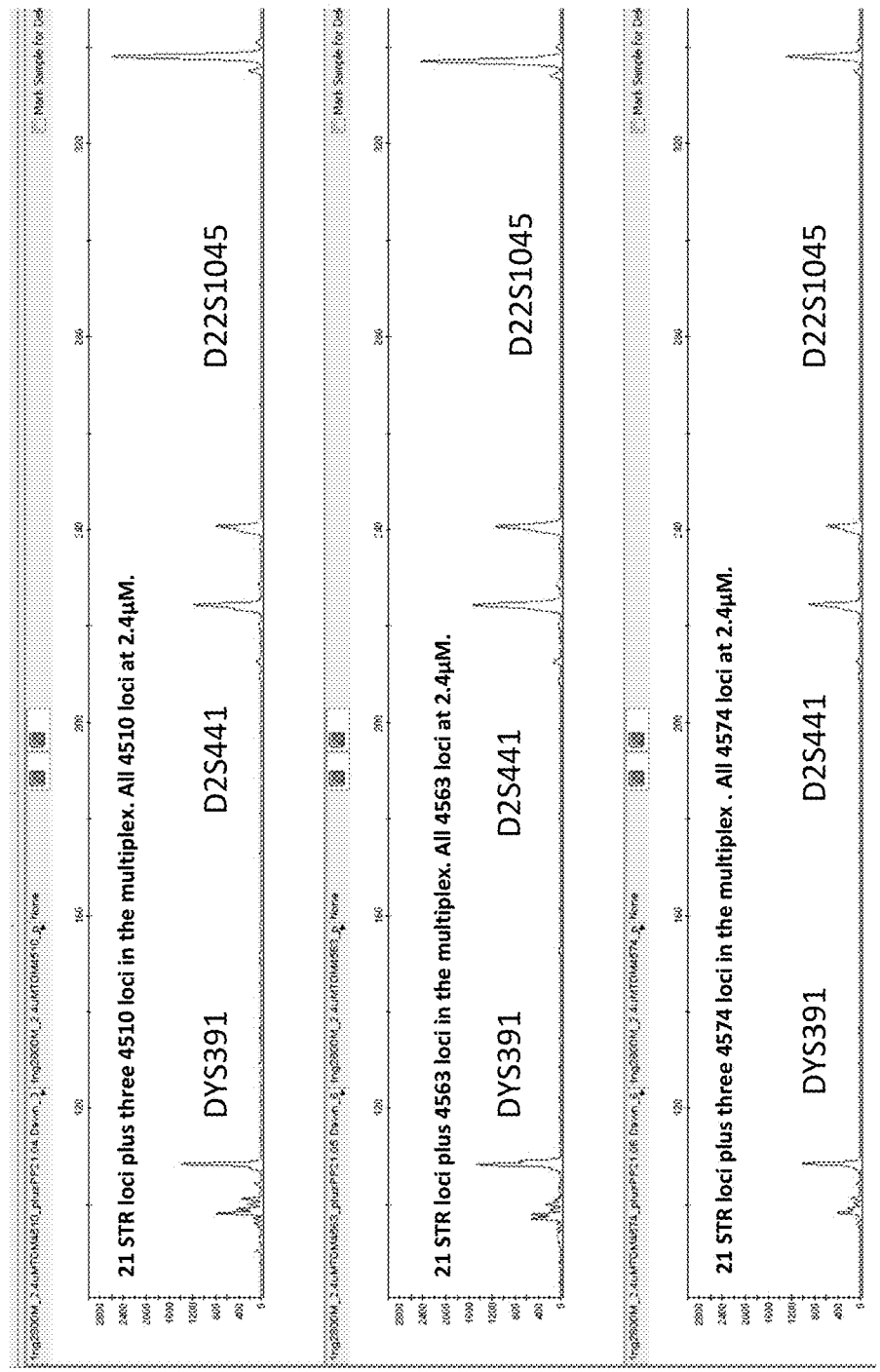

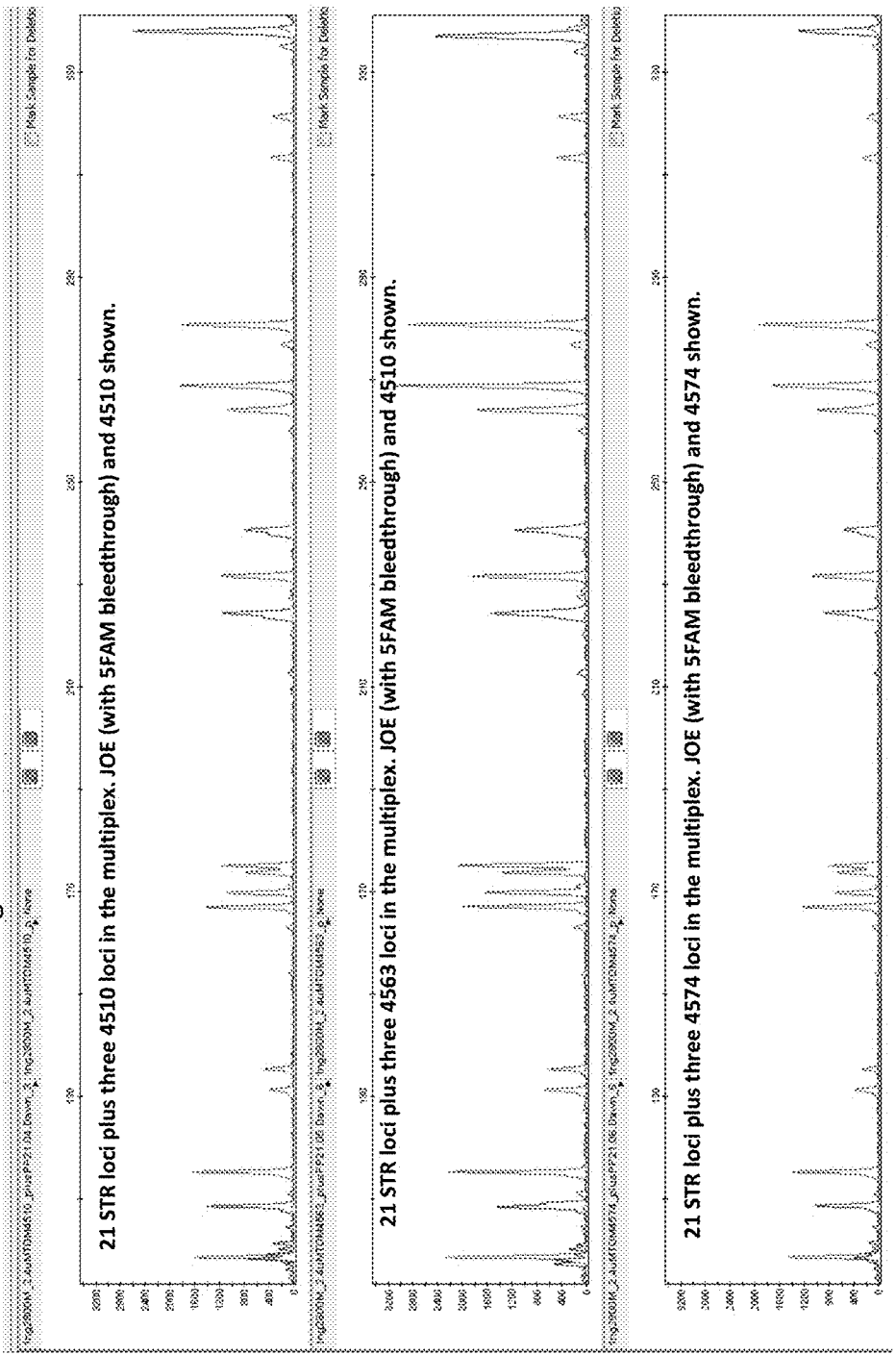

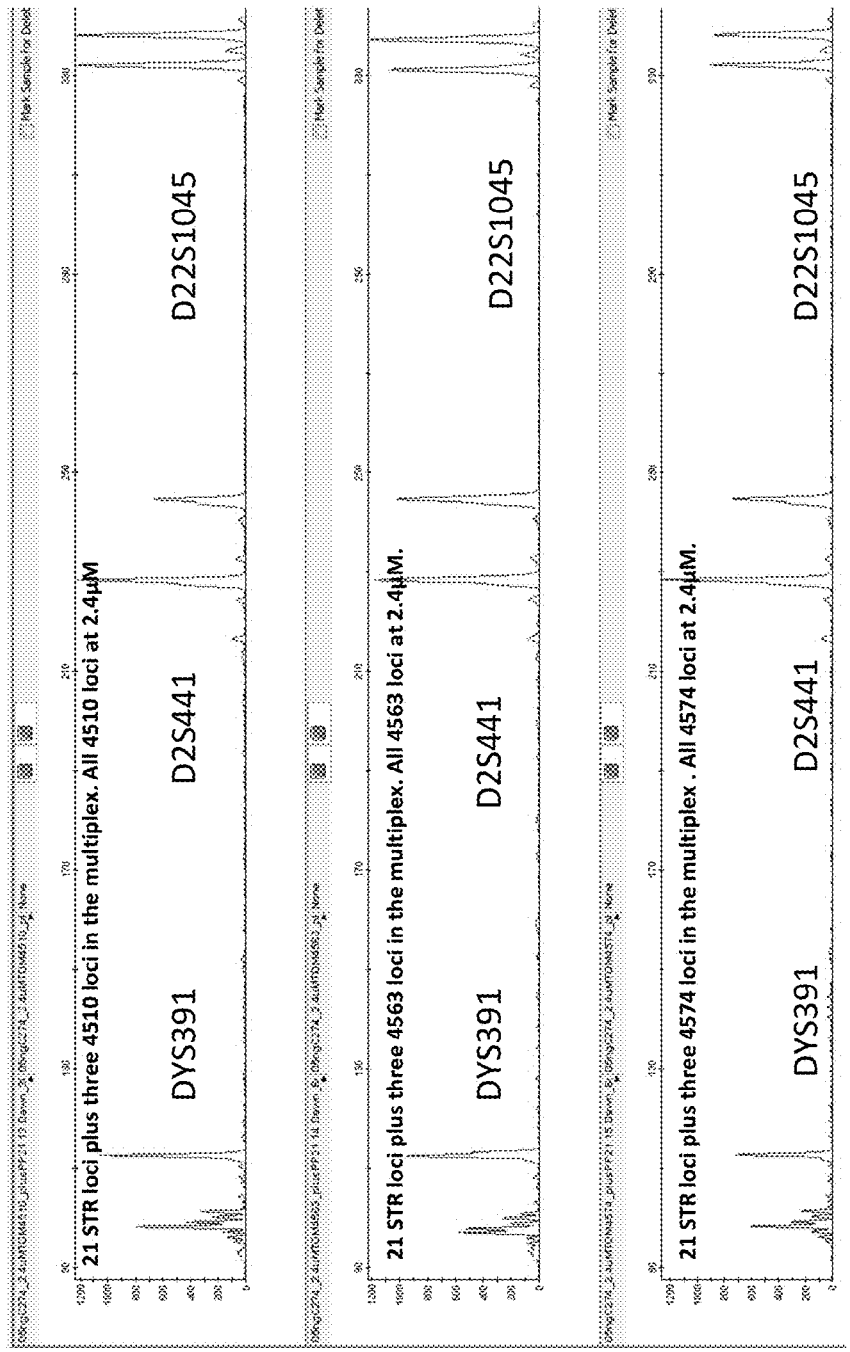
FIG. 7: 0.5ng C274 DNA

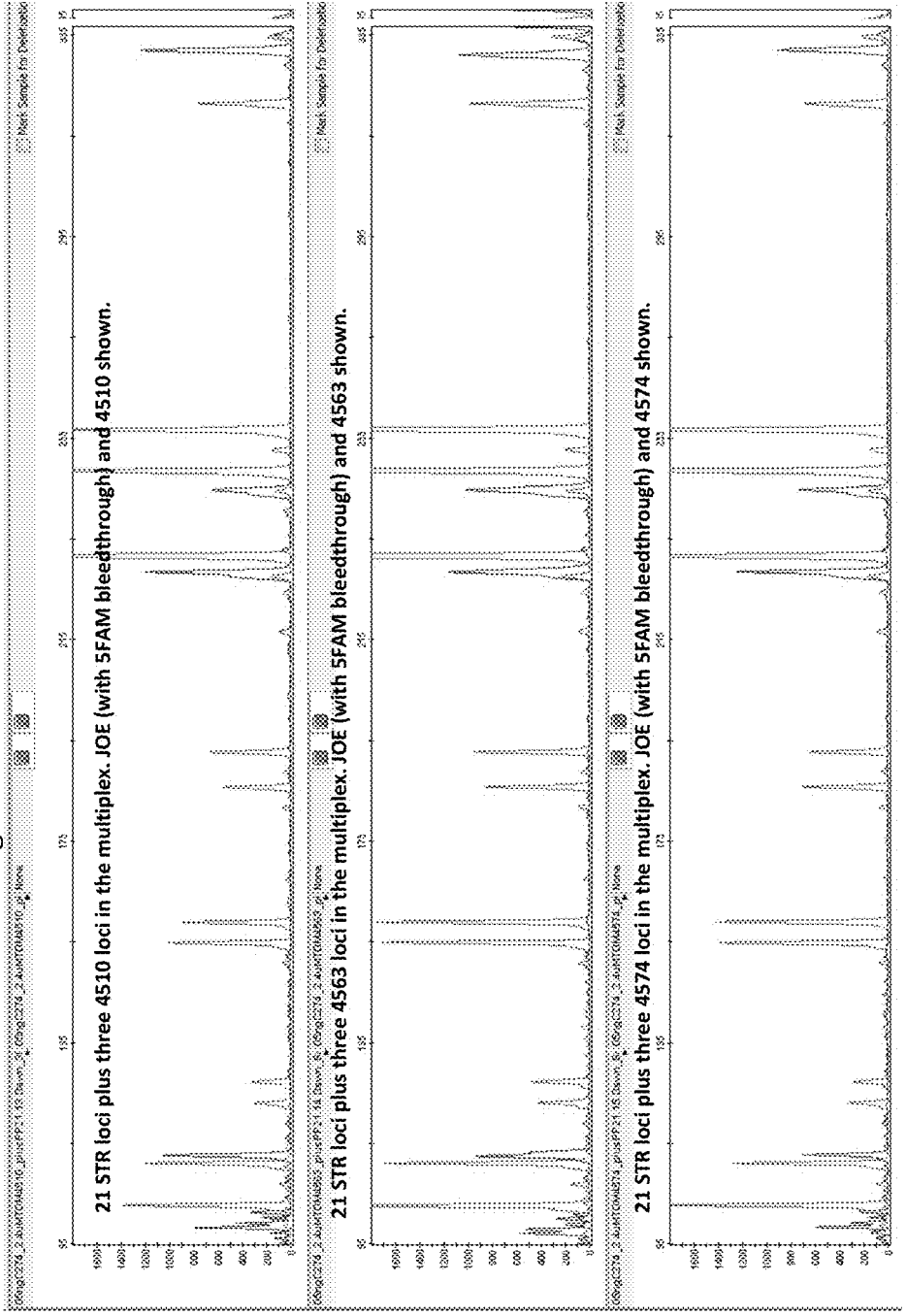

(b)

(a)

CARBOXY X RHODAMINE ANALOGS

CROSS-REFERENCE TO RELATED APPLICATIONS

This application is a continuation of U.S. application Ser. No. 13/682,589, filed Nov. 20, 2012, now U.S. Pat. No. 9,056,885, which claims priority to U.S. Provisional Application No. 61/562,021, filed Nov. 21, 2011, the entire contents of which are hereby incorporated by reference.

FIELD OF THE INVENTION

The invention relates to fluorescent dyes and methods of using them.

BACKGROUND

Fluorescent dyes are widely used in biological research and medical diagnostics. Fluorescent dyes tend to be superior to conventional techniques because they are less expensive, less toxic and can generally be detected with sufficient sensitivity. A diversity of fluorescent dyes with a distinguishable color range has made it more practical to perform multiplexed assays capable of detecting multiple biologic targets at the same time.

Further improvement in the properties of the dyes is needed in order to meet the increasing demands of new instruments and new biological applications. In particular, additional strategies to allow for fine-tuning of the wavelengths of the dyes for maximal signal detection and to provide additional colors are needed.

SUMMARY

In one aspect, the invention provides a compound according to formula (Ia) or (Ib):

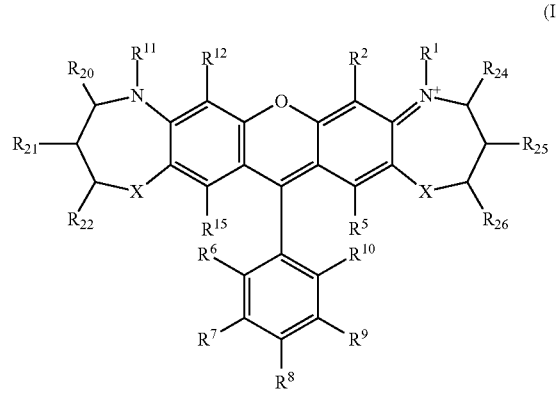
(Ia)

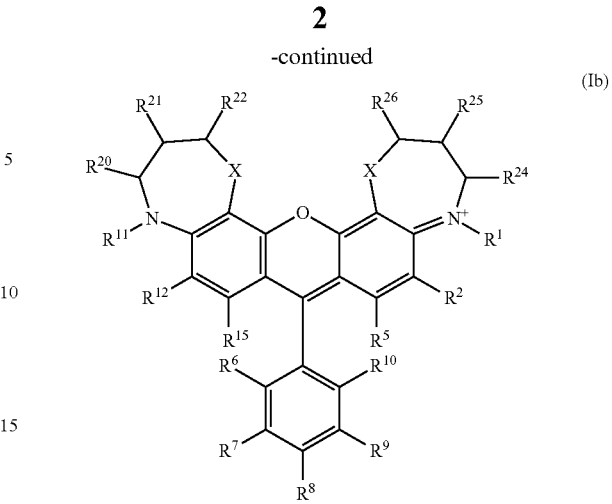
(Ib)

where $R^1$ and $R^{11}$ are independently H or $C_{1-4}$ alkyl, L-R or L-$C_s$;

L is a covalent linkage that is linear or branched, cyclic or heterocyclic saturated or unsaturated, having 1-16 non hydrogen atoms such that the linkage contains any combination of ester, acid, amine, amide, alcohol, ether, thioether or halide groups or single, double, triple or aromatic carbon-carbon bond;

R is a reactive group;

$C_s$ is a conjugated substance;

$R^2$, $R^5$, $R^{12}$ and $R^{15}$ are independently H, alkyl, aryl, heteroaryl, $CO_2H$, $SO_3H$, L-$CO_2H$, L-$SO_3H$, L-R or L-$C_s$;

$R^{20}$, $R^{21}$, $R^{22}$, $R^{23}$, $R^{24}$, $R^{25}$, and $R^{26}$ are independently H or $C_{1-6}$ alkyl or one or more of $R^{20}$ and $R^{21}$, $R^{21}$ and $R^{22}$, $R^{22}$ and $R^{23}$, $R^{24}$ and $R^{25}$, $R^{25}$ and $R^{26}$, and $R^{26}$ and $R^{23}$ together form an aryl, heteroaryl, carbocyclic or heterocyclic ring;

$R^1$ and $R^2$ and/or $R^{11}$ and $R^{12}$ may together form a carbocyclic, heterocyclic, aryl or heteroaryl ring;

$R^{6-10}$ are independently H, halo, OH, alkyl, aryl, heteroaryl, $CO_2H$, $SO_3H$, L-$CO_2H$, L-$SO_3H$, L-R or L-$C_s$;

each X is independently $CHR^{23}$, O, S or $NR^{30}$; and $R^{30}$ is H, $C_{1-4}$ alkyl or —C(O)$C_{1-4}$ alkyl.

In another aspect, the invention provides a compound according to formula (IIa) or (IIb):

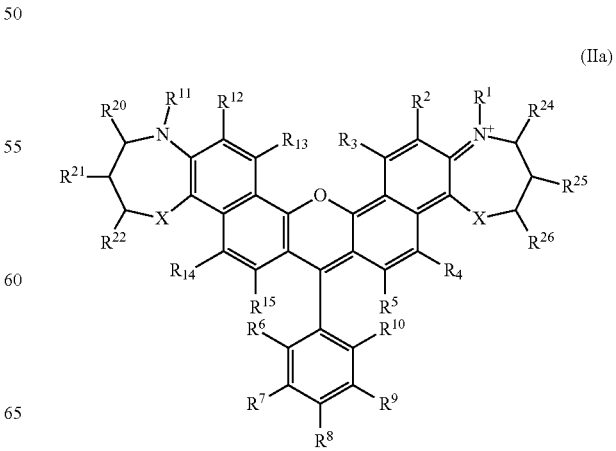
(IIa)

-continued (IIb)

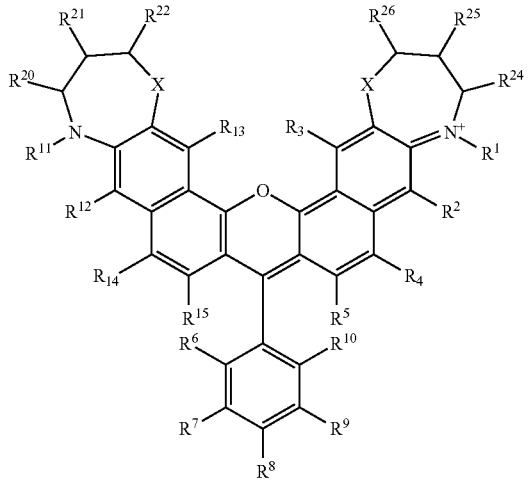

wherein

R¹ and R¹¹ are independently H or $C_{1-4}$ alkyl, L-R or L-$C_s$;

L is a covalent linkage that is linear or branched, cyclic or heterocyclic saturated or unsaturated, having 1-16 non hydrogen atoms such that the linkage contains any combination of ester, acid, amine, amide, alcohol, ether, thioether or halide groups or single, double, triple or aromatic carbon-carbon bond;

R is a reactive group;

$C_s$ is a conjugated substance;

R², R³, R⁴, R⁵, R¹², R¹³, R¹⁴ and R¹⁵ are independently H, alkyl, aryl, heteroaryl, $CO_2H$, $SO_3H$, L-$CO_2H$, L-$SO_3H$, L-R or L-$C_s$;

R²⁰, R²¹, R²², R²³, R²⁴, R²⁵ and R²⁶ are independently H or $C_{1-6}$ alkyl or one or more of R²⁰ and R²¹, R²¹ and R²², R²² and R²³, R²⁴ and R²⁵, R²⁵ and R²⁶, and R²⁶ and R²³ together form an aryl, heteroaryl, carbocyclic or heterocyclic ring;

R¹ and R² and/or R¹¹ and R¹² may together form a carbocyclic, heterocyclic, aryl or heteroaryl ring;

$R^{6-10}$ are independently H, F, Cl, Br, I, OH, alkyl, aryl, heteroaryl, $CO_2H$, $SO_3H$, L-$CO_2H$, L-$SO_3H$, L-R or L-$C_s$;

each X is independently $CHR^{23}$, O, S or $NR^{30}$; and

R³⁰ is H, $C_{1-4}$ alkyl or —$C(O)C_{1-4}$ alkyl.

In a further aspect, the invention provides a compound according to formula (IIIa), (IIIb) or (IIIc):

(IIIa)

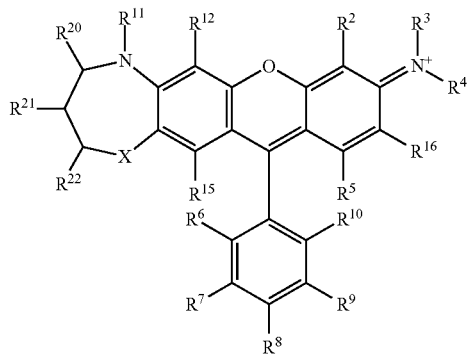

(IIIb)

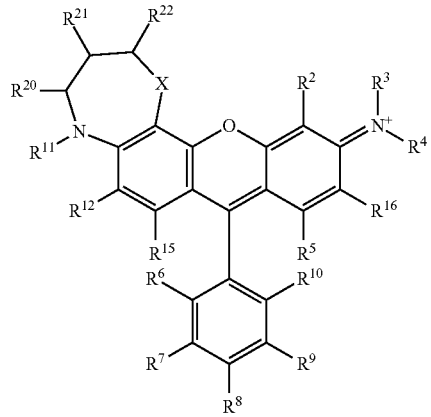

(IIIc)

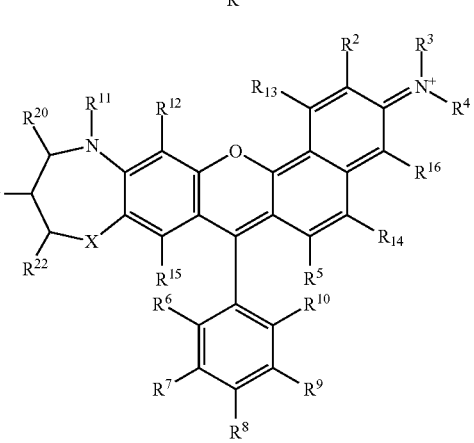

wherein

R¹¹ is independently H or $C_{1-4}$ alkyl, L-R or L-$C_s$;

L is a covalent linkage that is linear or branched, cyclic or heterocyclic saturated or unsaturated, having 1-16 non hydrogen atoms such that the linkage contains any combination of ester, acid, amine, amide, alcohol, ether, thioether or halide groups or single, double, triple or aromatic carbon-carbon bond;

R is a reactive group;

$C_s$ is a conjugated substance;

R² and R¹⁶ can be independently H, alkyl, aryl, heteroaryl, $CO_2H$, $SO_3H$, L-$CO_2H$, L-$SO_3H$, L-R or L-$C_s$;

R³ and R⁴ are H, alkyl, L-R, L-$C_s$, L-$CO_2H$, L-$SO_3H$ or together form a carbocyclic, aryl, heteroaryl, or heterocyclic ring;

alternatively, R² and R³ and independently R⁴ and R¹⁶ together form a carbocyclic, heterocyclic, aryl or heteroaryl ring;

R⁵, R¹², R¹³, R¹⁴ and R¹⁵ are independently H, alkyl, aryl, heteroaryl, $CO_2H$, $SO_3H$, L-$CO_2H$, L-$SO_3H$, L-R or L-$C_s$;

R²⁰, R²¹, R²² and R²³ are independently H or $C_{1-6}$ alkyl or one or more of R²⁰ and R²¹, R²¹ and R²², R²² and R²³, together form an aryl, heteroaryl, carbocyclic or heterocyclic ring;

R¹¹ and R¹² may together form a carbocyclic, heterocyclic, aryl or heteroaryl ring;

$R^{6-10}$ are independently H, F, Cl, Br, I, OH, alkyl, aryl, heteroaryl, $CO_2H$, $SO_3H$, L-$CO_2H$, L-$SO_3H$, L-R or L-$C_s$;

X is $CHR^{23}$, O, S or $NR^{30}$; and

R³⁰ is H, $C_{1-4}$ alkyl or —$C(O)C_{1-4}$ alkyl.

In yet another aspect, the invention provides a compound according to formula (IV):

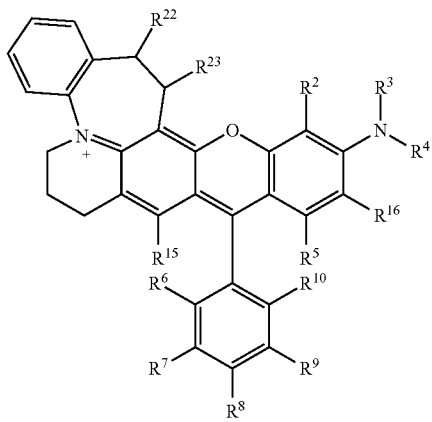

(IV)

wherein $R^2$ and $R^{16}$ can be independently H, alkyl, aryl, heteroaryl, $CO_2H$, $SO_3H$, $L\text{-}CO_2H$, $L\text{-}SO_3H$, L-R or $L\text{-}C_s$;

L is a covalent linkage that is linear or branched, cyclic or heterocyclic saturated or unsaturated, having 1-16 non hydrogen atoms such that the linkage contains any combination of ester, acid, amine, amide, alcohol, ether, thioether or halide groups or single, double, triple or aromatic carbon-carbon bond;

R is a reactive group;

$C_s$ is a conjugated substance;

$R^3$ and $R^4$ are H, alkyl or together form a carbocyclic, aryl, heteroaryl, or heterocyclic ring;

alternatively, $R^2$ and $R^3$ and independently $R^4$ and $R^{16}$ together form a carbocyclic, heterocyclic, aryl or heteroaryl ring;

$R^5$ and $R^{15}$ are independently H, alkyl, aryl, heteroaryl, $CO_2H$, $SO_3H$, $L\text{-}CO_2H$, $L\text{-}SO_3H$, L-R or $L\text{-}C_s$;

$R^{22}$ and $R^{23}$ are independently H or $C_{1-6}$ alkyl or together form an aryl, heteroaryl, carbocyclic or heterocyclic ring; and $R^{6-10}$ are independently H, F, Cl, Br, I, OH, alkyl, aryl, heteroaryl, $CO_2H$, $SO_3H$, $L\text{-}CO_2H$, $L\text{-}SO_3H$, L-R or $L\text{-}C_s$.

In a further aspect, the invention provides a compound according to formula (V):

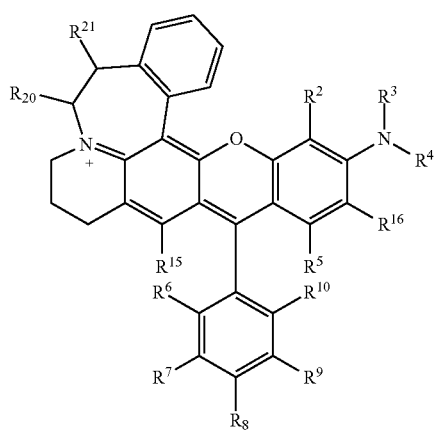

(V)

wherein $R^2$ and $R^{16}$ can be independently H, alkyl, aryl, heteroaryl, $CO_2H$, $SO_3H$, $L\text{-}CO_2H$, $L\text{-}SO_3H$, L-R or $L\text{-}C_s$;

L is a covalent linkage that is linear or branched, cyclic or heterocyclic saturated or unsaturated, having 1-16 non hydrogen atoms such that the linkage contains any combination of ester, acid, amine, amide, alcohol, ether, thioether or halide groups or single, double, triple or aromatic carbon-carbon bond;

R is a reactive group;

$C_s$ is a conjugated substance;

$R^3$ and $R^4$ are H, alkyl, or together form a carbocyclic, heterocyclic, aryl or heteroaryl ring;

alternatively, $R^2$ and $R^3$ and independently $R^4$ and $R^{16}$ may together form a carbocyclic, heterocylic, aryl or heteroaryl ring;

$R^5$ and $R^{15}$ are independently H, alkyl, aryl, heteoaryl, $CO_2H$, $SO_3H$, $L\text{-}CO_2H$, $L\text{-}SO_3H$, L-R or $L\text{-}C_s$;

$R^{20}$ and $R^{21}$ are independently H or $C_{1-6}$ alkyl or together form an aryl, heteroaryl, carbocyclic or heterocyclic ring; and $R^{6-10}$ are independently H, F, Cl, Br, I, OH, alkyl, aryl, heteroaryl, $CO_2H$, $SO_3H$, $L\text{-}CO_2H$, $L\text{-}SO_3H$, L-R or $L\text{-}C_s$.

In another aspect, the invention provides a compound according to formula (VI):

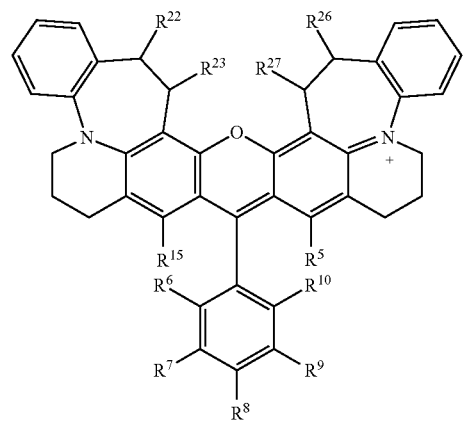

(VI)

wherein $R^5$ and $R^{15}$ are independently H, alkyl, aryl, heteroaryl, $CO_2H$, $SO_3H$, $L\text{-}CO_2H$, $L\text{-}SO_3H$, L-R or $L\text{-}C_s$;

L is a covalent linkage that is linear or branched, cyclic or heterocyclic saturated or unsaturated, having 1-16 non hydrogen atoms such that the linkage contains any combination of ester, acid, amine, amide, alcohol, ether, thioether or halide groups or single, double, triple or aromatic carbon-carbon bond;

R is a reactive group;

$C_s$ is a conjugated substance;

$R^{22}$, $R^{23}$, $R^{26}$ and $R^{27}$ are independently H or $C_{1-6}$ alkyl or one or more of $R^{22}$ and $R^{23}$ and $R^{26}$ and $R^{27}$ together form an aryl, heteroaryl, carbocyclic or heterocyclic ring; and $R^{6-10}$ are independently H, F, Cl, Br, I, OH, alkyl, aryl, heteroaryl, $CO_2H$, $SO_3H$, $L\text{-}CO_2H$, $L\text{-}SO_3H$, L-R or $L\text{-}C_s$.

In an additional aspect, the invention provides a compound according to formula (VII):

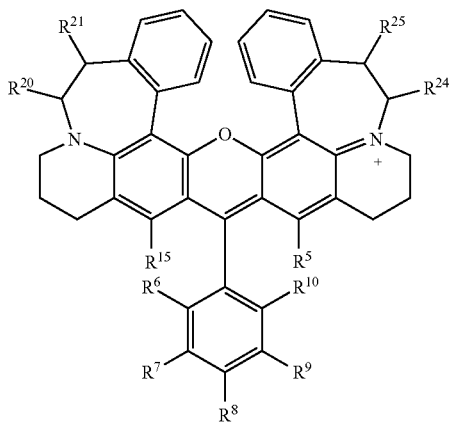

(VII)

wherein $R^5$ and $R^{15}$ are independently H, alkyl, aryl, heteroaryl, $CO_2H$, $SO_3H$, $L\text{-}CO_2H$, $L\text{-}SO_3H$, L-R or $L\text{-}C_s$;

L is a covalent linkage that is linear or branched, cyclic or heterocyclic saturated or unsaturated, having 1-16 non hydrogen atoms such that the linkage contains any combination of ester, acid, amine, amide, alcohol, ether, thioether or halide groups or single, double, triple or aromatic carbon-carbon bond;

R is a reactive group;

$C_s$ is a conjugated substance;

$R^{20}$, $R^{21}$, $R^{24}$ and $R^{25}$ are independently H or $C_{1-6}$ alkyl or one or more of $R^{20}$ and $R^{21}$ and $R^{24}$ and $R^{25}$ together form an aryl, heteroaryl, carbocyclic or heterocyclic ring; and $R^{6-10}$ are independently H, F, Cl, Br, I, OH, alkyl, aryl, heteroaryl, $CO_2H$, $SO_3H$, $L\text{-}CO_2H$, $L\text{-}SO_3H$, L-R or $L\text{-}C_s$.

In a further aspect, the invention provides a compound of formula (VIIIa) or (VIIIb):

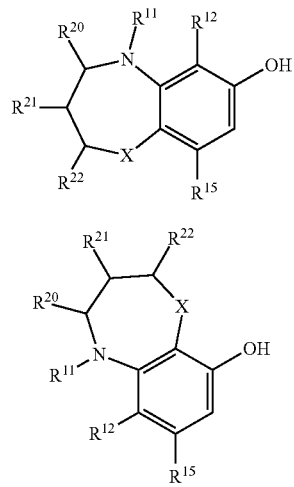

(VIIIa)

(VIIIb)

wherein $R^{11}$ is H or $C_{1-4}$ alkyl, L-R or $L\text{-}C_s$;

L is a covalent linkage that is linear or branched, cyclic or heterocyclic saturated or unsaturated, having 1-16 non hydrogen atoms such that the linkage contains any combination of ester, acid, amine, amide, alcohol, ether, thioether or halide groups or single, double, triple or aromatic carbon-carbon bond;

R is a reactive group;

$C_s$ is a conjugated substance;

$R^{12}$ and $R^{15}$ are independently H, alkyl, aryl, $CO_2H$, $SO_3H$, $L\text{-}CO_2H$, $L\text{-}SO_3H$, L-R or $L\text{-}C_s$;

$R^{20}$, $R^{21}$, $R^{22}$ and $R^{23}$ are independently H or $C_{1-6}$ alkyl or one or more of $R^{20}$ and $R^{21}$, $R^{21}$ and $R^{22}$ and $R^{22}$ and $R^{23}$ together form a fused aryl ring;

$R^{11}$ and $R^{12}$ may be joined together in an optionally substituted ring;

$R^{6-10}$ are independently H, F, Cl, Br, I, OH, alkyl, aryl, $CO_2H$, $SO_3H$, $L\text{-}CO_2H$, $L\text{-}SO_3H$, L-R or $L\text{-}C_s$;

X is $CHR^{23}$, O, S or $NR^{30}$; and $R^{30}$ is H, $C_{1-4}$ alkyl or $-C(O)C_{1-4}$ alkyl.

In some aspects, the invention provides a labeled biomolecule. In some aspects, the labeled biomolecule is a small molecule, e.g., a drug or drug compound. In other aspects, the labeled biomolecule or labeled small molecule acts as a fluorescent tracer to monitor binding to a target, e.g., drug target.

In other aspects, the invention provides a method to detect a selected molecule in a sample, comprising: a) contacting a sample suspected of containing a selected molecule with a composition comprising a conjugate comprising a compound according to the present invention and a ligand for the selected molecule so as to yield a mixture; and b) detecting the presence or amount of the compound in the mixture.

In some aspects, the invention provides a method of detecting the presence of a nucleic acid polymer in a sample comprising: contacting a sample suspected of containing a nucleic acid polymer with a composition comprising a conjugate comprising a compound according to the present invention and an oligonucleotide; and detecting the presence or amount of the compound in the sample.

In some aspects, the invention provides a method of monitoring binding to a target of interest, e.g., a drug target, comprising contacting a sample comprising a fusion protein comprising the target of interest with a small molecule conjugated to a dye described herein; and detecting binding of the small molecule conjugate to the target of interest. In some aspects, the fusion protein comprises a luciferase protein fused to the target of interest. In other aspects, the fusion protein comprises a fluorescent protein fused to the target of interest. In some aspects, wherein the fusion protein comprises a luciferase protein, binding is detected by bioluminescence resonance energy transfer (BRET). In some aspects, wherein the fusion protein comprises a fluorescent protein, binding is detected by fluorescent resonance energy transfer (FRET). In some aspects, the sample comprises a cell expressing the fusion protein.

In some aspects, the invention provides a method for monitoring protein-protein interactions comprising contacting a sample comprising a first fusion protein and a second fusion protein with a ligand conjugated to a dye described herein; and detecting the interaction between the first and second fusion protein. In some aspects, the first fusion protein comprises a luciferase protein fused to a first binding partner, the second fusion protein comprises a HaloTag® protein fused to a second binding partner, and the ligand conjugate comprises a HaloTag® ligand.

In some aspects, the invention provides reactive dyes that may be used to label a protein(s), peptide(s) or ligand(s). In some aspects, the reactive dyes of the invention could be attached to a target protein or peptide using a reactive cyanobenzothiazole labeling chemistry.

In other aspects, the invention provides a kit comprising a compound according to the present invention or a labeled biomolecule according to the present invention. In some aspects, the kit comprises a labeled biomolecule or labeled small molecule, e.g., drug or drug compound. In some aspects, the kit further comprises cells expressing a fusion protein comprising a protein or target of interest. In other aspects, the kit further comprises a vector for expressing a fusion protein comprising a protein or target of interest.

BRIEF DESCRIPTION OF THE DRAWINGS

FIGS. 1A-1E shows various compounds according to the present invention.

FIGS. 2A-2E shows various compounds according to the present invention.

FIGS. 3A-3E shows various compounds according to the present invention.

FIG. 4 shows electropherograms showing peaks of loci labeled with FAM, JOE, ET TMR, ET ROX and ET 4510. Male DNA (1.0 ng) was amplified using a 21-STR Primer Pair Mix (Table 1) and the additional loci D22S1045, D2S441 and DYS391. Amplification products were analyzed with an Applied Biosystems 3500×L Genetic Analyzer. Panel A. An electropherogram showing the peaks of the FAM-labeled loci: Amelogenin, D3S1358, D1S1656, D6S1043, D13S317 and Penta E. Panel B. An electropherogram showing the peaks of the JOE-labeled loci: Penta D, D16S539, D18S51, D2S1338 and CSF1PO. Panel C. An electropherogram showing the peaks of the ET TMR-labeled loci: TH11, vWA, D21S11, D7S820, D5S818, and TPOX. Panel D. An electropherogram showing ET ROX-labeled loci: D8S1179, D12S391, D19S433 and FGA. Panel E. An electropherogram showing ET 4510-labeled loci: D22S1045, D2S441 and DYS391. Note: Penta D is the largest loci in the JOE-labeled loci set, and the ET 4510-labeled loci are shown from smallest to largest. Loci in the other sets are shown from largest to smallest.

FIG. 5 shows electropherograms showing peaks of the loci DYS391, D2S441 and D22S1045 labeled with 4510 (Panel A), 4563 (Panel B) or 4574 (Panel C). Male DNA (1.0 ng) was amplified using a 21-STR Primer Pair Mix (Table 1) and the additional loci D22S1045, D2S441 and DYS391. Amplification products were analyzed with an Applied Biosystems 3500 xL Genetic Analyzer.

FIG. 6 shows electropherograms showing peaks of the loci DYS391, D2S441 and D22S1045 labeled with 4510 (Panel A), 4563 (Panel B), or 4574 (Panel C) and the JOE labeled loci: Penta D, D16S539, D18S51, D2S1338 and CSF1PO. Male DNA (1.0 ng) was amplified using a 21-STR Primer Pair Mix (Table 1) and the additional loci D22S1045, D2S441 and DYS391. Amplification products were analyzed with an Applied Biosystems 3500 xL Genetic Analyzer.

FIG. 7 shows electropherograms showing peaks of the loci DYS391, D2S441 and D22S1045 labeled with 4510 (Panel A), 4563 (Panel B), or 4574 (Panel C). Male DNA (0.5 ng) was amplified using a 21-STR Primer Pair Mix (Table 1) and the additional loci D22S1045, D2S441 and DYS391. Amplification products were analyzed with an Applied Biosystems 3500 xL Genetic Analyzer.

FIG. 8 shows electropherograms showing peaks of the loci DYS391, D2S441 and D22S1045 labeled with 4510 (Panel A), 4563 (Panel B), or 4574 (Panel C) and the JOE labeled loci: Penta D, D16S539, D18S51, D2S1338 and CSF1PO. Male DNA (0.5 ng) was amplified using a 21-STR Primer Pair Mix (Table 1) and the additional loci D22S1045, D2S441 and DYS391. Amplification products were analyzed with an Applied Biosystems 3500 xL Genetic Analyzer.

FIG. 9(a) U2OS cells stably expressing HaloTag® containing a nuclear localization sequence (HT-NLS) were labeled with 100 nM ligand 3780 by a no-wash protocol and imaged using 3% λ633 laser, PMT 715, CA 80 μm, 100×. FIG. 9(b) U2OS cells stably expressing HT-NLS were labeled with 1 μM ligand 3780 by a rapid label protocol and imaged using 3% λ633 laser, PMT 600, CA 200 μm, 100×. FIG. 9(c) U2OS cells stably expressing the fusion protein p65-HaloTag (p65-HT) were labeled with 1 μM ligand 3780 by a rapid label protocol and imaged using 8% λ633 laser, PMT 775, CA 80 μm, 100×. FIG. 9(d) U2OS cells labeled with 1 μM ligand 3780 by a rapid label protocol and imaged using 8% λ633 laser, PMT 775, CA 200 μm, 20×. The left panel in each image shows fluorescence channel, the middle panel shows DIC, and the right panel shows an overlay of the two.

FIG. 10(a) U2OS cells stably expressing the fusion protein p65-HT and FIG. 10(b) U2OS cells were labeled with 1 μM ligand 3781 by a rapid label protocol. Cells were imaged using 10% λ543 laser, PMT 830, CA 80 μm, 80×. The left panel in each image shows fluorescence channel, the middle panel shows DIC, and the right panel shows an overlay of the two.

FIG. 11(a) U2OS cells stably expressing HT-NLS were labeled with 100 nM ligand 3782 by a no-wash protocol and imaged using 3% λ633 laser, PMT 615, CA 80 μm, 100×. FIG. 11(b) U2OS cells stably expressing HT-NLS were labeled with 1 μM ligand 3782 by a rapid label protocol and imaged using 3% λ633 laser, PMT 600, CA 200 μm, 100×. FIG. 11(c) U2OS stably expressing the fusion protein p65-HT were labeled with 1 μM ligand 3782 by a rapid label protocol and imaged using 8% λ633 laser, PMT 775, CA 80 μm, 100×. FIG. 11(d) U2OS cells were labeled with 1 μM ligand 3782 by a rapid label protocol and imaged using 8% λ633 laser, PMT 775, CA 200 μm, 20×. The left panel in each image shows fluorescence channel, the middle panel shows DIC, and the right panel shows an overlay of the two.

FIG. 12(a) U2OS cells stably expressing HT-NLS were labeled with 100 nM ligand 3783 by a no-wash protocol and imaged using 3% λ633 laser, PMT 615, CA 80 μm, 100×. FIG. 12(b) U2OS cells stably expressing HT-NLS were labeled with 1 μM ligand 3783 by a rapid label protocol and imaged using 3% λ633 laser, PMT 600, CA 200 μm, 100×. FIG. 12(c) U2OS cells stably expressing the fusion protein p65-HT were labeled with 1 μM ligand 3783 by the rapid label protocol and imaged using 8% λ633 laser, PMT 750, CA 80 μm, 100×. FIG. 12(d) U2OS cells were labeled with 1 μM ligand 3783 by a rapid labeled protocol and imaged using 8% λ633 laser, PMT 775, CA 200 μm, 20×. The left panel in each image shows fluorescence channel, the middle panel shows DIC, and the right panel shows an overlay of the two.

FIG. 13(a) U2OS cells stably expressing HT-NLS were labeled with 1 μM ligand 3905 by a rapid label protocol and imaged using 3% λ633 laser, PMT 600, CA 200 μm, 20×. FIG. 13(b) U2OS cells stably expressing the fusion protein p65-HT and FIG. 13(c) U2OS cells were labeled with 1 μM ligand 3905 by a rapid label protocol and imaged using 15% λ633 laser, PMT800, CA 80 μm, 20×. The left panel in each image shows fluorescence channel, the middle panel shows DIC, and the right panel shows an overlay of the two.

FIG. 14(a) U2OS cells stably expressing HT-NLS were labeled with 1 μM ligand 3906 by a rapid label protocol and imaged using 3% λ633 laser, PMT 600, CA 200 μm, 20×. FIG. 14(b) U2OS cells stably expressing the fusion protein p65-HT and FIG. 14(c) U2OS cells were labeled with 1 μM ligand 3906 by a rapid label protocol and imaged using 10% λ633 laser, PMT 720, CA 80 μm, 20×. The left panel in each image shows fluorescence channel, the middle panel shows DIC, and the right panel shows an overlay of the two.

FIG. 15(a) U2OS cells stably expressing HT-NLS and FIG. 15(b) U2OS cells were labeled with 1 μM ligand 3954 by a rapid label protocol and imaged using 4% λ633 laser, PMT 880, CA 80 μm, 20×. The left panel in each image shows fluorescence channel, the middle panel shows DIC, and the right panel shows an overlay of the two.

FIG. 17(a) Fluorescent scans after SDS-PAGE showing ligand signal directly (λ633) and TMR signal (λ532). Lane 1 represents 100 nM ligand using a no-wash labeling (pulse) with 5 μM TMR rapid labeling (chase), lane 2 represents 1 μM rapid labeling (pulse) with 5 μM TMR rapid labeling (chase), lane 3 represents 5 μM rapid labeling (pulse) with 5 μM TMR rapid labeling (chase), "TMR" represents cells labeled only with TMR ligand. FIG. 17(b) Graph showing quantification of bands (TMR signal) from TMR gel as a percent of TMR alone band.

FIG. 23B shows the emission spectra for NanoLuc luciferase and PBI 3781 and excitation spectra for PBI 3781

DETAILED DESCRIPTION

Definitions

Figure 1A:
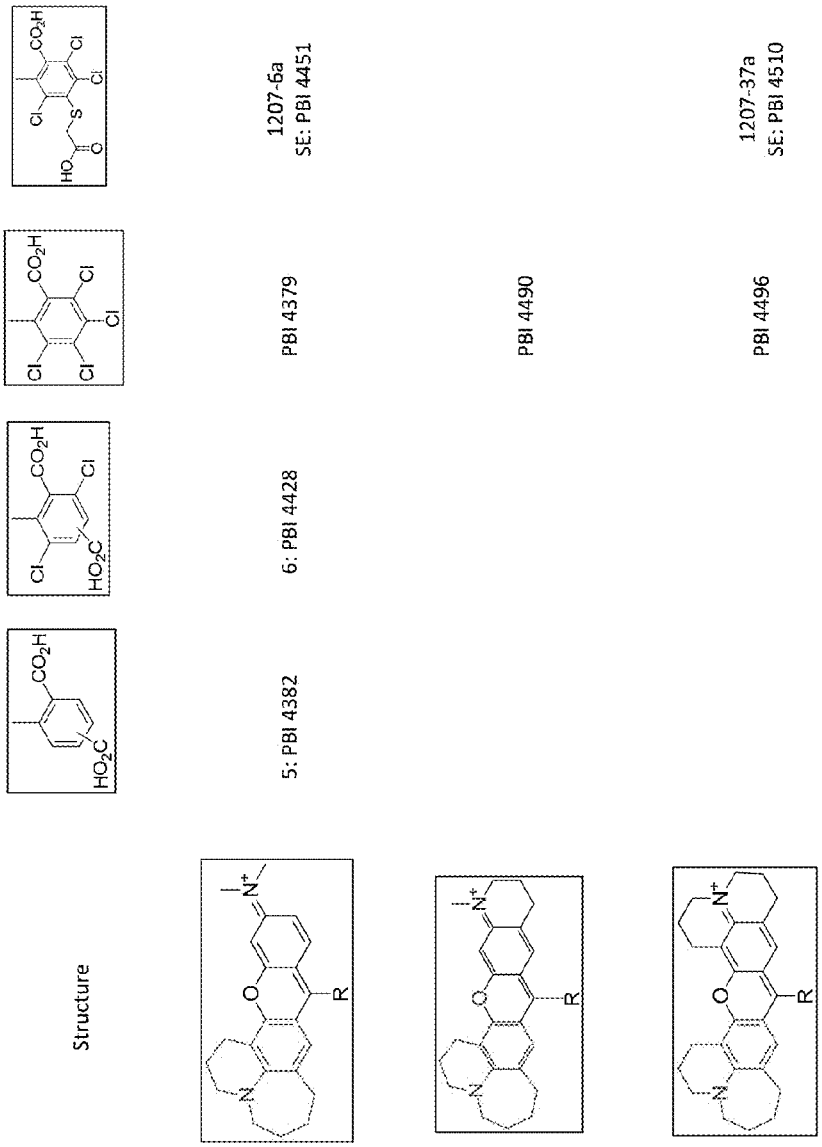

As used herein, the following terms and expressions have the indicated meanings. Specific values listed below for radicals, substituents, and ranges are for illustration only. They do not exclude other defined values or other values within defined ranges for the radicals and substituents.

When a group or moiety can be substituted, the term "substituted" indicates that one or more (e.g., 1, 2, 3, 4, 5, or 6; in some embodiments 1, 2, or 3; and in other embodiments 1 or 2) hydrogens on the group indicated in the expression using "substituted" can be replaced with a selection of recited indicated groups or with a suitable group known to those of skill in the art (e.g., one or more of the groups recited below), provided that the indicated atom's normal valency is not exceeded, and that the substitution results in a stable compound. Suitable substituents of a substituted group can include alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acetylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, and cyano. Additionally, the suitable indicated groups can include, e.g., —X, —R, —O—, —OR, —SR, —S—, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NRR —S(=O)$_2$O—, —S(=O)$_2$OH, —S(=O)$_2$R, —OS(=O)$_2$OR, —S(=O)$_2$NR, —S(=O)R, —OP(=O)O$_2$RR, —P(=O)O$_2$RR, —P(=O)(O—)$_2$, —P(=O)(OH)$_2$, —C(=O)R, —C(=O)X, —C(S)R, —C(O)OR, —C(O)O—, —C(S)OR, —C(O)SR, —C(S)SR, —C(O)NRR, —C(S)NRR, —C(NR)NRR, where each X is independently a halogen ("halo"): F, Cl, Br, or I; and each R is independently H, alkyl, aryl, heteroaryl, heterocycle, a protecting group or prodrug moiety. As would be readily understood by one skilled in the art, when a substituent is keto (=O) or thioxo (=S), or the like, then two hydrogen atoms on the substituted atom are replaced.

As used herein, the term "alkyl" refers to a branched, unbranched, or cyclic hydrocarbon having, for example, from 1 to 20 carbon atoms, and often 1 to 12, or 1 to about 6 carbon atoms. Examples include, but are not limited to, methyl, ethyl, 1-propyl, 2-propyl, 1-butyl, 2-methyl-1-propyl, 2-butyl, 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted. For example, a substituted alkyl group can be a haloalkyl group, as described below. The alkyl can also be optionally partially or fully unsaturated. As such, the recitation of an alkyl group includes both alkenyl and alkynyl groups. The alkyl can be a monovalent hydrocarbon radical, as described and exemplified above, or it can be a divalent hydrocarbon radical (i.e., alkylene), according to the context of its usage. Additionally, the alkyl group can be optionally interrupted, as described below for the term interrupted.

The term "alkenyl" refers to a monoradical branched or unbranched partially unsaturated hydrocarbon chain (i.e. a carbon-carbon, sp$^2$ double bond). In one embodiment, an alkenyl group can have from 2 to 10 carbon atoms, or 2 to 6 carbon atoms. In another embodiment, the alkenyl group has from 2 to 4 carbon atoms. Examples include, but are not limited to, ethylene or vinyl, allyl, cyclopentenyl, 5-hexenyl, and the like. The alkenyl can be unsubstituted or substituted.

The term "alkynyl" refers to a monoradical branched or unbranched hydrocarbon chain, having a point of complete unsaturation (i.e. a carbon-carbon, sp triple bond). In one embodiment, the alkynyl group can have from 2 to 10 carbon atoms, or 2 to 6 carbon atoms. In another embodiment, the alkynyl group can have from 2 to 4 carbon atoms. This term is exemplified by groups such as ethynyl, 1-propynyl, 2-propynyl, 1-butynyl, 2-butynyl, 3-butynyl, 1-hexynyl, 2-hexynyl, 3-hexynyl, 1-octynyl, and the like. The alkynyl can be unsubstituted or substituted.

The term "cycloalkyl" or "carbocyle" or "carbocyclic" refers to cyclic alkyl groups of from 3 to about 10 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like. The cycloalkyl can be unsubstituted or substituted. The cycloalkyl group can be monovalent or divalent, and can be optionally substituted as described above for alkyl groups. The cycloalkyl group can optionally include one or more cites of unsaturation, for example, the cycloalkyl group can include one or more carbon-carbon double bonds, such as, for example, cyclohexene, 1,3-cyclohexadiene, 1,4-cyclohexadiene, and the like. The cycloalkyl group can be a carbocycle, which refers to a saturated or partially unsaturated ring having 3 to 8 carbon atoms as a monocycle, 7 to 12 carbon atoms as a bicycle, and up to about 20 carbon atoms as a polycycle. Monocyclic carbocycles typically have 3 to 6 ring atoms, still more typically 5 or 6 ring atoms. Bicyclic carbocycles have 7 to 12 ring atoms, e.g., arranged as a bicyclo[4,5], [5,5], [5,6] or [6,6] system, or 9 or 10 ring atoms arranged as a bicyclo[5,6] or [6,6] system. Examples of carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, or 1-cyclohex-3-enyl. The carbocycle can be optionally substituted as described above for alkyl groups.

The term "alkoxy" refers to the group alkyl-O—, where alkyl is as defined herein. In one embodiment, alkoxy groups include, e.g., methoxy, ethoxy, n-propoxy, iso-propoxy, n-butoxy, tert-butoxy, sec-butoxy, n-pentoxy, n-hexyloxy, 1,2-dimethylbutoxy, and the like. The alkoxy can be unsubstituted or substituted.

The term "aryl" refers to an aromatic hydrocarbon group derived from the removal of one hydrogen atom from a single carbon atom of a parent aromatic ring system. The radical can be at a saturated or unsaturated carbon atom of the parent ring system. The aryl group can have 6-18 carbon atoms, 6-14 carbon atoms, or 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described above for alkyl groups. For example, an aryl group can be substituted with one or more substituents (as described above) to provide various substituted aryls, such as pentafluorophenyl or para-trifluoromethylphenyl, and the like.

The term "halo" refers to the groups fluoro, chloro, bromo, and iodo. Similarly, the term "halogen" refers to fluorine, chlorine, bromine, and iodine.

The term "heteroaryl" is defined herein as a monocyclic, bicyclic, or tricyclic ring system containing one, two, or three aromatic rings and containing at least one nitrogen, oxygen, or sulfur atom in an aromatic ring, and that can be unsubstituted or substituted, for example, with one or more, and in particular one to three, substituents, as described above in the definition of "substituted". Typical heteroaryl groups contain 2-14 carbon atoms in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidazolyl, indazolyl, indolisinyl, indolyl, isobenzofuranyl, isoindolyl, isoquinolyl, isothiazolyl, isoxazolyl, naphthyridinyl, oxazolyl, pyrimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or $(C_1-C_6)$ alkylaryl. In another embodiment heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "heterocycle" refers to a saturated or partially unsaturated ring system, containing at least one heteroatom selected from the group oxygen, nitrogen, and sulfur, with a ring size of 3 to about 12 atoms, or bicyclic ring systems that include a total of about 7 to about 14 ring atoms, and optionally substituted with one or more groups as defined herein under the term "substituted". A heterocycle can be a monocyclic, bicyclic, or tricyclic group containing one or more heteroatoms. A heterocycle group also can contain an oxo group (═O) or a thioxo (═S) group attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine.

The term "heterocycle" can include, by way of example and not limitation, a monoradical of the heterocycles described in Paquette, Leo A.; Principles of Modern Heterocyclic Chemistry (W. A. Benjamin, New York, 1968), particularly Chapters 1, 3, 4, 6, 7, and 9; The Chemistry of Heterocyclic Compounds, A Series of Monographs" (John Wiley & Sons, New York, 1950 to present), in particular Volumes 13, 14, 16, 19, and 28; and J. Am. Chem. Soc. 1960, 82, 5566. In one embodiment, "heterocycle" includes a "carbocycle" as defined herein, wherein one or more (e.g. 1, 2, 3, or 4) carbon atoms have been replaced with a heteroatom (e.g. O, N, or S).

Heterocycles, by way of example and not limitation, include dihydropyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, 5-thiazolyl, and the like.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. In one embodiment, nitrogen bonded heterocycles include 1-aziridyl, 1-azetedyl, 1-pyrrolyl, 1-imidazolyl, 1-pyrazolyl, and 1-piperidinyl.

The term "amino" refers to —NH$_2$. The amino group can be optionally substituted as defined herein for the term "substituted", e.g., the amino group can be —NR$_2$ where R is a group recited in the definition of substituted. For example, the groups —NR$_2$ can include "alkylamino" wherein at least one R is alkyl and the second R is alkyl or hydrogen, and/or "acylamino" (—N(R)C(=O)R), wherein each R is independently hydrogen, alkyl, alkaryl or aryl.

The term "alkaryl" refers to an aryl group substituted with at least one alkyl group, which together form a substituent through a radical on either the alkyl or the aryl group. The alkyl group of the alkaryl can include about 1-8 carbon atoms, either linear or branched. Typical alkaryl groups include benzyl, 2-phenylethyl, 3-phenylpropyl, 4-phenylbuty, 5-phenylpentyl, 6-phenylhexyl, 7-phenylheptyl, 8-phenyloctyl, branched alkyl chain derivatives thereof, and naphthalene versions thereof. The alkaryl can be optionally substituted as described above for alkyl groups.

The term "interrupted" indicates that another group is inserted between two adjacent carbon atoms (and the hydrogen atoms to which they are attached (e.g., methyl (CH$_3$), methylene (CH$_2$) or methine (CH))) of a particular carbon chain being referred to in the expression using the term "interrupted", provided that each of the indicated atoms' normal valency is not exceeded and the interruption results in a stable compound. Suitable groups that can interrupt a carbon chain include, e.g., with one or more non-peroxide oxy (—O—), thio (—S—), imino (—N(H)—), methylenedioxy (—OCH$_2$O—), carbonyl (—C(=O)—), carboxy (—C(=O)O—), carbonyldioxy (—OC(=O)O—), carboxylato (—OC(=O)—), imine (C=NH), sulfinyl (SO) and sulfonyl (SO$_2$). Alkyl groups can be interrupted by one or more (e.g., 1, 2, 3, 4, 5, or about 6) of the aforementioned suitable groups. The site of interruption can also be between a carbon atom of an alkyl group and a carbon atom to which the alkyl group is attached.

As to any of the above groups, which contain one or more substituents, it is understood, of course, that such groups do not contain any substitution or substitution patterns that are sterically impractical and/or synthetically non-feasible. In addition, the compounds of this invention include all stereochemical isomers arising from the substitution of these compounds. It will be appreciated that some compounds of the present invention may contain asymmetrically substituted carbon atoms, and may be isolated in optically active or racemic forms. It is well known in the art how to prepare optically active forms, such as by resolution of racemic forms or by synthesis from optically active starting materials. All chiral, diastereomeric, racemic forms and all geometric isomeric forms of a structure are part of this invention. In addition, some compounds of the present invention may exist as rotational isomers. In some instances, these rotational isomers may be separated. Both rotational isomers and a mixture thereof are contemplated by the present invention.

One isomeric form may display superior properties or activity compared with another. When required, separation of the racemic material can be achieved by HPLC using a chiral column or by a resolution using a resolving agent such as camphonic chloride as described by Tucker et al., *J. Med. Chem.*, 37: 2437 (1994). A chiral compound may also be directly synthesized using a chiral catalyst or a chiral ligand, e.g. Huffman et al., *J. Org. Chem.*, 60: 1590 (1995).

An "effective amount" generally means an amount that provides a desired effect, for example, an amount sufficient to bring about a reaction.

As used herein, "contacting" refers to the act of touching, making contact, or of bringing to immediate or close proximity, including at the molecular level, for example, to bring about a chemical reaction or physical change, e.g., in a solution, cell, or other reaction mixture.

The term "reactive group" refers to an activated ester of a carboxylic acid, an amine, an alcohol, a sulfonyl halide, a mercaptan, a boronate, a phosphoramidite, an isocyanate, a haloacetamide, an aldehyde, an azide, an acyl nitrile, a photoactivateable group or an alkyl halide.

The term "conjugated substance" refers to a covalently bound substance such as a surface (e.g. a bead, solid support, resin particle, or an assay plate), biological molecule (e.g., proteins, nucleotides, polynucleotides including DNA and RNA, enzyme substrates, antibodies, nanobodies, polypeptides, polypeptide-based toxins, amino acids, lipids, carbohydrates, haptens, small molecules, drugs, drug compounds, ion-complexing agents, such as metal chelators, microparticles, synthetic or natural polymers, cells, viruses, other fluorescent molecules or surfaces), or other moieties of interest, e.g. a chloroalkane or a cyanobenzothiazole.

A "tracer" is a type of conjugated substance where a dye of the present invention is conjugated to a biological molecule as defined above, possibly through a linker.

The term "traceless linker" or "self-immolative linker" refers to a linker wherein cleavage of a conjugated substance from the linker results in spontaneous cleavage of the linker from the dye to release the unbound dye. Exemplary traceless linkers include:

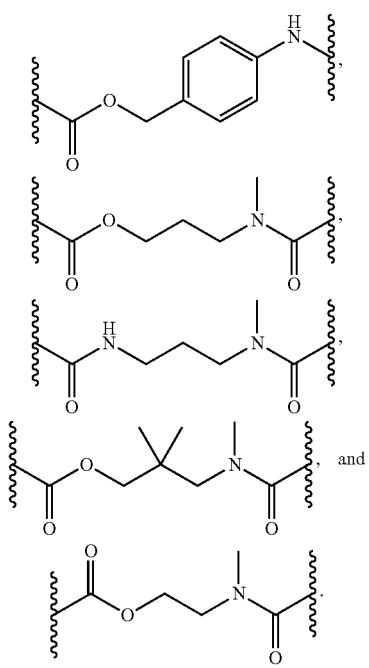

As would be recognized by one of ordinary skill in the art, further variations in linker length and substitution are possible.

Dyes

The invention provides compounds of Formula (Ia) and (Ib):

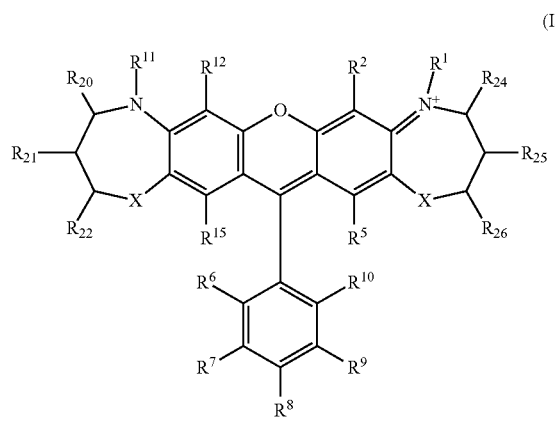

(Ia)

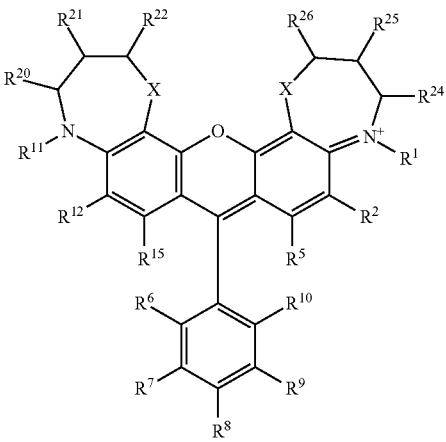

(Ib)

wherein $R^1$ and $R^{11}$ are independently H or $C_{1-4}$ alkyl, L-R or L-$C_s$;

L is a covalent linkage that is linear or branched, cyclic or heterocyclic saturated or unsaturated, having 1-16 non hydrogen atoms such that the linkage contains any combination of ester, acid, amine, amide, alcohol, ether, thioether or halide groups or single, double, triple or aromatic carbon-carbon bond;

R is a reactive group;

$C_s$ is a conjugated substance;

$R^2$, $R^5$, $R^{12}$ and $R^{15}$ are independently H, alkyl, aryl, heteroaryl, $CO_2H$, $SO_3H$, L-$CO_2H$, L-$SO_3H$, L-R or L-$C_s$;

$R^{20}$, $R^{21}$, $R^{22}$, $R^{23}$, $R^{24}$, $R^{25}$, and $R^{26}$ are independently H or $C_{1-6}$ alkyl or one or more of $R^{20}$ and $R^{21}$, $R^{21}$ and $R^{22}$, $R^{22}$ and $R^{23}$, $R^{24}$ and $R^{25}$, $R^{25}$ and $R^{26}$, and $R^{26}$ and $R^{23}$ together form an aryl, heteroaryl, carbocyclic or heterocyclic ring;

$R^1$ and $R^2$ and/or $R^{11}$ and $R^{12}$ may together form a carbocyclic, heterocyclic, aryl or heteroaryl ring;

$R^{6-16}$ are independently H, halo, OH, alkyl, aryl, heteroaryl, $CO_2H$, $SO_3H$, L-$CO_2H$, L-$SO_3H$, L-R or L-$C_s$;

each X is independently $CHR^{23}$, O, S or $NR^{30}$; and $R^{30}$ is H, $C_{1-4}$ alkyl or —C(O)$C_{1-4}$ alkyl.

In some embodiments, the ring formed by $R^1$ and $R^2$ or $R^{11}$ and $R^{12}$ can be from 3-10 atoms chosen from C, N, O and S. In other embodiments, the ring has from 5 to 7 atoms. In certain embodiments, the ring atoms are all carbon. These rings may contain elements of unsaturation as well. In certain embodiments, these rings are aryl or heteroaryl rings.

In Formula (Ib), $R^2$ and $R^5$ may together form an aryl or heteroaryl ring. Suitably, the ring is phenyl or thiophenyl. In some embodiments, the ring is substituted.

Suitably, X is $CH_2$. $R^{11}$ is suitably $C_{1-4}$ alkyl. In some embodiments, $R^{11}$ is methyl or ethyl. In other embodiments, $R^{11}$ and $R^{12}$ form a 5-7 membered carbocyclic ring. Suitably, the ring is an unsubstituted 6-membered ring. Suitably, $R^2$ and $R^{12}$ are H, Cl or OMe. $R^5$ and $R^{15}$ may be H.

The invention also provides compounds of formula (IIa) and (IIb):

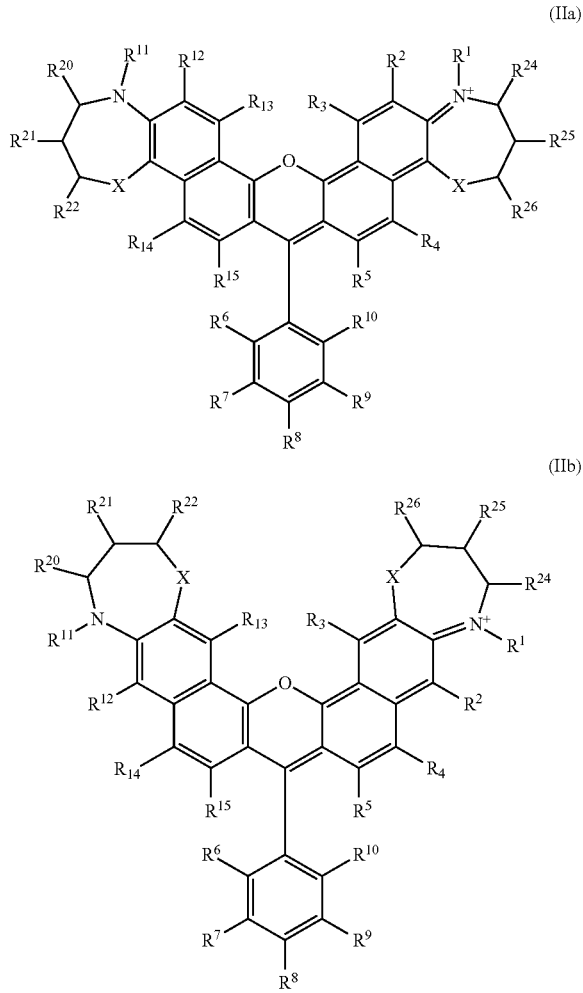

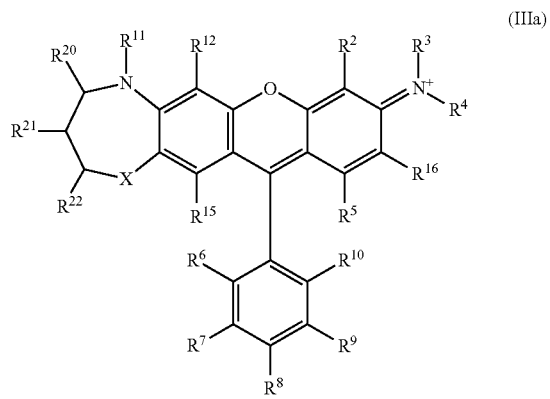

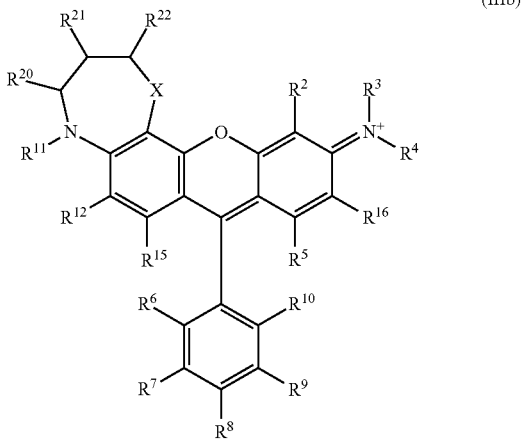

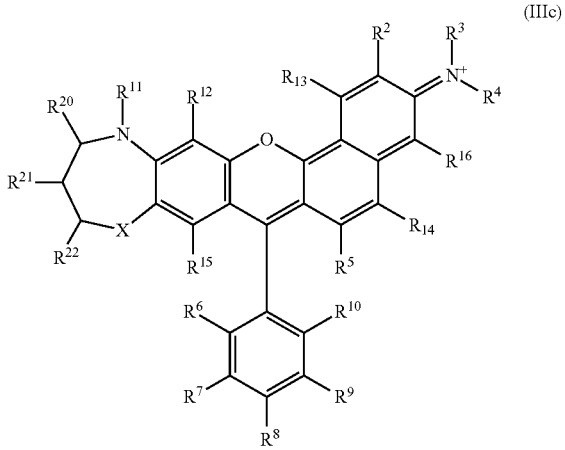

wherein $R^1$ and $R^{11}$ are independently H or $C_{1-4}$ alkyl, L-R or L-$C_s$;

L is a covalent linkage that is linear or branched, cyclic or heterocyclic saturated or unsaturated, having 1-16 non hydrogen atoms such that the linkage contains any combination of ester, acid, amine, amide, alcohol, ether, thioether or halide groups or single, double, triple or aromatic carbon-carbon bond;

R is a reactive group;

$C_s$ is a conjugated substance;

$R^2$, $R^3$, $R^4$, $R^5$, $R^{12}$, $R^{13}$, $R^{14}$ and $R^{15}$ are independently H, alkyl, aryl, heteroaryl, $CO_2H$, $SO_3H$, L-$CO_2H$, L-$SO_3H$, L-R or L-$C_s$;

$R^{20}$, $R^{21}$, $R^{22}$, $R^{23}$, $R^{24}$, $R^{25}$ and $R^{26}$ are independently H or $C_{1-6}$ alkyl or one or more of $R^{20}$ and $R^{21}$, $R^{21}$ and $R^{22}$, $R^{22}$ and $R^{23}$, $R^{24}$ and $R^{25}$, $R^{25}$ and $R^{26}$, and $R^{26}$ and $R^{23}$ together form an aryl, heteroaryl, carbocyclic or heterocyclic ring;

$R^1$ and $R^2$ and/or $R^{11}$ and $R^{12}$ may together form a carbocyclic, heterocyclic, aryl or heteroaryl ring;

$R^{6-10}$ are independently H, F, Cl, Br, I, OH, alkyl, aryl, heteroaryl, $CO_2H$, $SO_3H$, L-$CO_2H$, L-$SO_3H$, L-R or L-$C_s$;

each X is independently $CHR^{23}$, O, S or $NR^{30}$; and $R^{30}$ is H, $C_{1-4}$ alkyl or —$C(O)C_{1-4}$ alkyl.

In some embodiments, the ring formed by $R^1$ and $R^2$ or $R^{11}$ and $R^{12}$ can be from 3-10 atoms chosen from C, N, O and S. In other embodiments, the ring has from 5 to 7 atoms. In certain embodiments, the ring atoms are all carbon. These rings may contain elements of unsaturation as well. In certain embodiments, the rings may be aryl or heteroaryl rings.

In Formula (IIa), one or more of $R^2$ and $R^3$, $R^4$ and $R^5$, $R^{12}$ and $R^{13}$ or $R^{14}$ and $R^{15}$ can also be joined together with an aryl or heteroaryl ring. In Formula (IIb), one or both of $R^4$ and $R^5$ or $R^{14}$ and $R^{15}$ may together form an aryl or heteroaryl ring. Suitably, the ring is phenyl or thiophenyl. In some embodiments, the ring is substituted.

Suitably, X is $CH_2$. $R^{11}$ is suitably $C_{1-4}$ alkyl. In some embodiments, $R^{11}$ is methyl or ethyl. In other embodiments, $R^{11}$ and $R^{12}$ together form a 5-7 membered carbocyclic ring. Suitably, the ring is an unsubstituted 6-membered ring. Suitably, $R^2$, $R^5$, $R^{12}$ and $R^{15}$ are H.

The invention also provides compounds of formula (IIIa), (IIIb) and (IIIc):

wherein
$R^{11}$ is independently H or $C_{1-4}$ alkyl, L-R or $L-C_s$;
L is a covalent linkage that is linear or branched, cyclic or heterocyclic saturated or unsaturated, having 1-16 non hydrogen atoms such that the linkage contains any combination of ester, acid, amine, amide, alcohol, ether, thioether or halide groups or single, double, triple or aromatic carbon-carbon bond;
R is a reactive group;
$C_s$ is a conjugated substance;
$R^2$ and $R^{16}$ can be independently H, alkyl, aryl, heteroaryl, $CO_2H$, $SO_3H$, $L-CO_2H$, $L-SO_3H$, L-R or $L-C_s$;
$R^3$ and $R^4$ are H, alkyl, L-R, $L-C_s$, $L-CO_2H$, $L-SO_3H$ or together form a carbocyclic, aryl, heteroaryl, or heterocyclic ring;
alternatively, $R^2$ and $R^3$ and independently $R^4$ and $R^{16}$ together form a carbocyclic, heterocyclic, aryl or heteroaryl ring;
$R^5$, $R^{12}$, $R^{13}$, $R^{14}$ and $R^{15}$ are independently H, alkyl, aryl, heteroaryl, $CO_2H$, $SO_3H$, $L-CO_2H$, $L-SO_3H$, L-R or $L-C_s$;
$R^{20}$, $R^{21}$, $R^{22}$ and $R^{23}$ are independently H or $C_{1-4}$ alkyl or one or more of $R^{20}$ and $R^{21}$, $R^{21}$ and $R^{22}$, $R^{22}$ and $R^{23}$, together form an aryl, heteroaryl, carbocyclic or heterocyclic ring;
$R^{11}$ and $R^{12}$ may together form a carbocyclic, heterocyclic, aryl or heteroaryl ring;
$R^{6-10}$ are independently H, F, Cl, Br, I, OH, alkyl, aryl, heteroaryl, $CO_2H$, $SO_3H$, $L-CO_2H$, $L-SO_3H$, L-R or $L-C_s$;
X is $CHR^{23}$, O, S or $NR^{30}$; and
$R^{30}$ is H, $C_{1-4}$ alkyl or $—C(O)C_{1-4}$ alkyl.

In formulas (IIIa) and (IIIb), $R^{16}$ and $R^5$ may together form a carbocyclic, heterocyclic, aryl or heteroaryl ring. In formula (IIIc), $R^{14}$ and $R^5$ and/or $R^2$ and $R^{13}$ may together form a carbocyclic, heterocyclic, aryl or heteroaryl ring. Suitably, the ring is a phenyl or thiophenyl. In some embodiments, the ring is substituted.

In some embodiments, the ring formed by $R^{11}$ and $R^{12}$ can be from 3-10 atoms chosen from C, N, O and S. In other embodiments, the ring has from 5 to 7 atoms. In certain embodiments, the ring atoms are all carbon. These rings may contain elements of unsaturation as well. In certain embodiments, the ring is aryl or heteroaryl.

The invention also provides compounds according to Formula (IV):

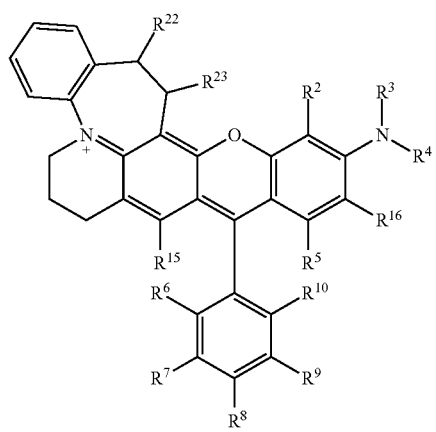

(IV)

wherein
$R^2$ and $R^{16}$ can be independently H, alkyl, aryl, heteroaryl, $CO_2H$, $SO_3H$, $L-CO_2H$, $L-SO_3H$, L-R or $L-C_s$;
L is a covalent linkage that is linear or branched, cyclic or heterocyclic saturated or unsaturated, having 1-16 non hydrogen atoms such that the linkage contains any combination of ester, acid, amine, amide, alcohol, ether, thioether or halide groups or single, double, triple or aromatic carbon-carbon bond;
R is a reactive group;
$C_s$ is a conjugated substance;
$R^3$ and $R^4$ are H, alkyl or together form a carbocyclic, aryl, heteroaryl, or heterocyclic ring;
alternatively, $R^2$ and $R^3$ and independently $R^4$ and $R^{16}$ together form a carbocyclic, heterocyclic, aryl or heteroaryl ring;
$R^5$ and $R^{15}$ are independently H, alkyl, aryl, heteroaryl, $CO_2H$, $SO_3H$, $L-CO_2H$, $L-SO_3H$, L-R or $L-C_s$;
$R^{22}$ and $R^{23}$ are independently H or $C_{1-6}$ alkyl or together form an aryl, heteroaryl, carbocyclic or heterocyclic ring; and
$R^{6-10}$ are independently H, F, Cl, Br, I, OH, alkyl, aryl, heteroaryl, $CO_2H$, $SO_3H$, $L-CO_2H$, $L-SO_3H$, L-R or $L-C_s$.

The invention further provides compounds according to Formula (V):

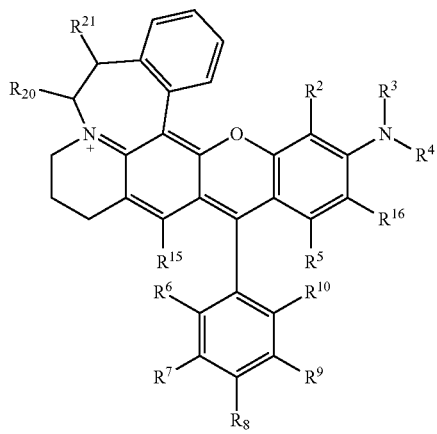

(V)

wherein
$R^2$ and $R^{16}$ can be independently H, alkyl, aryl, heteroaryl, $CO_2H$, $SO_3H$, $L-CO_2H$, $L-SO_3H$, L-R or $L-C_s$;
L is a covalent linkage that is linear or branched, cyclic or heterocyclic saturated or unsaturated, having 1-16 non hydrogen atoms such that the linkage contains any combination of ester, acid, amine, amide, alcohol, ether, thioether or halide groups or single, double, triple or aromatic carbon-carbon bond;
R is a reactive group;
$C_s$ is a conjugated substance;
$R^3$ and $R^4$ are H, alkyl, or together form a carbocyclic, heterocyclic, aryl or heteroaryl ring;
alternatively, $R^2$ and $R^3$ and independently $R^4$ and $R^{16}$ may together form a carbocyclic, heterocylic, aryl or heteroaryl ring;
$R^5$ and $R^{15}$ are independently H, alkyl, aryl, heteoaryl, $CO_2H$, $SO_3H$, $L-CO_2H$, $L-SO_3H$, L-R or $L-C_s$;
$R^{20}$ and $R^{21}$ are independently H or $C_{1-6}$ alkyl or together form an aryl, heteroaryl, carbocyclic or heterocyclic ring; and
$R^{6-10}$ are independently H, F, Cl, Br, I, OH, alkyl, aryl, heteroaryl, $CO_2H$, $SO_3H$, $L-CO_2H$, $L-SO_3H$, L-R or $L-C_s$.

The invention additionally provides compounds according to Formula (VI):

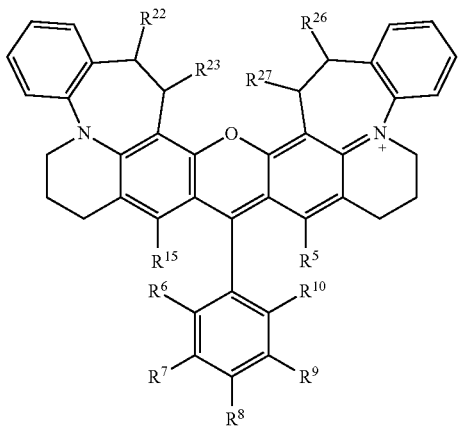

wherein $R^5$ and $R^{15}$ are independently H, alkyl, aryl, heteroaryl, $CO_2H$, $SO_3H$, $L-CO_2H$, $L-SO_3H$, L-R or $L-C_s$;

L is a covalent linkage that is linear or branched, cyclic or heterocyclic saturated or unsaturated, having 1-16 non hydrogen atoms such that the linkage contains any combination of ester, acid, amine, amide, alcohol, ether, thioether or halide groups or single, double, triple or aromatic carbon-carbon bond;

R is a reactive group;

$C_s$ is a conjugated substance;

$R^{22}$, $R^{23}$, $R^{26}$ and $R^{27}$ are independently H or $C_{1-6}$ alkyl or one or more of $R^{22}$ and $R^{23}$ and $R^{26}$ and $R^{27}$ together form an aryl, heteroaryl, carbocyclic or heterocyclic ring; and $R^{6-10}$ are independently H, F, Cl, Br, I, OH, alkyl, aryl, heteroaryl, $CO_2H$, $SO_3H$, $L-CO_2H$, $L-SO_3H$, L-R or $L-C_s$.

The invention additionally provides compounds according to Formula (VII):

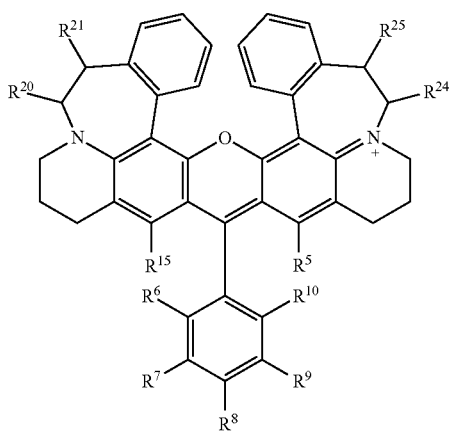

wherein $R^5$ and $R^{15}$ are independently H, alkyl, aryl, heteroaryl, $CO_2H$, $SO_3H$, $L-CO_2H$, $L-SO_3H$, L-R or $L-C_s$;

L is a covalent linkage that is linear or branched, cyclic or heterocyclic saturated or unsaturated, having 1-16 non hydrogen atoms such that the linkage contains any combination of ester, acid, amine, amide, alcohol, ether, thioether or halide groups or single, double, triple or aromatic carbon-carbon bond;

R is a reactive group;

$C_s$ is a conjugated substance;

$R^{20}$, $R^{21}$, $R^{24}$ and $R^{25}$ are independently H or $C_{1-6}$ alkyl or one or more of $R^{20}$ and $R^{21}$ and $R^{24}$ and $R^{25}$ together form an aryl, heteroaryl, carbocyclic or heterocyclic ring; and $R^{6-10}$ are independently H, F, Cl, Br, I, OH, alkyl, aryl, heteroaryl, $CO_2H$, $SO_3H$, $L-CO_2H$, $L-SO_3H$, L-R or $L-C_s$.

The following statements apply to Formulae (I)-(VII), where appropriate. Suitably, $R^2$, $R^5$ and $R^{15}$ are H. $R^3$ and $R^4$ are suitably $C_{1-4}$ alkyl. In some embodiments, $R^3$ and $R^4$ are methyl or ethyl. $R^3$ and $R^4$ may together form a heterocycle, such as a piperazine. In other embodiments, $R^2$ and $R^3$ and/or $R^4$ and $R^{16}$ together form a 5-7 membered carbocylic ring. The ring is suitably an unsubstituted 6-membered ring.

$R^{10}$ is suitably H, F, Cl, $CO_2H$ or $SO_3H$. In certain embodiments, $R^{10}$ is H. $R^6$ and $R^9$ are suitably H or halo. In certain embodiments, $R^6$ and $R^9$ may be either Cl or F.

Suitably, one of $R^7$ and $R^8$ is -L-R, $-L-CO_2H$ or $-L-C_s$ and the other is H, Cl, or F.

L is suitably $-CO-$, $-SCH_2CO-$ or $-SO_2-$. L may also contain a PEG moiety. In other embodiments, L is a "traceless" or "self-immolative" linker.

Suitably, R is

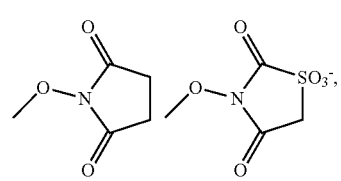

or —Cl, with SE most preferred.

$C_s$ is suitably a chloroalkane of the formula $NHCH_2CH_2(OCH_2CH_2)_n(CH_2)_6Cl$, with n being 2-6; a nucleoside, for example

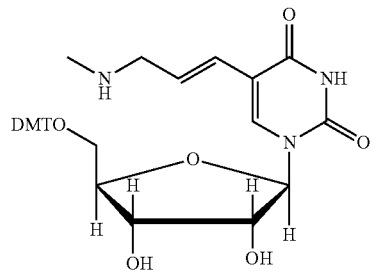

(allylaminodU); an oligonucleotide suitably attached through allylaminodU; or a cyanobenzothiazole. Suitably, the cyanobenzothiazole is

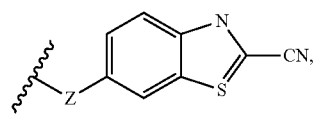

wherein Z is O or NH.

Figure 1B:
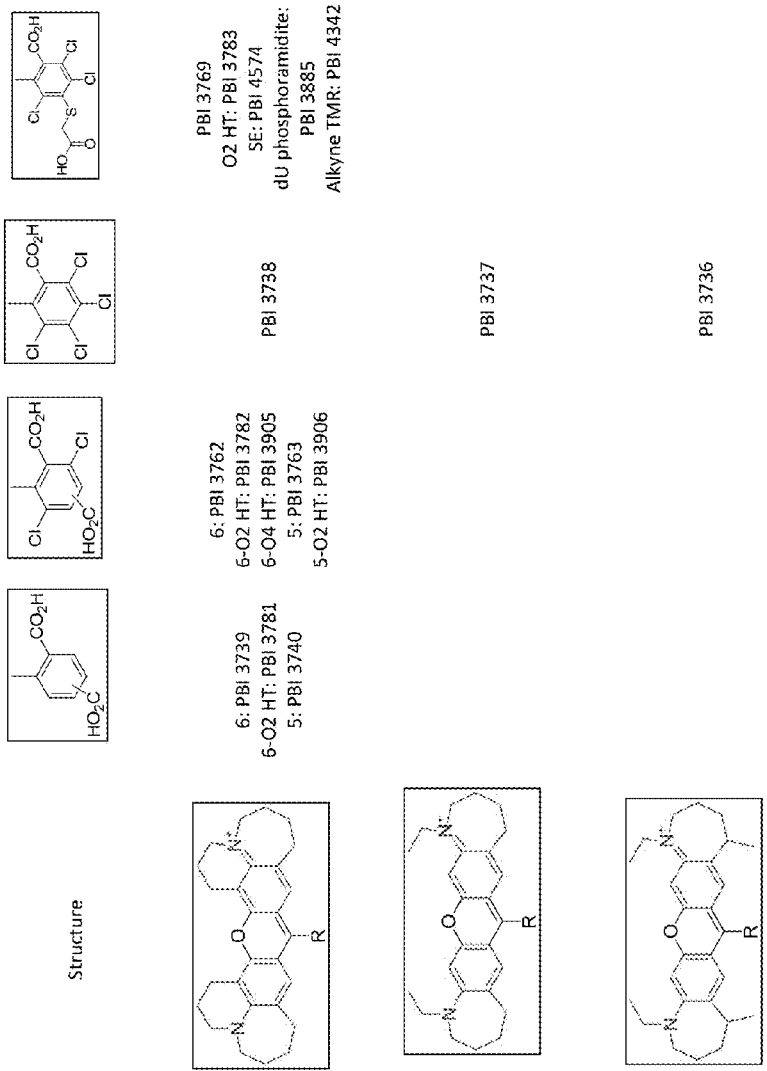
Figure 1C:
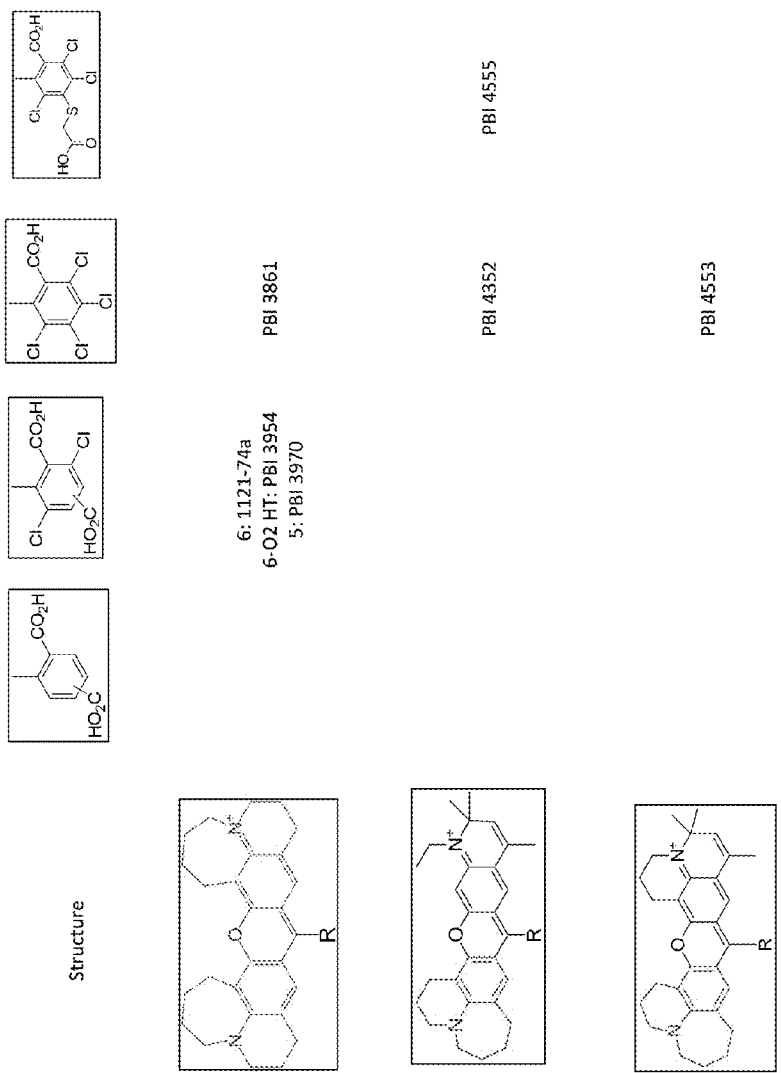
Figure 2B:
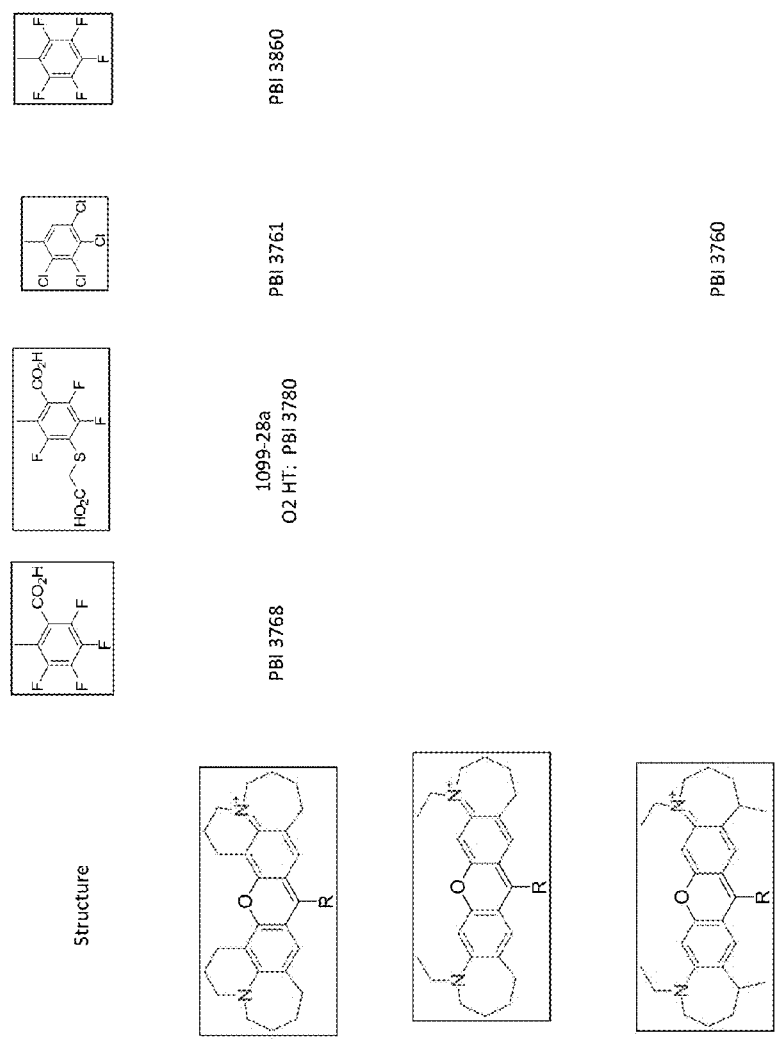
Figures 9A, 9B, 9C, 9D:
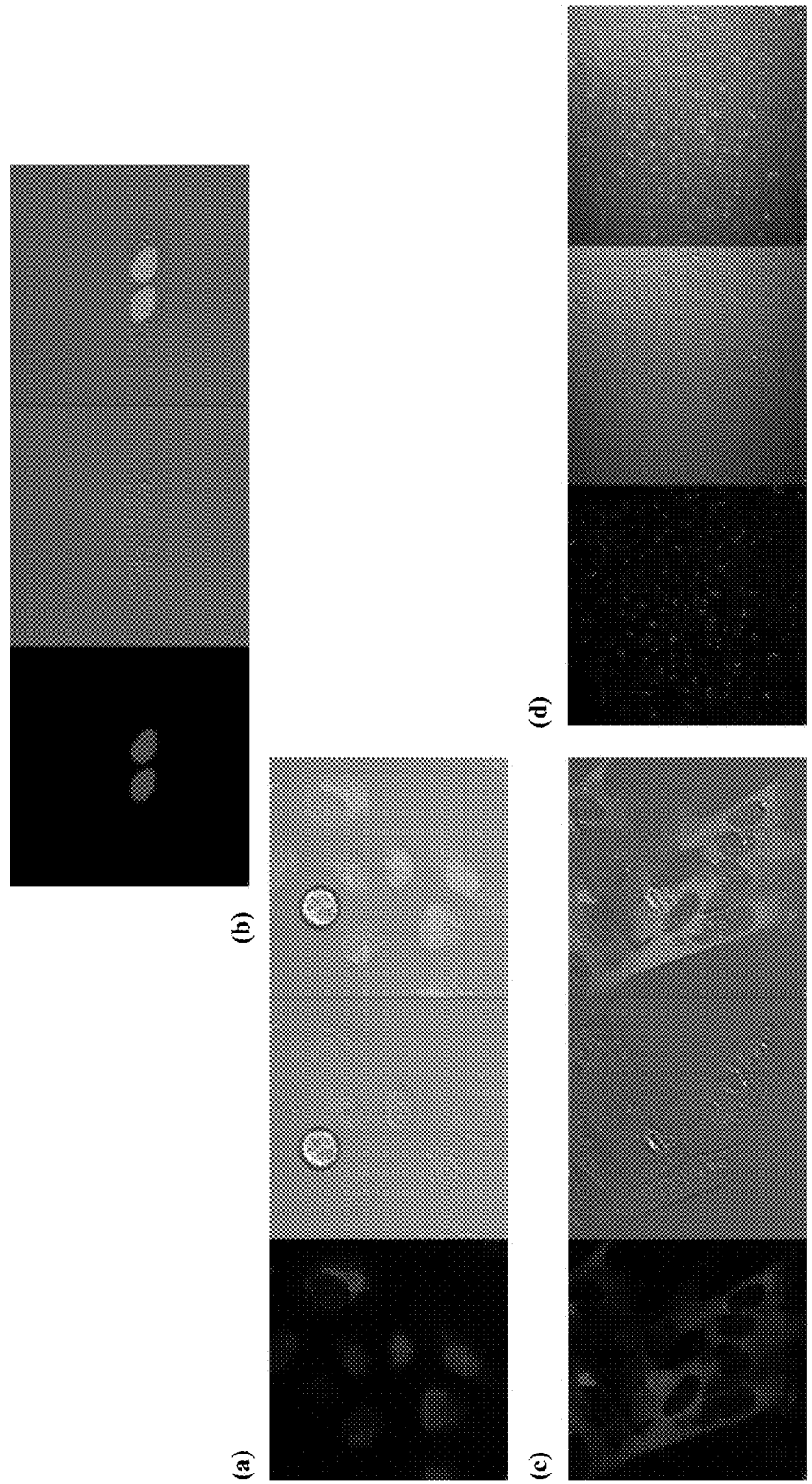
FIGS. 9(a)-9(d) shows confocal images using ligand 3780.
Figures 10A, 10B:
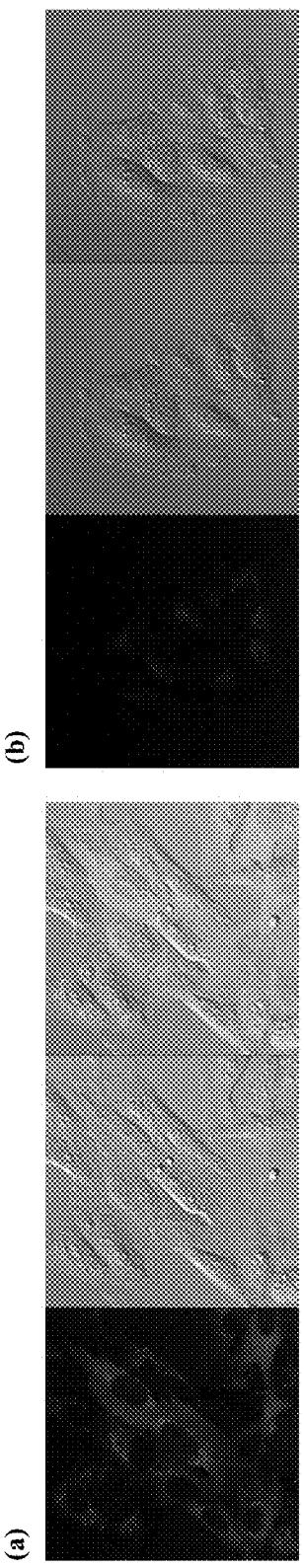
FIGS. 10(a)-10(b) shows confocal images using ligand 3781.
Figures 11A, 11B, 11C, 11D:
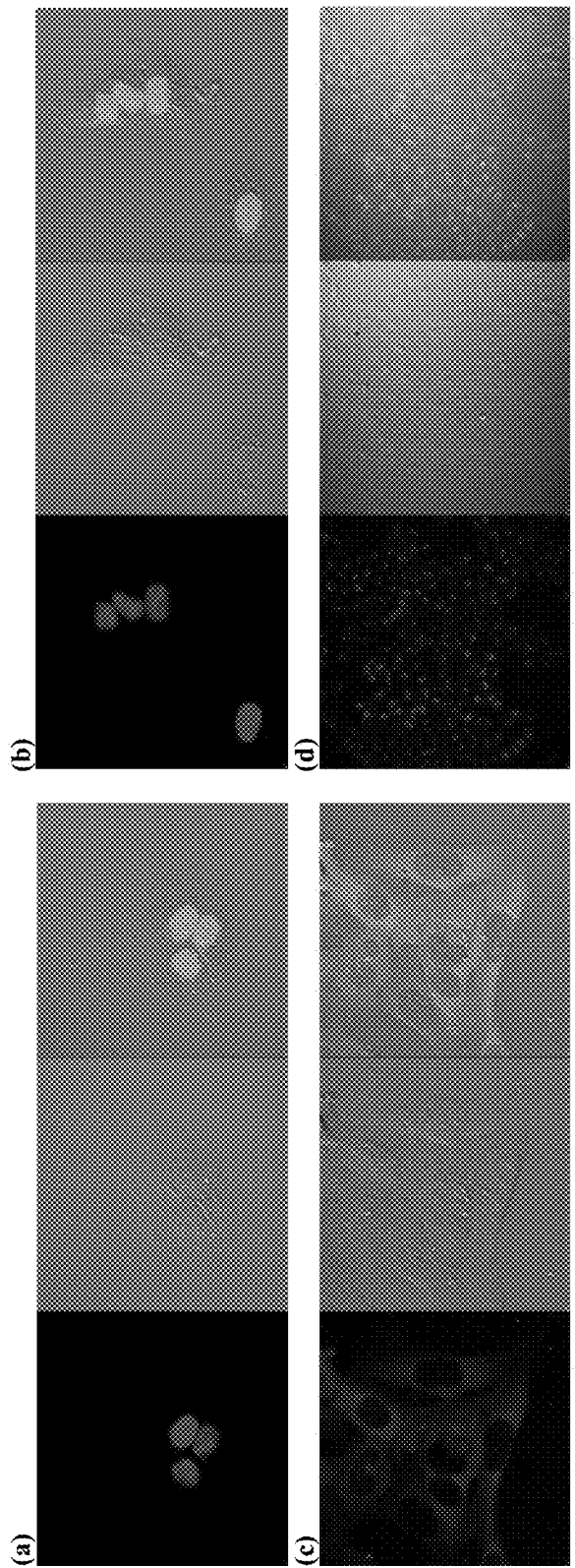
FIGS. 11(a)-11(d) shows confocal images using ligand 3782.
Figures 12A, 12B, 12C, 12D:
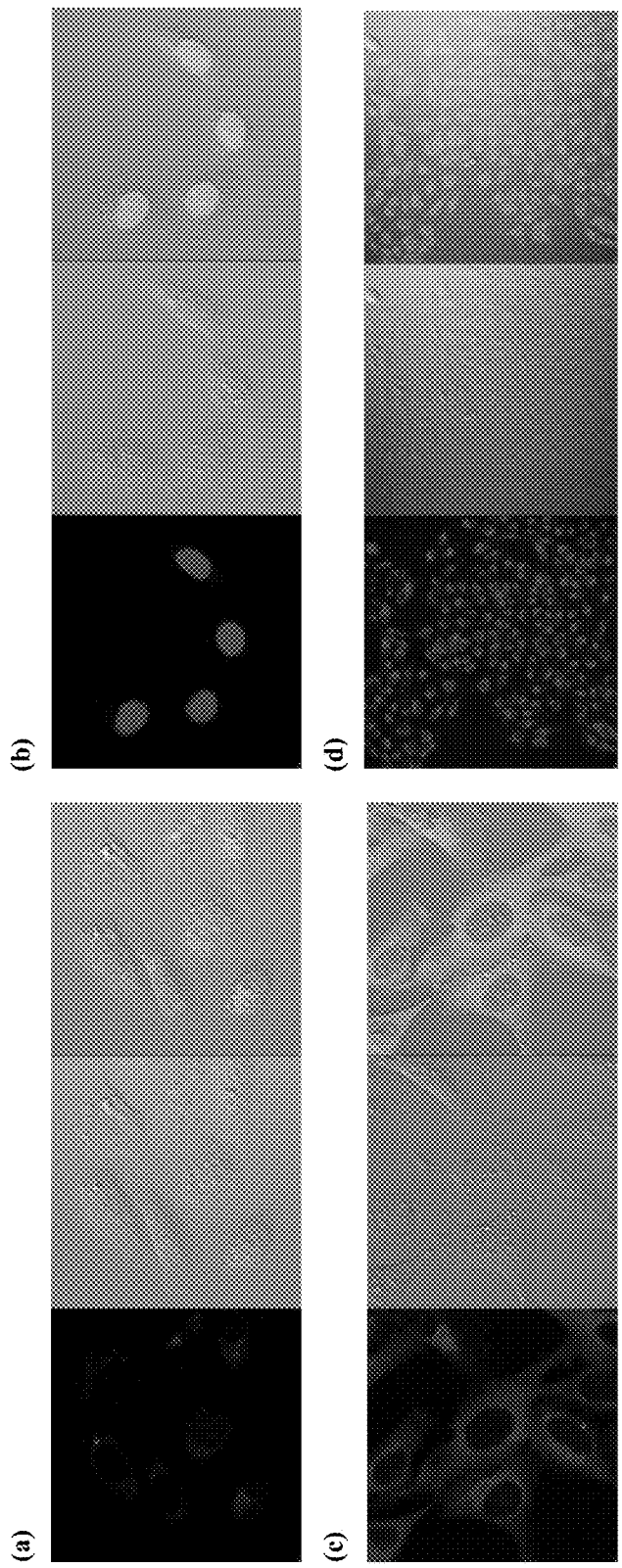
FIGS. 12(a)-12(d) shows confocal images using ligand 3783.
Figures 13A, 13B, 13C:
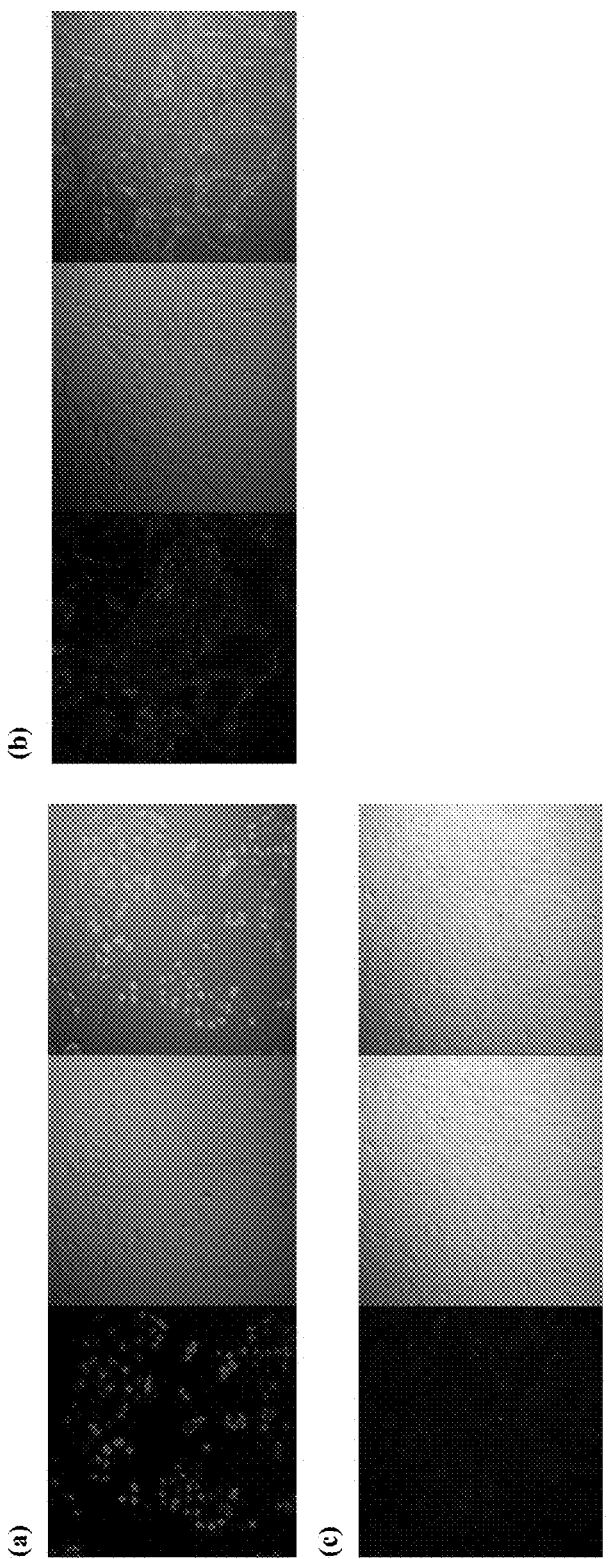
FIGS. 13(a)-13(c) shows confocal images using ligand 3905.
Figures 14A, 14B, 14C:
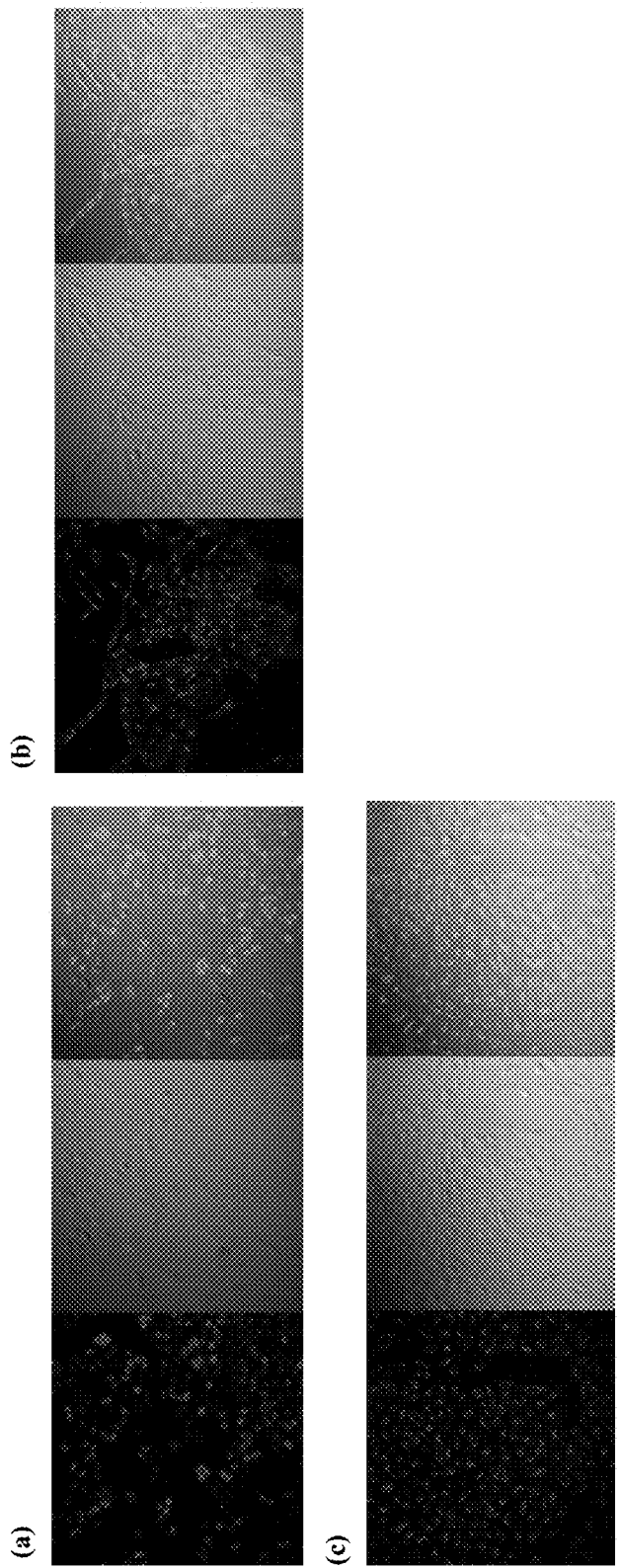
FIGS. 14(a)-14(c) shows confocal images using ligand 3906.
Figure 15A:
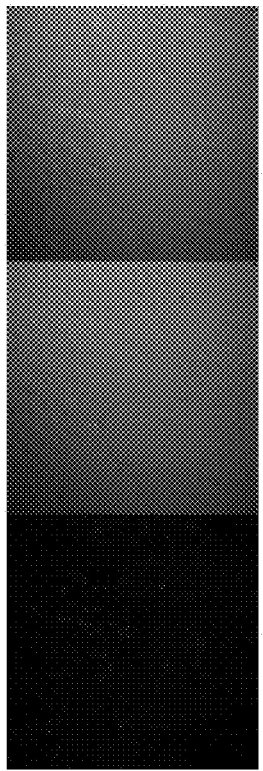
FIGS. 15(a)-15(b) shows confocal images of ligand 3954.
Figure 15B:
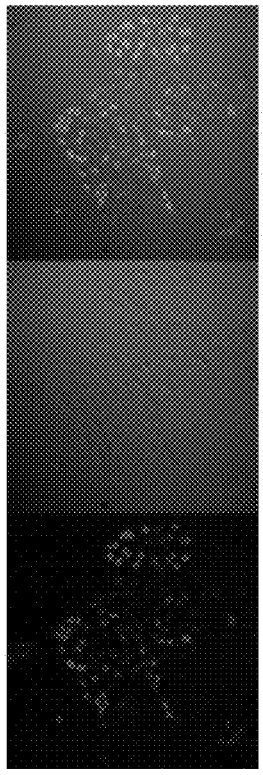
Figures 16A, 16B:
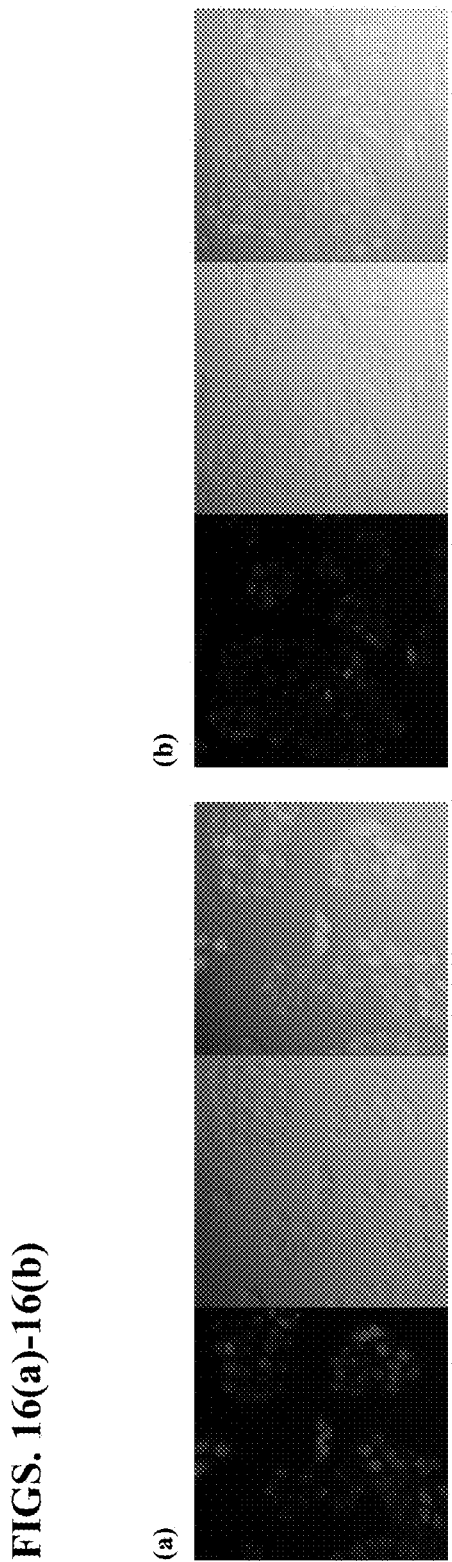
FIGS. 16(a)-16(b) shows confocal images of ligand 4356 and 4357. U2OS cells stably expressing HT-NLS were labeled with 1 μM of ligand FIG. 16(a) 4356 or FIG. 16(b) 4357 by a rapid label protocol and imaged using 10% λ633 laser, PMT 830, CA 80 μm, 30×. The left panel in each images shows fluorescence channel, the middle panel shows DIC, and the right panel shows an overlay of the two.

Suitable compounds include those shown in FIGS. 1-3. As one of ordinary skill in the art would understand, any of the combinations between column 1 and row 1 are feasible. Those that show a compound number have been synthesized.

Among other unique properties, compounds of the present invention containing a 7-membered ring show a significant red shift in the excitation and emission of the dye as compared to prior art compounds. In certain embodiments, the compounds of the present invention have emission maxima from about 600 nm to about 730 nm. In certain embodiments, the compounds of the present invention have excitation maxima from about 575 nm to about 675 nm.

Although there is no description of incorporating a fused 7-membered ring in the manner described here into a fluorescent dye in the literature, two publications (Zachariasse, et al., *J. Photochem. Photobiol. A*, 1997, 105, 373-383; Saha and Samanta, *J. Phys. Chem. A* 2002, 106, 4763-4771) describe comparisons between incorporating a nitrogen involved in dye fluorescence in a six-membered carbocyclic ring and a seven-membered carbocyclic ring. With the dyes described in these literature reports, as the ring size is increased, the quantum yield drops dramatically with increasing solvent polarity, which does not occur for the dyes of the present invention.

There has also been a discussion of the effect of unfused ring size in rosamine derivatives (Lu and Burgess, *J. Org. Chem.*, 2008, 73, 8711-8718). No shift in emission wavelength was observed on varying the ring size from a five- to a six-membered ring. The red-shifted emission of the dyes containing a fused seven-membered ring relative to those with six-membered rings while maintaining a high quantum yield in polar solvents was unanticipated.

Synthesis of Dyes

Compounds described herein may be synthesized and conjugated using a variety of methods. See, e.g., Beija, et al., *Chem. Soc. Rev.*, 2009, 38, 2410-2433. Exemplary syntheses are generalized below.

Synthesis of Dye Precursors:

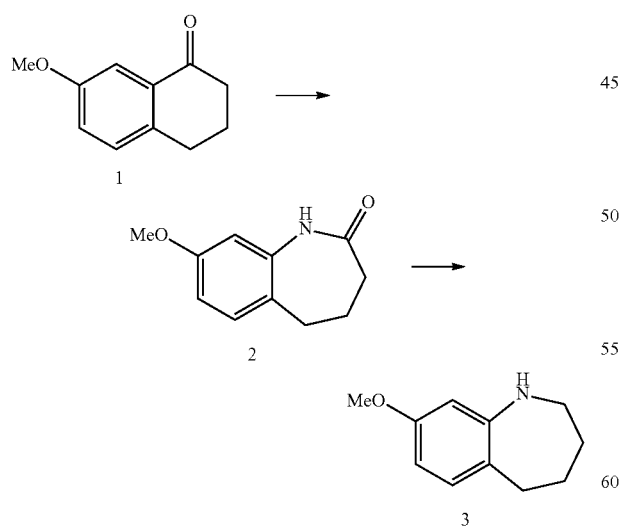

Synthesis of intermediate 3 can be done through formation of an oxime of tetralone 1 followed by a Beckmann rearrangement to give compound 2. Lactam reduction then provides compound 3.

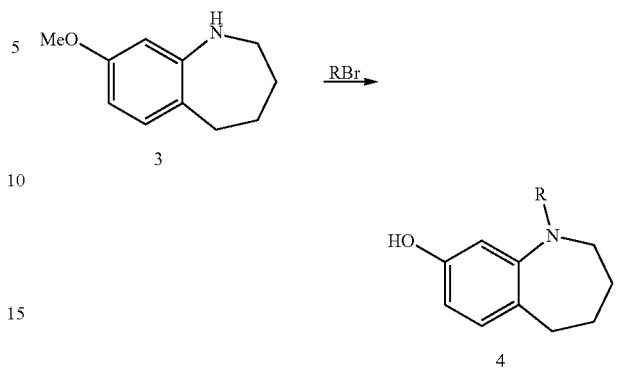

Alkylation of this cyclic amine 3 followed by demethylation provides compound 4.

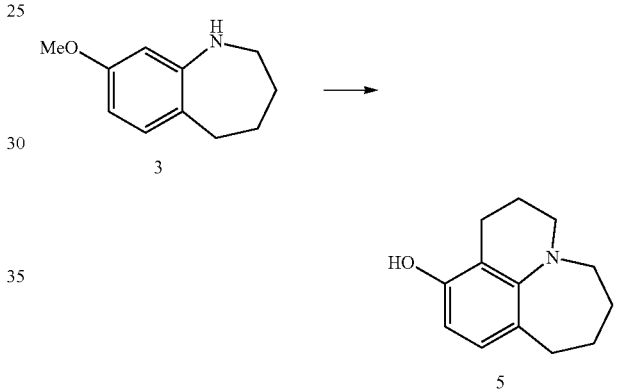

Alkylation of the nitrogen with bromochloropropane followed by heat induced cyclization provides a tricyclic amine Demethylation of this amine provides compound 5. Use of the 5-methoxy tetralone provides the isomeric aminophenol.

Synthesis of Symmetrical Dyes:

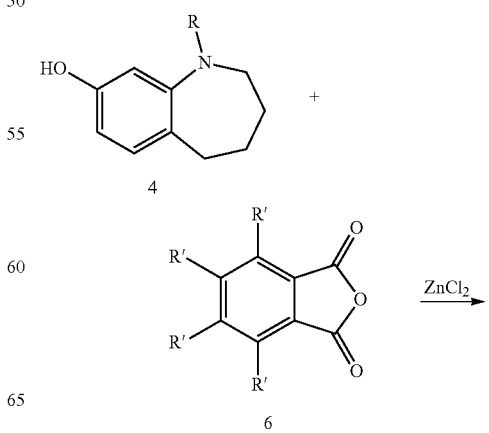

-continued

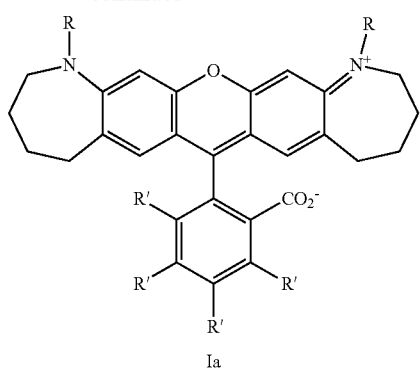

Ia

Synthesis of symmetrical rhodamines is accomplished through a melt procedure where compound 3, anhydride 6 and ZnCl$_2$ are fused together with high heat. When anhydride 6 is unsymmetrical, purification provides both isomeric dyes, typically in equal amounts. Often, some of the decarboxylated rosamine is also isolated resulting from heat induced decarboxylation of compound Ia.

Synthesis of Unsymmetrical Dyes:

Scheme 5

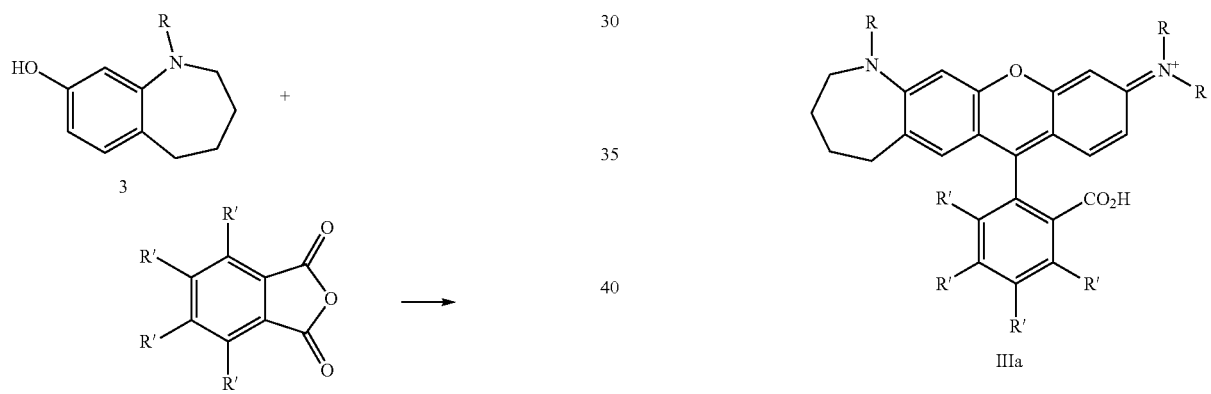

Synthesis of unsymmetrical rhodamine dyes is accomplished in a two step procedure. In the first step, an aminophenol 3 is reacted with an anhydride 6 in the absence of an acidic catalyst to provide the ketone adduct 7. As above, if 6 is unsymmetrical the two isomers of 7 can be separated at this stage.

Scheme 6

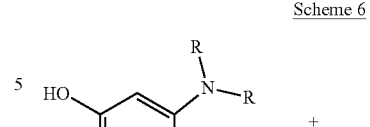

8

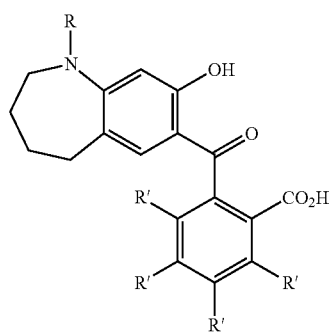

7

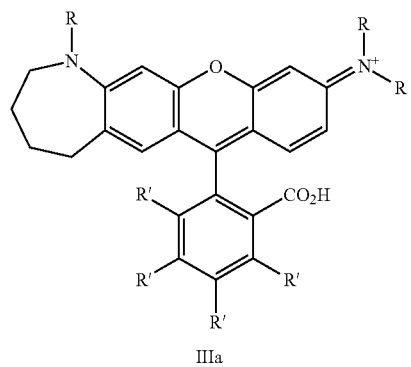

IIIa

Compound 7 is then reacted with another aminophenol (or aminonaphthol) to give a dye of formula IIIa. Typical procedure for this reaction is in DMF at 80° C. with catalytic trimethylsilylpolyphosphate.

Conjugation of Halogenated Dyes:

Scheme 7

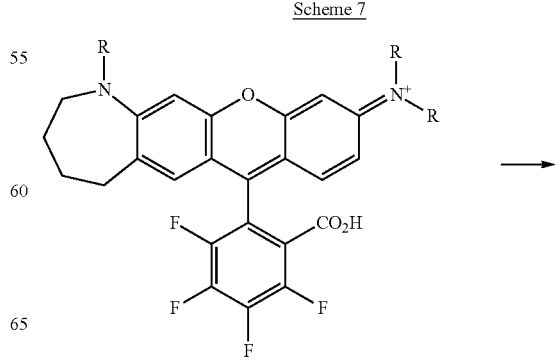

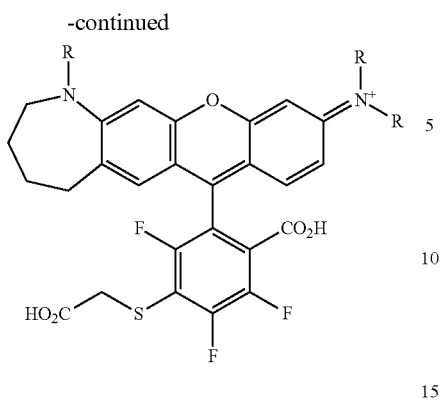

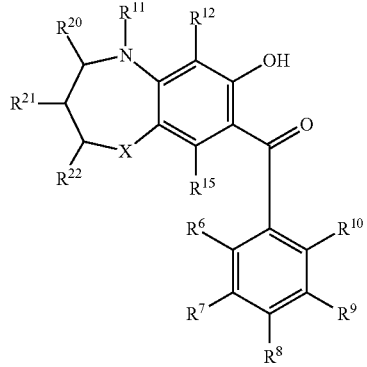

Tetrahalogenated rhodamines (either fluoro or chloro) were functionalized by treatment with mercaptoacetic acid in DMF. This carboxylic acid could then be activated as an succidimidyl ester (SE) and linked to biomolecules. Rhodamines with a carboxylic acid on the lower ring were directly activated as an SE and linked to biomolecules.

As can be appreciated by the skilled artisan, alternative methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T.W. Greene and P.G.M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Intermediates

The invention further provides compounds of formulae (VIII) and (IX):

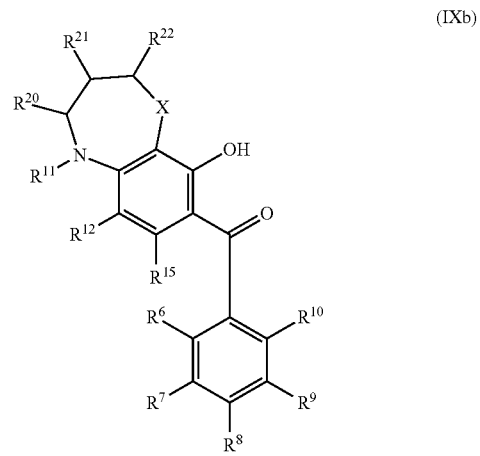

wherein $R^{11}$ is H or $C_{1-4}$ alkyl, L-R or L-$C_s$;

L is a covalent linkage that is linear or branched, cyclic or heterocyclic saturated or unsaturated, having 1-16 non hydrogen atoms such that the linkage contains any combination of ester, acid, amine, amide, alcohol, ether, thioether or halide groups or single, double, triple or aromatic carbon-carbon bond;

R is a reactive group;

$C_s$ is a conjugated substance;

$R^{12}$ and $R^{15}$ are independently H, alkyl, aryl, $CO_2H$, $SO_3H$, L-$CO_2H$, L-$SO_3H$, L-R or L-$C_s$;

$R^{20}$, $R^{21}$, $R^{22}$ and $R^{23}$ are independently H or $C_{1-6}$ alkyl or one or more of $R^{20}$ and $R^{21}$, $R^{21}$ and $R^{22}$ and $R^{22}$ and $R^{23}$ together form a fused aryl ring;

$R^{11}$ and $R^{12}$ may be joined together in an optionally substituted ring;

$R^{6-10}$ are independently H, F, Cl, Br, I, OH, alkyl, aryl, $CO_2H$, $SO_3H$, L-$CO_2H$, L-$SO_3H$, L-R or L-$C_s$;

X is $CHR^{23}$, O, S or $NR^{30}$; and $R^{30}$ is H, $C_{1-4}$ alkyl or —C(O)$C_{1-4}$ alkyl.

In some embodiments, the ring formed by $R^{11}$ and $R^{12}$ can be from 3-10 atoms chosen from C, N, O and S. These rings may contain elements of unsaturation as well.

These compounds are useful in the synthesis of compounds of formulae (I)-(VII).

Labeled Biomolecules

Briefly, the dyes of the present invention may be used as labeling agents which allow for the detection of a composition of matter. The dyes of the present invention can be used to label a broad range of molecules, including but not limited to, biomolecules such as polypeptides, polypeptide-based toxins, amino acids, nucleotides, polynucleotides including DNA and RNA, lipids, carbohydrate, and enzyme substrates. Additionally, the compounds may be used to label haptens, small molecules, drugs, drug compounds, ion-complexing agents, such as metal chelators, microparticles, synthetic or natural polymers, cells, viruses, other fluorescent molecules or surfaces. The resulting labeled molecules may be referred to as conjugates or tracers.

In some aspects, the dyes can be conjugated with a nucleoside, nucleotide or a polynucleotide. The dyes of the invention may be conjugated with nucleoside, nucleotide or polynucleotide in any way known to one of ordinary skill in the art such as through a phophoramidite, an activated ester or a reactive platinum complex.

In other aspects, the dyes of the invention can be used to conjugate with an amino acid, amino acid analog, or polypeptide. In other aspects, the dyes of the invention can be used to conjugate with a small molecule, e.g., a drug or drug compound. In some aspects, the conjugated small molecule can be used as a fluorescent tracer.

In some embodiments, the labeled biomolecules may be profluorescent compounds. A profluorescent compound is one that has a fluorescence that is reduced as compared to the related dye and contains a substrate for an enzyme of interest. Upon being acted on by the enzyme of interest, the fluorescent dye from the profluorescent compound is released, and thereby fluorescence is generated. A "traceless" or "self-immolative" linker can also be included between the dye and the enzyme substrate.

Exemplary labeled biomolecules include compounds of formulae (XIa), (XIb) and (XIc):

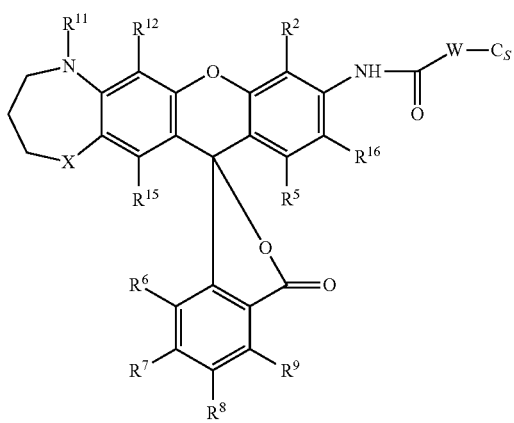
(XIa)

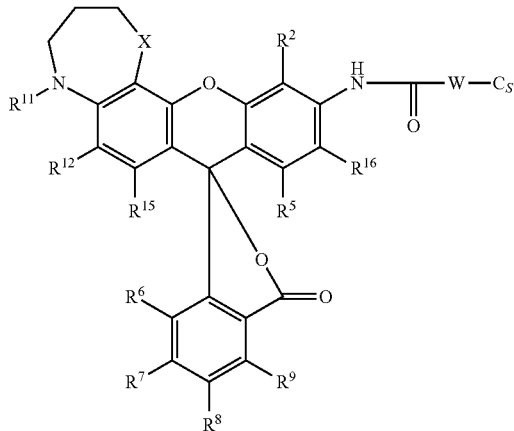
(XIb)

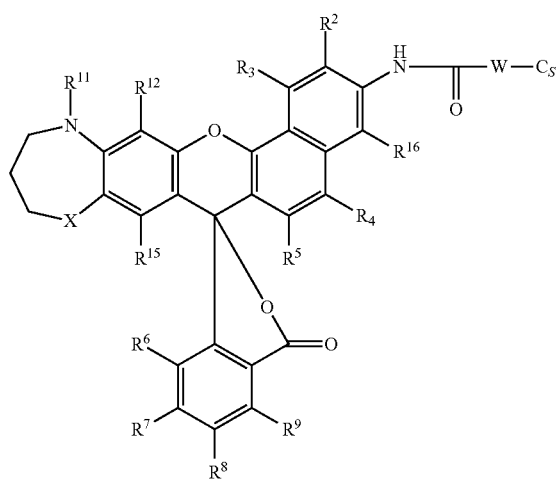
(XIc)

wherein $R^{11}$ is H or $C_{1-6}$ alkyl;

W is a traceless linker or a direct bond;

R is a reactive group;

$C_s$ is an enzyme substrate;

$R^2$, $R^3$, $R^4$ $R^5$, $R^{11}$, $R^{12}$, $R^{13}$, $R^{14}$, $R^{15}$ and $R^{16}$ are independently H, alkyl, aryl, $CO_2H$, $SO_3H$, L-R, L-$C_s$, L-$CO_2H$, or L-$SO_3H$;

$R^{11}$ and $R^{12}$ may be joined together in an aryl, heteroaryl, carbocyclic or heterocyclic ring;

$R^{6-9}$ are independently H, F, Cl, Br, I, OH, alkyl, aryl, $CO_2H$, $SO_3H$, L-$CO_2H$, or L-$SO_3H$; and X is $CH_2$, O, S or NH.

In some embodiments, the enzyme substrate is Z-DEVD. In another embodiment, the enzyme substrate is Z-AAF-benzyl.

Profluorescent compounds according to formulae (XIa) include:

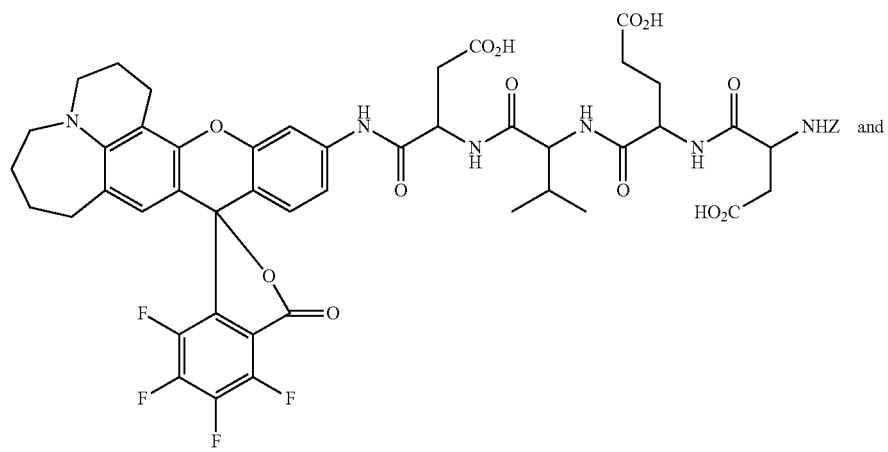

Z-DEVD-TOM
Caspase-3 substrate

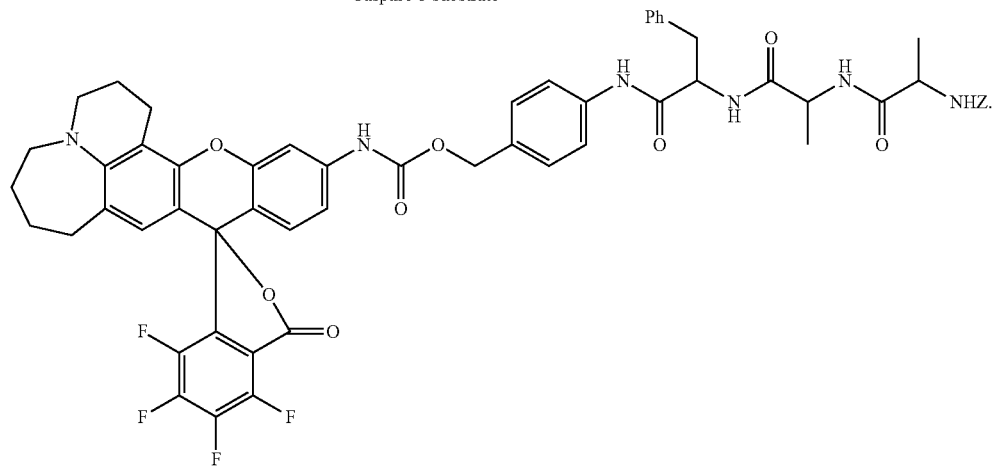

Z-AAF-benzylITOM
Dead cell protease substrate

In other embodiments, the invention provides other profluorescent biomolecules. In some embodiments, a dye according to the present invention is attached through a biomolecule to a quencher. Any quencher that absorbs in the emission spectrum of the dye can be used. One of ordinary skill in the art would be able to identify such quenchers. Suitable quenchers include Black Hole Quenchers™ and QXL™ quenchers. (Available from Life Technologies).

Exemplary profluorescent compounds containing a quencher include: Quencher-GABA-Pro-Cha-Abu-Smc-His-Ala-Dab(dye)-Ala-Lys-NH2 as an MMP-3 substrate where cleavage in the amino acid chain separates the quencher from the dye, producing fluorescence. In one embodiment, the dye can be conjugated to the amino acid chain through a carboxylic acid in the lower ring. The dye can also be attached to the amino acid chain at other positions.

Methods of Use

The dyes of the present invention provide an effective tool for covalently labeling biomolecules for a wide variety of applications. Labeling allows one to study interactions involving biomolecules such as proteins, glycoproteins, nucleic acids and lipids, as well as small molecules, e.g., drugs or drug compounds, inorganic chemicals or any combinations thereof. The interactions may be studied in cell-free biological systems, in cellular systems or in vivo. Analyzing the various interactions is often a significant part of scientific research and development, drug design, screening and optimization, phylogenetic classification, genotyping individuals, parental and forensic identification, environmental studies, diagnosis, prognosis, and/or treatment of disease conditions.

In some aspects of the invention, the conjugates of the invention are used to label a sample so that the sample can be identified or quantitated. For instance, such conjugates may be added as part of an assay for a biological target analyte or as a detectable tracer element in a biological or non-biological fluid.

The sample may be obtained directly from biological materials, e.g., a wash from a solid material (organic or inorganic), a medium in which cells have been cultured, a cell lysate, a buffer solution in which cells have been placed for evaluation, or physiological sources, e.g., blood, plasma, serum, urine, etc. When the sample comprises cells, the cells are optionally single cells, including microorganisms, or multiple cells associated with other cells in two or three dimensions, including multicellular organisms, embryos, tissues, biopsies, filaments, biofilms, and the like. When the sample comprises cells, the cells may be lysed, e.g., a cell lysate, or whole cells.

Alternatively, the sample is a solid, optionally a smear or scrape or a retentate removed from a liquid or vapor by filtration. In one aspect of the invention, the sample is obtained from a biological fluid, including separated or unfiltered physiological fluids such as urine, cerebrospinal fluid, blood, lymph fluids, tissue homogenate, interstitial fluid, cell extracts, mucus, saliva, sputum, stool, physiological secretions or other similar fluids. Alternatively, the sample is obtained from an environmental source such as soil, water, or air; or from an industrial source such as taken from a waste stream, a water source, a supply line, or a production lot.

In other embodiments, the sample is present on or in a solid or semi-solid matrix. In one aspect of the invention, the matrix is a membrane. In other aspects, the matrix is an electrophoretic gel, such as those used for separating and characterizing nucleic acids or proteins, or a blot prepared by transfer from an electrophoretic gel to a membrane. In other aspects, the matrix is a silicon chip or glass slide, and the analyte of interest has been immobilized on the chip or slide in an array (e.g., the sample comprises proteins or nucleic acid polymers in a microarray). In yet other aspects, the matrix is a microwell plate or microfluidic chip, and the sample is analyzed by automated methods, typically by various methods of high-throughput screening, such as drug screening.

The dye conjugates are generally utilized by combining the conjugate as described above with the sample of interest under conditions selected to yield a detectable optical response. The sample is then illuminated at a wavelength selected to elicit the optical response. Typically, a specified characteristic of the sample is determined by comparing the optical response with a standard or expected response.

A detectable optical response means a change in, or occurrence of, an optical signal that is detectable either by observation or instrumentally. Typically, the detectable response is a change in fluorescence, such as a change in the intensity, excitation or emission wavelength distribution of fluorescence, fluorescence lifetime, fluorescence polarization, or a combination thereof. The degree and/or location of the labeling, compared with a standard or expected response, indicates whether, and to what degree, the sample possesses a given characteristic. Some dyes of the invention may exhibit little fluorescence emission, but are still useful as chromophoric dyes. Such chromophores are useful as energy acceptors in FRET applications, or to simply impart the desired color to a sample or portion of a sample.

For biological applications, the dye conjugates are typically used in an aqueous, mostly aqueous or aqueous-miscible solution prepared according to methods generally known in the art. The exact concentration of the dye compound is dependent upon the experimental conditions and the desired results, but typically ranges from about one nanomolar to one millimolar or more. The optimal concentration may be determined by systematic variation until satisfactory results, with minimal background fluorescence, are accomplished.

The dye conjugates may be used to label samples containing biological components. The sample may comprise heterogeneous mixtures of components (including intact cells, cell extracts, cell lysates, bacteria, viruses, organelles, and mixtures thereof) or a single component or homogeneous group of components (e.g., natural or synthetic amino acid, nucleic acid or carbohydrate polymers, or lipid membrane complexes). The dyes are generally non-toxic to living cells and other biological components within the concentrations of use.

The dye conjugate may be combined with the sample in a way that facilitates contact between the dye conjugate and the sample components of interest. Typically, the dye conjugate or a solution containing the dye conjugate is simply added to the sample. Certain dyes of the invention, e.g., those that are substituted by one or more sulfonic acid moieties, may be less permeant to membranes of biological cells, but once inside viable cells are typically well retained. Treatments that permeabilize the plasma membrane, such as electroporation, shock treatments or high extracellular ATP, may be used to introduce selected dye conjugates into cells. Alternatively, selected dye conjugates can be physically inserted into cells, e.g., by pressure microinjection, scrape loading, patch clamp methods, or phagocytosis.

Dyes that incorporate an aliphatic amine or a hydrazine residue may be microinjected into cells where they can be fixed in place by aldehyde fixatives such as formaldehyde or glutaraldehyde. This property makes such dyes useful for intracellular applications such as neuronal tracing.

Dyes that possess a lipophilic substituent, such as phospholipids, may non-covalently incorporate into lipid assemblies, e.g., for use as probes for membrane structure, or for incorporation in liposomes, lipoproteins, films, plastics, lipophilic microspheres or similar materials; or for tracing. Lipophilic dyes are useful as fluorescent probes of membrane structure.

Chemically reactive dye compounds may covalently attach to a corresponding functional group on a wide variety of materials to form dye conjugates as described above. Using dye compounds to label reactive sites on the surface of cells, in cell membranes, in intracellular compartments such as organelles, or in the cytoplasm, permits the determination of their presence or quantity, accessibility, activity or their spatial and temporal distribution in the sample. Photoreactive dyes may be used similarly to photolabel components of the outer membrane of biological cells or as photo-fixable polar tracers for cells.

In some embodiments, chloroalkane-labeled dyes may be used with HaloTag® protein to detect proteins of interest by generating a fusion protein between the HaloTag® protein and the protein of interest. Generally, these fusion proteins are expressed by a cell from a HaloTag® fusion construct, and the fusion protein is detected through use of the chloroalkane-labeled dye. This allows detection of protein expression or determination of a protein expression timecourse, protein localization or migration. In addition, these proteins can be detected in gels using this fluorescent label. The dyes may also be utilized in other orthogonal labeling systems, such as cutinase, dihydrofolate reductase/trimethoprim SNAP-tag, Clip Tag, Alkyl cytosine transferase (see U.S. Patent Application No. 2012/0237961, which is incorporated by reference herein) and Acyl Carrier Protein (see U.S. Patent Application No. 2010/0173384, which is incorporated by reference herein). In addition, HaloTag is also orthogonal to other labeling chemistries such as Hsuingen cyclizations (click chemistry), hydrazone and oxime formation and the Staudinger ligation.

Optionally, the sample is washed after labeling to remove residual, excess or unbound dye compound or dye conjugate. The sample is optionally combined with one or more other solutions in the course of labeling, including wash solutions, permeabilization and/or fixation solutions, and solutions containing additional detection reagents. An additional detection reagent typically produces a detectable response due to the presence of a specific cell component, intracellular substance, or cellular condition, according to methods generally known in the art. When the additional detection reagent has, or yields a product with, spectral properties that differ from those of the subject dye compounds, multi-color applications are possible. This is particularly useful where the additional detection reagent is a dye or dye conjugate having spectral properties that are detectably distinct from those of the labeling dye.

The dye conjugates are used according to methods known in the art, e.g., use of antibody conjugates in microscopy and immunofluorescent assays; or nucleotide or oligonucleotide conjugates for nucleic acid hybridization assays, nucleic acid amplification reactions, and nucleic acid sequencing (e.g., U.S. Pat. Nos. 5,332,666, 5,171,534, and 4,997,928, and WO 94/05688). Dye conjugates of multiple independent dyes of the invention possess utility for multi-color applications.

At any time after or during labeling, the sample is illuminated with a wavelength of light selected to give a detectable optical response and observed with a means for detecting the optical response. Equipment that is useful for illuminating the dye compounds of the invention includes, but is not limited to, hand-held ultraviolet lamps, mercury arc lamps, xenon lamps, lasers and laser diodes. These illumination sources are optionally integrated into laser scanners, fluorescence microplate readers, standard or mini-fluorometers, or chromatographic detectors.

The optical response is optionally detected by visual inspection or by use of any of the following devices: CCD cameras, video cameras, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

Exemplary Methods of Use i. Detection of Nucleic Acid Polymers

In one embodiment, a dye oligonucleotide conjugate of the present invention is combined with a sample that contains, or is thought to contain, a nucleic acid polymer, incubating the mixture of dye oligonucleotide conjugate, e.g., probe or primer, and sample for a time sufficient for the oligonucleotide in the conjugate to combine with nucleic acid polymers in the sample to form nucleic acid hybrids (complexes) (i.e., a probe), or to prime nucleic acid synthesis (i.e., a primer), which may be detected. The characteristics of the labeled molecules, including the presence, location, intensity, excitation and emission spectra, fluorescence polarization, fluorescence lifetime, and other physical properties of the fluorescent signal, can be used to detect, differentiate, sort, quantitate, sequence and/or analyze aspects or portions of the sample. The dye conjugates of the invention are optionally used in conjunction with one or more additional reagents (e.g., detectably different fluorescent reagents) including dyes of the same class having different spectral properties.

Typically, the dye conjugate is prepared for use by dissolving the dye conjugate in an aqueous or aqueous miscible solution that is compatible with the sample and intended use. For biological samples, where minimal perturbation of cell morphology or physiology is desired, the solution is selected accordingly.

The labeling solution is made by dissolving the dye conjugate directly in an aqueous solvent such as water, a buffer solution, such as buffered saline (preferably non-phosphate for some viability discrimination applications), a Tris(hydroxymethyl)-aminomethane (TRIS) buffer (preferably containing EDTA), or a water-miscible organic solvent such as dimethylsulfoxide (DMSO), dimethylformamide (DMF), or a lower alcohol such as methanol or ethanol. The dye conjugate is usually preliminarily dissolved in an organic solvent (e.g., 100% DMSO) at a concentration of greater than about 100 times that used in the labeling solution, then diluted one or more times with an aqueous solvent such as water or buffer, such that the dye conjugate is present in an effective amount.

Typically labeling solutions for cellular samples have a dye concentration greater than 0.1 nM and less than 50 µM, more typically greater than 1 nM and less than 10 µM, e.g., between 0.5 and 5 µM. Labeling solutions for electrophoretic gels typically have a dye concentration of greater than 0.1 µM and less than 10 µM, more typically about 0.5 to 2 µM. The same holds true when the dye is added to the gel before being combined with nucleic acids. Labeling solutions for detection and quantitation of free nucleic acids in solution typically have a concentration of 0.1 µM to 2 µM. The optimal concentration and composition of the labeling solution is determined by the nature of the sample (including physical, biological, biochemical and physiological properties), the nature of the dye-sample interaction (including the transport rate of the dye to the site of the nucleic acids), and the nature of the analysis being performed, and can be determined according to standard procedures.

The nucleic acid in the sample may be DNA or RNA, or a mixture or a hybrid thereof. Any DNA is optionally single-, double-, triple-, or quadruple-stranded DNA; any RNA is optionally single stranded ("ss") or double stranded ("ds"). The nucleic acid may be a natural polymer (biological in origin) or a synthetic polymer (modified or prepared artificially). The nucleic acid polymer (for instance, one containing at least 8 bases or base pairs) may be present as nucleic acid fragments, oligonucleotides, or larger nucleic acid polymers with secondary or tertiary structure. The nucleic acid is optionally present in a condensed phase such as a chromosome. The nucleic acid polymer optionally contains one or more modified bases or links or contains labels that are non-covalently or covalently attached. For example, the modified base can be a naturally occurring modified base such as Ψ (pseudouridine) in tRNA, 5-methylcytosine, 6-methylaminopurine, 6-dimethylaminopurine, 1-methylguanine, 2-methylamino-6-hydroxypurine, 2-dimethyl-amino-6-hydroxypurine, 5-amino-DU, isoC, isoG, or other known minor bases (see, e.g., Davidson, The Biochemistry Of The Nucleic Acids (1976)) or is synthetically altered to contain an unusual linker such as morpholine derivatized phosphates (AntiVirals, Inc., Corvallis, Oreg.), or peptide nucleic acids such as N-(2-aminoethyl)glycine units (Wittung et al., Nature, 368:561 (1994)) or contain a simple reactive functional group (<10 carbons) that is an aliphatic amine, carboxylic acid, alcohol, thiol or hydrazine, or contain a fluorescent label or other hapten, such as inosine, bromodeoxyuridine, iododeoxyuridine, biotin, digoxigenin, 2,4-dinitrophenyl, where the label is originally attached on the nucleotide (e.g., CHROMATIDE™ labeled nucleotides, Molecular Probes, Eugene, Oreg.) or located on the 3' or 5' end of a nucleic acid polymer, or ligands non-covalently attached to the nucleic acids. The sensitivity of the dyes for nucleic acid polymers containing primarily modified bases and links may be diminished by interference with the binding mode. Some embodiments of the dyes may inhibit non-specific nuclease activity but not restriction endonuclease activity at certain dye:base pair ratios.

The sample that contains a nucleic acid is optionally a biological structure (i.e., an organism or a discrete unit of an organism), or a solution (including solutions that contain biological structures), or a solid or semi-solid material. Consequently, the nucleic acid is optionally free in solution, immobilized in or on a solid or semi-solid material, extracted from a biological structure (e.g., from lysed cells, tissues, organisms or organelles), or remains enclosed within a biological structure. In order for the nucleic acids to bind to the dyes, it is necessary that the nucleic acids be in an aqueous environment to allow contact with the dye, even if the nucleic acids are not enclosed in a biological structure.

The biological structure that contains the nucleic acid is optionally a cell or tissue, for example, where the nucleic acid is present in a cell or interstitial space, as a prokaryote or eukaryote microorganism, or as a virus, viroid, chromosome or organelle. Alternatively, the biological structure may not be contained in a tissue or cell and is present either as a virus or as a microorganism or other cell, or is present as a cellular component removed from its parent cell (e.g., a plasmid or chromosome, or a mitochondrion or nucleus or other organelle). Typically, the biological structure is an organelle, chromosome or cell that is optionally contained within a eukaryote cell. The cell present inside a eukaryote cell is typically a parasite or other infectious agent such as a virus, bacterium, protozoa, mycoplasma or mycobacterium. When the nucleic acid is contained in a biological structure that is a cell, the cells are viable or dead cells or a mixture thereof, i.e., the integrity of the cell membrane is optionally intact or disrupted by natural (autolytic), mechanical or chemical means or by environmental means such as changes in temperature or pressure. Alternatively, the cells are blebbing or undergoing apoptosis or in a cycle of growth or cell division.

When the nucleic acid is present in a solution, the sample solution can vary to contain one of purified or synthetic nucleic acids such as oligonucleotides to crude mixtures such as cell extracts or homogenates or other biological fluids, or dilute solutions from biological, industrial, or environmental sources. In some cases, it is desirable to separate the nucleic acids from a mixture of biomolecules or fluids in the solution prior to combination with the dye. Numerous techniques exist for separation and purification of nucleic acids from generally crude mixtures with other proteins or other biological molecules. These include such means as chromatographic techniques and electrophoretic techniques using a variety of supports or solutions or in a flowing stream. Alternatively, mixtures of nucleic acids may be treated with RNase or DNase so the nucleic acid polymer is not degraded in the presence of the nuclease can be discriminated from degradation products using the subject dyes.

The relatively low toxicity of the dyes of the invention to living systems generally enables the examination of nucleic acids in living samples with little or no damage caused by the dye itself. For use with intact cells or samples in a gel, more permeant dyes may be employed, although some cells readily take up dyes that have been shown to be impermeant to other cells by means other than passive diffusion across cell-membranes, e.g., by phagocytosis or other types of ingestion. These dyes can be used in standard gel-based applications. The photostability, toxicity, binding affinity, quantum yield, and fluorescence enhancement of dyes are determined according to standard methods known in the art.

In one embodiment, a dye oligonucleotide conjugate, e.g., probe or primer, is employed in methods and kits for the identification of alleles in a physiological sample. In one embodiment, an appropriate set of loci, primers, and amplification protocols is selected to generate amplified alleles from multiple co-amplified loci which, in one embodiment, do not overlap in size or which are labeled in a way which enables one to differentiate between the alleles from different loci which overlap in size. In addition, this method contemplates the selection of short tandem repeat (STR) loci which are compatible for use with a single amplification protocol. Successful combinations can be generated by trial and error of locus combinations, by selection of primer pair sequences, and by adjustment of primer concentrations to identify an equilibrium in which all included loci may be amplified. The number of loci which may be amplified in a multiplex amplification reaction step may be from 2 to 50, or any integer between 2 and 50, e.g. 16, 17, 18, 21, 23, or 26, so long as the reaction produces amplified alleles that can be identified. In one embodiment, the amplified fragments are less than 500 bp in length.

Synthesis of the primers used in the present method can be conducted using any standard procedure for oligonucleotide synthesis known to those skilled in the art. At least one primer for each locus is covalently attached to a different dye label.

Samples of genomic DNA can be prepared for use in the method of this invention using any method of DNA preparation which is compatible with the amplification of DNA. Many such methods are known by those skilled in the art. When the at least one DNA sample to be analyzed is human genomic DNA, the DNA may be prepared from samples, selected from the group consisting of tissue, blood, semen, vaginal cells, hair, saliva, urine, bone, buccal samples, amniotic fluid containing placental cells or fetal cells, chorionic villus, and mixtures of any of the samples listed above.

Once a sample of genomic DNA is prepared, the targeted loci can be co-amplified in the multiplex amplification step. Any one of a number of different amplification methods can be used to amplify the loci, including, but not limited to, polymerase chain reaction (PCR), transcription based amplification and strand displacement amplification (SDA). In one embodiment, the DNA sample is subjected to PCR amplification using primer pairs specific to each locus in the set.

At least one primer for each locus can be covalently attached to a dye label, one of which comprises a dye of the present invention. The primers and dyes attached thereto are selected for use in the multiplex amplification reaction such that the alleles amplified using primers for each locus labeled with one color do not overlap with the alleles of the other loci in the set co-amplified therein using primers labeled with the same color, when the alleles are separated, e.g., by gel or capillary electrophoresis. Fluorescent labels suitable for attachment to primers for use in the present invention are commercially available. See, e.g. fluorescein and carboxy-tetramethylrhodamine labels and their chemical derivatives from PE Biosystems and Molecular Probes. In one embodiment, at least three different labels are used to label the different primers used in the multiplex amplification reaction. When a size marker is included to evaluate the multiplex reaction, the primers used to prepare the size marker may be labeled with a different label from the primers used to amplify the loci of interest in the reaction.

Once a set of amplified alleles is produced from the multiplex amplification step, the amplified alleles are evaluated. The evaluation step of this method can be accomplished by any one of a number of different means. Electrophoresis may be used to separate the products of the multiplex amplification reaction, e.g., capillary electrophoresis or denaturing polyacrylamide gel electrophoresis. Gel preparation and electrophoresis procedures and conditions for suitable for use in the evaluating step are known to the art. Separation of DNA fragments in a denaturing polyacrylamide gel and in capillary electrophoresis occurs based primarily on fragment size.

Once the amplified alleles are separated, the alleles and any other DNA in the gel or capillary (e.g., DNA size markers or an allelic ladder) can then be visualized and analyzed. In one embodiment, the method for detection of multiplexes containing numerous loci is fluorescence, where primers for each locus in the multiplexing reaction is followed by detection of the labeled products employing a fluorometric detector.

ii. Cell Imaging

Fluorescently-labeled biomolecules have proven extremely useful as reporters for gene expression studies in both cultured cells and entire animals. For example, in living cells, fluorescently-labeled proteins are most commonly utilized to track the localization and dynamics of proteins, organelles, and other cellular compartments, as well as a tracer of intracellular protein trafficking. Quantitative imaging of labeled biomolecules according to the present invention is readily accomplished with a variety of techniques, including widefield, confocal, and multiphoton microscopy and provides a unique window for exposing the intricacies of cellular structure and function. Among other things, the dyes of the present invention can be used to image subcellular protein translocation, to detect protein-protein and protein-DNA complexes, and to determine protein expression, localization and activity state.

In one embodiment, the cell is contacted with a labeled biomolecule according to the present invention, and fluorescence is detected. For example, a protein can be labeled with a dye of the present invention and used to bind to a cell surface receptor. In this example, the location of the cell surface receptor can be detected.

Alternatively, fluorescent dyes according to the present invention can be used in a modular protein tagging system such as HaloTag® protein (Promega, Madison Wis.). In this type of system, the protein tag is a modified haloalkane dehalogenase designed to covalently bind to a synthetic ligand which has a chloroalkane linker attached to a fluorescent dye according to the present invention.

iii Enzyme Assays

The dyes of the present invention can also be conjugated to enzyme substrates and used to detect the presence and/or activity of an enzyme in a sample. Thus, the invention provides a method of detecting an enzyme in a sample. In one embodiment, a sample suspected of containing an enzyme is contacted with a labeled biomolecule which is a profluorescent form of a dye of the present invention and a substrate for the enzyme; and fluorescence is detected.

iv. Other Uses

The fluorescent dyes of the present invention can be used in other techniques known to those skilled in the art. For example, the dyes may be used in antibody staining, in studies of organometallic catalysis in living cells, in biomedical imaging, in in vivo detection of small molecules, thiol-reactive probes, biotin and hapten derivatives, nucleic acid and protein analysis, for probing cellular structure (including cytoskeletal proteins, organelles, lipids and membranes and as fluorescent tracers of cell morphology and fluid flow), and for probing cellular function (including cell viability, cell proliferation, endocytosis, receptors, ion channels, signal transduction, ROS, various cations, and membrane potential). The dyes may also be used to detect biological phenomena using FRET or BRET. See, e.g. "The Molecular Probes® Handbook" (www.invitrogen.com) for a description of various uses for the dyes of the present invention.

The dyes may also be used to detect biological phenomena using fluorescent resonance energy transfer FRET or bioluminescence resonance energy transfer (BRET). See, e.g. "The Molecular Probes® Handbook" (www.invitrogen.com) for a description of various uses for the dyes of the present invention. In some embodiments, the dyes disclosed herein can be used as BRET acceptors. If a dye described herein is brought within the energy transfer radius (e.g., typically <10 nm) of a luciferase and is in the correct orientation, radiationless energy transfer will occur, and the dye will emit light at its normal emission. There are many methods known for bringing the dye close to a luciferase, e.g., small molecules or quantum dots (Xia, Z and Rao, J. 2009. Curr. Opin. Biotech 20: 37-44), and these methods enable one to learn something about a biological system of interest.

In some embodiments, a dye disclosed herein may be conjugated to a tag such as a chloroalkane (see U.S. Pat. No. 7,867,726). This conjugation causes the dye to be strongly associated to a protein of interest in a cell or cell lysate if that protein is expressed as a HaloTag® fusion. Such a fusion of a protein of interest and HaloTag protein would be covalently labeled with the dye conjugate. There are many other methods of associating a dye disclosed herein with a specific protein, such as conjugating the dye to a specific antibody. Another protein of interest in the cell or cell lysate can then be fused to a luciferase such as a firefly luciferase or Oplophorus luciferase, e.g., NanoLuc™ luciferase from Promega Corporation (see U.S. 20100281552 and U.S. Ser. No. 13/287,986). Upon addition of a luciferin substrate, BRET would be observed if the first and second proteins of interest interact at a defined distance (e.g., typically <10 nm). Such a system allows one to study the interaction of two specific proteins under various conditions, e.g., inside of a living cell.

In some embodiments, the use of a dye disclosed herein in FRET or BRET can be used to ascertain the biological interaction of any two materials of interest such as nucleic acids, lipids, polysaccharides, antibodies, small molecules, e.g. drugs or drug compounds, etc. In some embodiments, the interaction of a small molecule with a protein occurs inside of a living cell. In some embodiments, a dye disclosed herein may be conjugated to a small molecule, e.g., a tracer, that binds to a protein of interest in such a way that the molecule/protein interaction is not disturbed by the dye conjugation. If the protein of interest is expressed as a luciferase fusion as described above, the interaction of the small molecule with the protein can be measured inside a live cell. Such an assay may also be used to investigate the binding of a promiscuous small molecule with only a single protein regardless of how many other proteins the particular small molecule may bind.

In some embodiments, the reactive dyes of the present invention may be used to label a protein(s) or peptide(s) for quantification of protein interactions in situ. In some aspects, a dye label could be attached to the target protein or peptide of interest using the reactive cyanobenzothiazole (CBT) labeling chemistry (see U.S. Patent Application No. 2009/0263843, which is incorporated by reference herein). The CBT labeling chemistry requires a free, N-terminal cysteine residue on the target protein or peptide, which can be generated in situ or in a biochemical format, e.g., by site-specific proteolytic cleavage (e.g. cleavage of an N-terminal reporter such as HaloTag from a C-terminal target protein or peptide). Once proteolysis has occurred and an N-terminal cysteine residue generated, the reactive CBT labeling method can be used to generate a single dye label on the target protein or peptide of interest. This method could also be used for site-specific labeling of receptor ligands (e.g. cytokines or peptide ligands). When the dye-labeled ligand is bound in close proximity to a cell surface receptor labeled with a suitable energy donor (e.g. luciferase for bioluminescence resonance energy transfer (BRET) or a short-wavelength fluorophore for Forster resonance energy transfer (FRET)), energy transfer can occur between the excited state donor and fluorescent dye acceptor, leading to an increase in emission from the conjugated dye. Energy transfer could then be used to quantify the interaction of the protein/peptide that has been labeled with the CBT-dye with the donor-labeled receptor of interest. This labeling method may be compatible with purified components, e.g., purified protein or peptide, or in more complex samples including whole cells or cell lysates. Furthermore, this labeling method may be useful for testing the affinity of unlabeled proteins/peptides for a receptor of interest by competitive displacement of the ligand-receptor complex generating the BRET signal.

Kits

One aspect of the invention is the formulation of kits that facilitate the practice of various assays using any of the dyes of the invention, as described above. The kits of the invention typically comprise a colored or fluorescent dye of the invention, either present as a chemically reactive label useful for preparing dye-conjugates or present as a dye-conjugate where the conjugated substance is a specific binding pair member, or, for instance, a nucleoside, nucleotide, oligonucleotide, polynucleotide, peptide, protein or small molecule, e.g. drug or drug compound. The kit optionally further comprises one or more buffering agents, typically present as an aqueous solution. The kits of the invention optionally further comprise additional detection reagents, a purification medium for purifying the resulting labeled substance, luminescence standards, enzymes, enzyme inhibitors, organic solvent, constructs for expression of fusion proteins, e.g., fusion proteins comprising a luciferase or HaloTag® protein fused to a protein or target of interest, fusion proteins, or instructions for carrying out an assay of the invention.

In some embodiments, a kit of the invention includes one or more locus-specific primers. Instructions for use optionally may be included. Other optional kit components may include an allelic ladder directed to each of the specified loci, a sufficient quantity of enzyme for amplification, amplification buffer to facilitate the amplification, loading solution for preparation of the amplified material for electrophoresis, genomic DNA as a template control, a size marker to insure that materials migrate as anticipated in the separation medium, and a protocol and manual to educate the user and to limit error in use. The amounts of the various reagents in the kits also can be varied depending upon a number of factors, such as the optimum sensitivity of the process. It is within the scope of this invention to provide test kits for use in manual applications or test kits for use with automated detectors or analyzers.

In other embodiments, the kit also includes a genetically-modified cell or a vector for gene fusion, e.g., fusion comprising a luciferase or HaloTag® protein fused to a protein or target of interest. Instructions for use optionally may be included.

The following Examples are intended to illustrate the invention above and should not be construed as to narrow its scope. One skilled in the art will readily recognize that the Examples may suggest other ways in which the present invention could be practiced. It should be understood that variations and modifications may be made while remaining within the scope of the invention.

EXAMPLES

Example 1. 7-methoxytetralone oxime

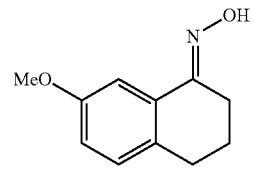 [SMILES: COc1ccc2c(c1)/C(=N/O)CCC2]

To a solution of 7-methoxytetralone (15 g) in MeOH (175 mL), NH$_2$OH (50% in H$_2$O, 15.7 mL) and AcOH (4 mL) was added. After stirring for 1 hour, the solution was concentrated until a solid began to appear. The reaction was poured into dilute aqueous NaHCO$_3$ (500 mL), and the resulting solid was filtered to provide the title compound (17.8 g): 1H NMR (DMSO-d6) δ 11.08 (s, 1H), 7.35 (s, 1H), 7.08 (d, 1H), 6.84 (d, 1H), 3.71 (s, 3H), 2.62-2.49 (m, 4H), 1.77-1.64 (m, 2H).

Example 2. 8-methoxy-4,5-dihydro-1H-benzo[b]azepin-2(3H)-one

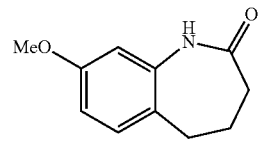

To a solution of 7-methoxytetralone oxime (17.8 g) in pyridine (400 mL), p-toluenesulfonyl chloride (26.6 g) was added portion wise. After stirring for 18 hours, the reaction was poured into HCl (3M, 1 L), and the resulting solid was filtered to provide the crude tosylate (32.4 g). To this orange solid, EtOH (750 mL) and NaOAc (77.0 g in 750 mL H$_2$O) was added, and the resulting suspension was heated to reflux. After refluxing for 16 hours, the heat was removed, and the solution was concentrated until solid began to appear. After cooling, filtered off the resulting white solid to provide the title compound (11.2 g): 1H NMR (DMSO-d6) δ 9.43 (s, 1H); 7.12 (d, 1H), 6.64 (dd, 1H), 6.52 (d, 1H), 3.69 (s, 3H), 2.56 (t, 2H), 2.12 (t, 2H), 2.07-1.98 (m, 2H).

Example 3. 8-methoxy-2,3,4,5-tetrahydro-1H-benzo[b]azepine

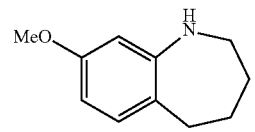 [SMILES: COc1ccc2c(c1)NCCCC2]

To a solution of 8-methoxy-4,5-dihydro-1H-benzo[b]azepin-2(3H)-one (2 g) in THF (100 mL), lithium aluminum hydride (0.79 g) was added, and the reaction heated to reflux. After stirring for 1 hour, the heat was removed. Water (6 mL) was added followed by NaOH (10%, 15 mL), the flocculated solids removed by filtration, and the eluent concentrated to provide the title compound (1.9 g) as a pale brown oil: 1H NMR (DMSO-d6) δ 6.88 (d, 1H); 6.37 (d, 1H), 6.22 (dd, 1H), 5.14 (s, 1H), 3.62 (s, 3H), 2.90-2.85 (m, 2H), 2.57-2.53 (m, 2H), 1.67-1.59 (m, 2H), 1.52-1.45 (m, 2H).

Example 4. 8-methoxy-2,3,4,5-tetrahydro-1-ethyl-benzo[b]azepine

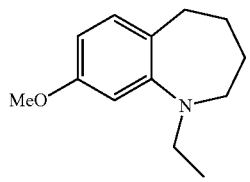

To a solution of 8-methoxy-2,3,4,5-tetrahydro-1H-benzo[b]azepine (0.5 g) in acetonitrile (25 mL), iodoethane (0.45 mL) and $K_2CO_3$ (1.2 g) was added, and the reaction heated to reflux. After stirring for 18 hours, the heat was removed, and the reaction was concentrated. The resulting residue was partitioned between water (30 mL) and EtOAc (25 mL), the layers separated, and the organic layer washed with brine, dried ($Na_2SO_4$) and concentrated to provide the title compound (0.54 g) as a clear oil: 1H NMR (DMSO-d6) δ 6.93 (d, 1H); 6.39 (d, 1H), 6.33 (dd, 1H), 3.67 (s, 3H), 3.07 (q, 2H), 2.85-2.82 (m, 2H), 2.62-2.58 (m, 2H), 1.66-1.59 (m, 2H), 1.51-1.43 (m, 2H), 1.10 (t, 3H).

Example 5. 8-hydroxy-2,3,4,5-tetrahydro-1-ethyl-benzo[b]azepine

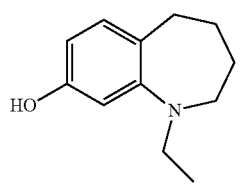

To a solution of 8-methoxy-2,3,4,5-tetrahydro-1-ethyl-benzo[b]azepine (0.54 g) in $CH_2Cl_2$ (25 mL) cooled to -78° C., $BBr_3$ (1.24 mL) was added, and the reaction allowed to gradually warm to -20° C. After stirring for 3 hours, the reaction was quenched with MeOH, allowed to warm to room temperature, and then concentrated. The residue was dissolved in HCl (1M, 40 mL) and stirred for 1 hour. This solution was brought to pH 12 with $K_2CO_3$ (sat. aq.) and extracted with EtOAc (40 mL). The organic layer was washed with brine, dried ($Na_2SO_4$) and concentrated. The crude product was purified by silica gel chromatography (gradient of EtOAc in heptane) to provide the title compound (0.37 g) as a clear oil: 1H NMR (DMSO-d6) δ 8.88 (s, 1H), 6.79 (d, 1H); 6.29 (d, 1H), 6.16 (dd, 1H), 3.02 (q, 2H), 2.82-2.79 (m, 2H), 2.57-2.53 (m, 2H), 1.65-1.57 (m, 2H), 1.48-1.42 (m, 2H), 1.09 (t, 3H); MS expected 192 ($C_{12}H_{18}NO$, M+1), found 192.

Example 6. Bis(ethylazepino)tetrachlororhodamine (PBI 3737)

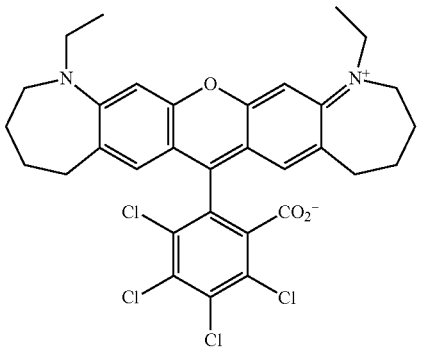

A mixture of 8-hydroxy-2,3,4,5-tetrahydro-1-ethylbenzo[b]azepine (50 mg), tetrachlorophthalic anhydride (52 mg) and $ZnCl_2$ (36 mg) was heated to approximately 250° C. for 2 minutes. The residue was suspended in $CH_2Cl_2$/MeOH (1/1, 20 mL), filtered and concentrated. The crude dye was purified by preparative HPLC (gradient of ACN in 0.1% TFA in $H_2O$) to provide the title compound (1 mg) as a blue solid: MS expected 632 ($C_{32}H_{30}Cl_4N_2O_3^+$, M+), found 632; λmaxAbs=595 nm (MeOH), λmaxEm=619 nm (MeOH).

Example 7. Synthesis of Additional Compounds

The following compounds were synthesized in the same manner as PBI 3737 using the appropriate phenol and phthalic anhydride. In some cases, the rosamine resulting from decarboxylation of the rhodamine was also isolated.

| Structure | PBI Number | MS | $\lambda_{max}$Abs | $\lambda_{max}$Em |
|---|---|---|---|---|
| 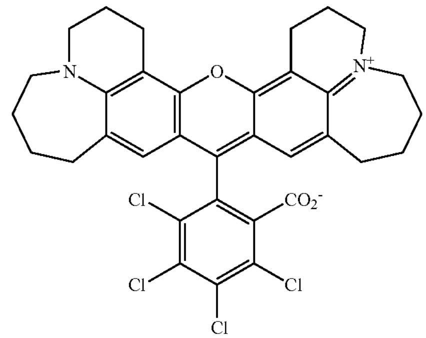 | 3738 | 656 | 608 | 629 |

-continued
| Structure | PBI Number | MS | $\lambda_{max}$Abs | $\lambda_{max}$Em |
|---|---|---|---|---|
| 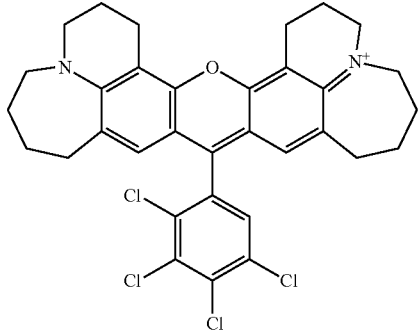 [SMILES: Clc1cc(C2=c3cc4c5c(c3Oc3c2cc2c6c3CCCN6CCCC2)CCC[N+]=5CCCC4)c(Cl)c(Cl)c1Cl] | 3761 | 613 | 610 | 633 |
| 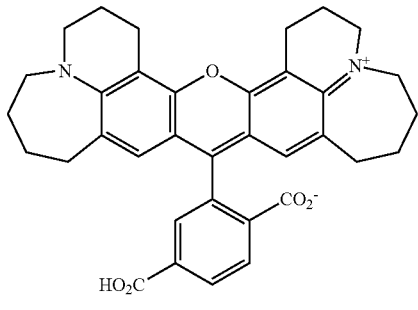 | 3739 | 562 | 583 | 604 |
| 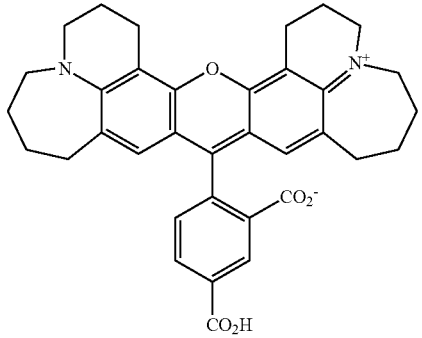 | 3740 | 562 | 585 | 611 |
| 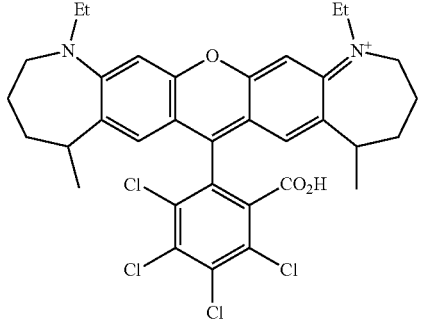 [SMILES: CCN1CCCC(C)c2cc3c(cc21)Oc1cc2c(cc1=C3c1c(Cl)c(Cl)c(Cl)c(Cl)c1C(=O)O)C(C)CCC[N+]=2CC] | 3736 | 661 | 594 | 621 |

-continued

| Structure | PBI Number | MS | $\lambda_{max}$Abs | $\lambda_{max}$Em |
|---|---|---|---|---|
| 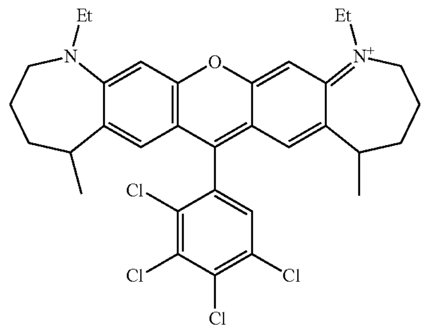 [SMILES: CCN1CCCC(C)c2cc3c(cc21)Oc1cc2c(cc1=C3c1cc(Cl)c(Cl)c(Cl)c1Cl)C(C)CCC[N+]=2CC] | 3760 | 617 | 596 | 626 |
| 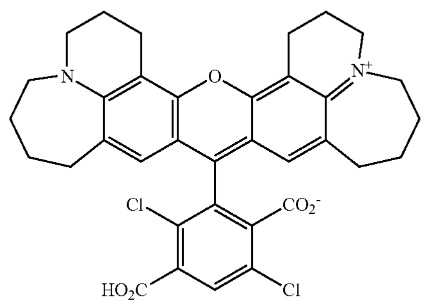 | 3762 | 631 | 601 | 621 |
| 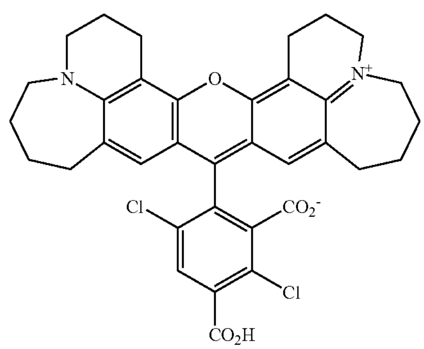 | 3763 | 631 | 602 | 621 |
| 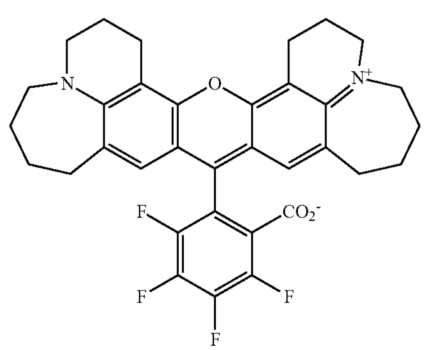 | 3768 | 590 | 607 | 629 |

| Structure | PBI Number | MS | λ_max Abs | λ_max Em |
|---|---|---|---|---|
| (structure shown) | 631 | | | |
| (structure shown) | 3970 | 631 | 604 | 617 |

Example 8. 11-methoxy-2,3,5,6,7,8-hexahydro-1H-azepino[3,2,1-ij]quinoline

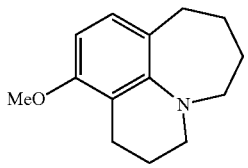 [SMILES: COc1ccc2c3c1CCCN3CCCC2]

To a solution of 8-methoxy-2,3,4,5-tetrahydro-1H-benzo[b]azepine (0.25 g) in bromochloropropane (2 mL), Na$_2$CO$_3$ (0.6 g) was added, and the reaction heated to reflux. After stirring for 18 hours, the heat was removed, the reaction partitioned between water (30 mL) and ether (25 mL), the layers separated, and the organic layer washed with brine, dried (Na$_2$SO$_4$) and concentrated. The crude product was purified by silica gel chromatography (gradient of EtOAc in heptane) to provide the title compound (0.27 g) as a clear oil: 1H NMR (DMSO-d6) δ 6.82 (d, 1H); 6.36 (d, 1H), 3.68 (s, 3H), 3.04-3.00 (m, 2H), 2.89-2.85 (m, 2H), 2.60-2.57 (m, 2H), 2.53-2.49 (m, 2H), 1.70-1.61 (m, 4H), 1.48-1.40 (m, 2H); MS expected 218 (C$_{14}$H$_{20}$NO, M+1), found 218.

Example 9. 11-hydroxy-2,3,5,6,7,8-hexahydro-1H-azepino[3,2,1-ij]quinoline

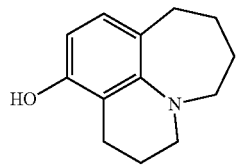 [SMILES: Oc1ccc2c3c1CCCN3CCCC2]

The title compound was synthesized in a similar manner as 8-hydroxy-2,3,4,5-tetrahydro-1-ethylbenzo[b]azepine from 11-methoxy-2,3,5,6,7,8-hexahydro-1H-azepino[3,2,1-ij]quinoline: 1H NMR (DMSO-d6) δ 8.82 (s, 1H), 6.64 (d, 1H); 6.22 (d, 1H), 3.03-2.99 (m, 2H), 2.87-2.83 (m, 2H), 2.55-2.50 (m, 2H), 2.53-2.49 (m, 2H), 1.68-1.61 (m, 4H), 1.45-1.37 (m, 2H); MS expected 204 (C$_{13}$H$_{18}$NO, M+1), found 204.

Example 10. 8-methoxy-5-methyl-2,3-dihydro-1H-benzo[b]azepine

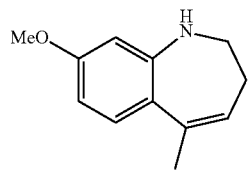

The title compound was synthesized following the procedure for synthesizing 8-methoxy-2,3,4,5-tetrahydro-1H-benzo[b]azepine using 8-methoxy-5-methyl-1H-benzo[b]azepin-2(3H)-one (Aust. J. Chem. 1978, 31, 2031-2037) as starting material: 1H NMR (DMSO-d6) δ 7.28 (d, 1H), 6.46 (dd, 1H); 6.28 (d, 1H), 5.89 (t, 1H), 5.30 (s, 1H), 3.77 (s, 3H), 3.40 (t, 2H), 2.41 (q, 2H), 2.14 (d, 3H); MS expected 190 (C$_{12}$H$_{16}$NO, M+1), found 190.

53

Example 11. 8-hydroxy-5-methyl-2,3-dihydro-1-ethylbenzo[b]azepine

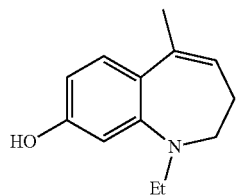

The title compound was synthesized from 8-methoxy-5-methyl-2,3-dihydro-1H-benzo[b]azepine following the alkylation procedure for 8-methoxy-2,3,4,5-tetrahydro-1-ethylbenzo[b]azepine followed by the demethylation procedure used to synthesize 8-hydroxy-2,3,4,5-tetrahydro-1-ethylbenzo[b]azepine: 1H NMR (DMSO-d6) δ 9.15 (s, 1H), 7.05 (d, 1H), 6.31-6.25 (m, 2H), 5.80 (t, 1H), 5.30 (s, 1H), 3.12-3.03 (m, 4H), 2.17 (q, 2H), 1.97 (s, 3H), 1.09 (t, 3H); MS expected 203 ($C_{13}H_{18}NO$, M+1), found 203.

Example 12. 8-hydroxy-5-methyl-2,3,4,5-tetrahydro-1-ethylbenzo[b]azepine

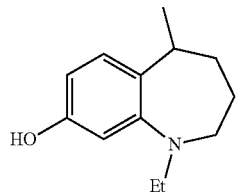

A suspension of 8-hydroxy-5-methyl-2,3-dihydro-1-ethylbenzo[b]azepine (0.14 g) and Pd/C (10 mg) in MeOH (10 mL) was purged with $H_2$ and then stirred under 1 atm $H_2$ for 3 hours. The reaction was then filtered over Celite, the eluent concentrated, and the crude reaction purified over silica gel (gradient of EtOAc in heptane) to provide the title compound (0.09 g) as a clear oil: 1H NMR (CDCl3) δ 7.26 (s, 1H), 6.97 (d, 1H), 6.46-6.33 (m, 2H), 3.23-3.02 (m, 4H), 2.79-2.67 (m, 2H), 1.81-1.53 (m, 3H), 1.29 (d, 3H), 1.19 (t, 3H); MS expected 206 ($C_{13}H_{20}NO$, M+1), found 206.

Example 13. 9-hydroxy-2,3,5,6,7,8-hexahydro-1H-azepino[3,2,1-ij]quinoline

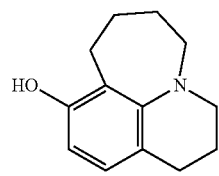 [SMILES: Oc1ccc2c3c1CCCCN3CCC2]

54

The title compound was synthesized in a similar manner as 11-hydroxy-2,3,5,6,7,8-hexahydro-1H-azepino[3,2,1-ij]quinolone starting from 5-methoxytetralone: 1H NMR (DMSO-d6) δ 8.69 (s, 1H), 6.55 (d, 1H); 6.27 (d, 1H), 3.05-3.02 (m, 2H), 2.92-2.89 (m, 2H), 2.68-2.64 (m, 2H), 2.54 (t, 2H), 1.69-1.60 (m, 4H), 1.45-1.37 (m, 2H); MS expected 204 ($C_{13}H_{18}NO$, M+1), found 204.

Example 14. 2,3,4,5-tetrachloro-6-(9-hydroxy-2,3,5,6,7,8-hexahydro-1H-azepino[3,2,1-ij]quinoline-10-carbonyl)benzoic acid

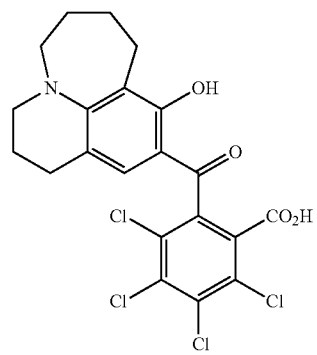 [SMILES: O=C(O)c1c(Cl)c(Cl)c(Cl)c(Cl)c1C(=O)c1cc2c3c(c1O)CCCCN3CCC2]

To a solution of 9-hydroxy-2,3,5,6,7,8-hexahydro-1H-azepino[3,2,1-ij]quinolone (30 mg) in dichlorobenzene (1 mL), tetrachlorophthalic anhydride (0.13 mL) was added. After stirring at reflux for 2 hours, the solvent was removed, and the resulting crude product purified by preparative HPLC (gradient of ACN in 0.1% TFA in $H_2O$) to provide the title compound (20 mg) as a green solid: MS expected 490 ($C_{21}H_{18}Cl_4NO_4^+$, M+), found 490.

Example 15. Synthesis of Additional Compounds

The following compounds were synthesized in the same manner as 2,3,4,5-tetrachloro-6-(9-hydroxy-2,3,5,6,7,8-hexahydro-1H-azepino[3,2,1-ij]quinoline-10-carbonyl)benzoic acid using the appropriate phenol and phthalic anhydride:

| Structure | MS |
| --- | --- |
| 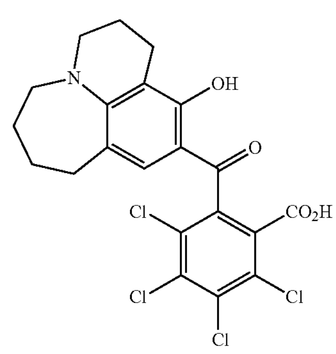 [SMILES: O=C(O)c1c(Cl)c(Cl)c(Cl)c(Cl)c1C(=O)c1cc2c3c(c1O)CCCN3CCCC2] | 489 |

| Structure | MS |
|---|---|
| 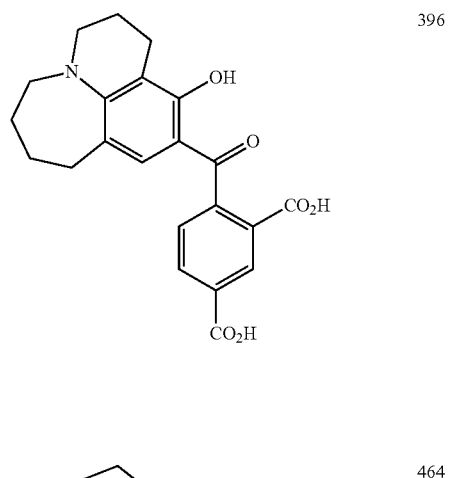 | 396 |
| | 396 |
| | 464 |
| | 464 |

| Structure | MS |
|---|---|
| 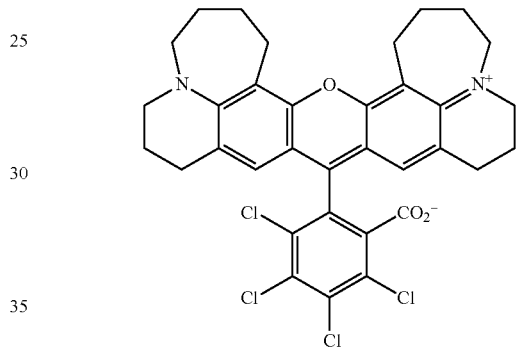 | 424 |

Example 16.
Bis(azepinopiperidino)-tetrachlororhodamine (PBI 3861)

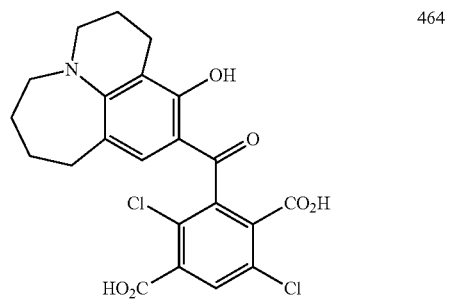
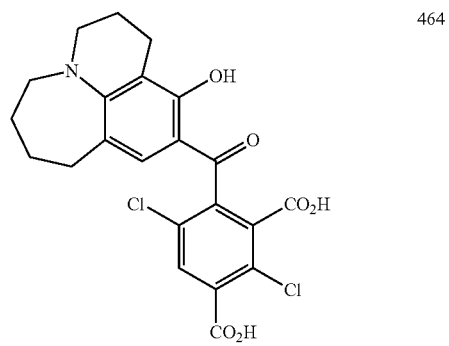

To a solution of 2,3,4,5-tetrachloro-6-(9-hydroxy-2,3,5,6,7,8-hexahydro-1H-azepino[3,2,1-ij]quinoline-10-carbonyl) benzoic acid (20 mg) and 9-hydroxy-2,3,5,6,7,8-hexahydro-1H-azepino[3,2,1-iMuinolone (14 mg) in DMF (1 mL), trimethylsilylpolyphosphate (0.25 mL) was added. After stirring at 80° C. for 1 hour, water (1 mL) was added, and the resulting solution purified by preparative HPLC (gradient of ACN in 0.1% TFA in H$_2$O) to provide the title compound (10 mg) as a blue solid: MS expected 656 (C$_{34}$H$_{30}$Cl$_4$N$_2$O$_3$$^+$, M+), found 656; λmaxAbs=605 nm (MeOH), λmaxEm=620 nm (MeOH).

Example 17. Synthesis of Additional Compounds

The following compounds were synthesized in the same manner as bis(azepinopiperidino)-tetrachlororhodamine using the appropriate phenol and ketophenol from Example 14 or 15.

| Structure | PBI Number | MS | $\lambda_{max}$Abs | $\lambda_{max}$Em |
|---|---|---|---|---|
| 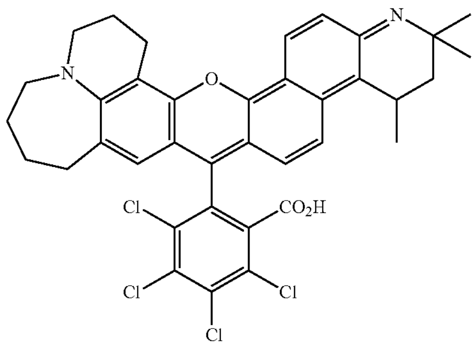 [SMILES: CC1CC(C)(C)N=c2ccc3c4c(ccc3c21)=C(c1c(Cl)c(Cl)c(Cl)c(Cl)c1C(=O)O)c1cc2c3c(c1O4)CCCN3CCCC2] | 4273 | 694 | 647 | 713 |
| 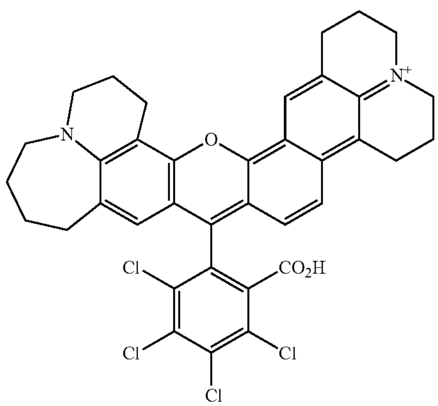 [SMILES: O=C(O)c1c(Cl)c(Cl)c(Cl)c(Cl)c1C1=c2ccc3c4c5c(cc3c2Oc2c1cc1c3c2CCCN3CCCC1)CCC[N+]=5CCC4] | 4302 | 693 | 668 | 741 |
| 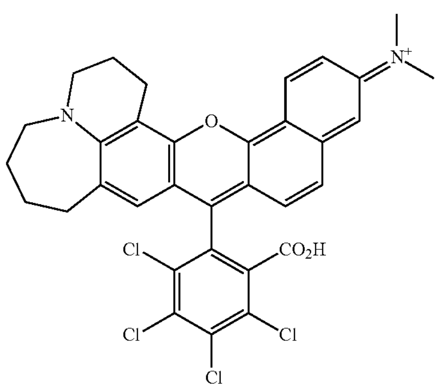 [SMILES: C[N+](C)=c1ccc2c(ccc3c(-c4c(Cl)c(Cl)c(Cl)c(Cl)c4C(=O)O)c4cc5c6c(c4oc32)CCCN6CCCC5)c1] | 4335 | 641 | 632 | 690 |
| 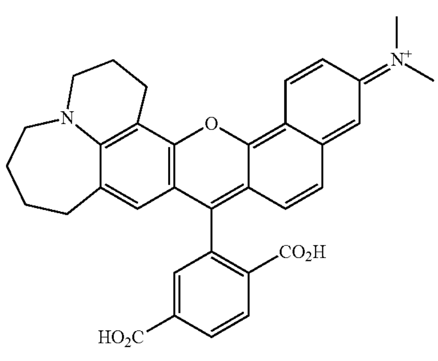 [SMILES: C[N+](C)=c1ccc2c(ccc3c(-c4cc(C(=O)O)ccc4C(=O)O)c4cc5c6c(c4oc32)CCCN6CCCC5)c1] | 4351 | 548 | 602 | 662 |

-continued

| Structure | PBI Number | MS | $\lambda_{max}$Abs | $\lambda_{max}$Em |
|---|---|---|---|---|
| 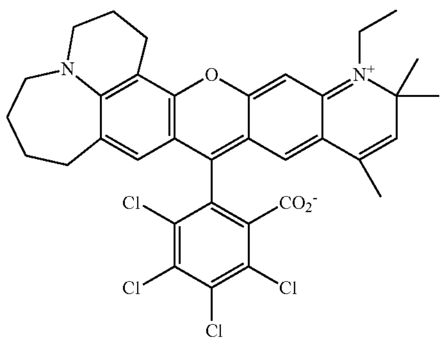 | 4352 | 670 | 614 | 632 |
| 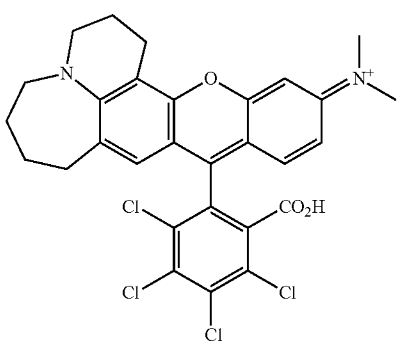 [SMILES: C[N+](C)=c1ccc2c(-c3c(Cl)c(Cl)c(Cl)c(Cl)c3C(=O)O)c3cc4c5c(c3oc-2c1)CCCN5CCCC4] | 4379 | 591 | 590 | 612 |
| 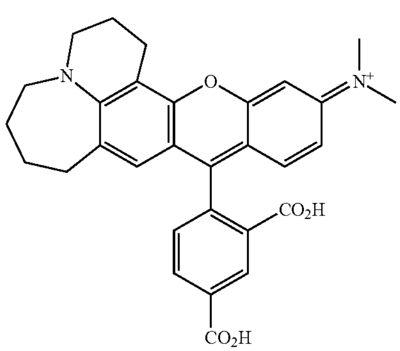 [SMILES: C[N+](C)=c1ccc2c(-c3ccc(C(=O)O)cc3C(=O)O)c3cc4c5c(c3oc-2c1)CCCN5CCCC4] | 4382 | 497 | 564 | 596 |
| 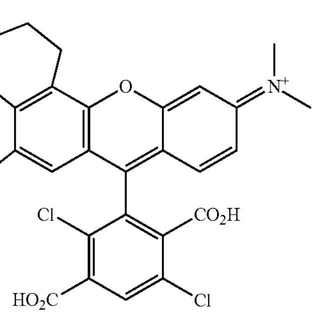 | 4428 | 566 | 583 | 604 |

-continued
| Structure | PBI Number | MS | $\lambda_{max}$Abs | $\lambda_{max}$Em |
|---|---|---|---|---|
| 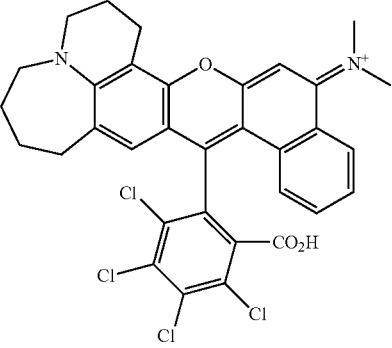 [SMILES: C[N+](C)=c1cc2oc3c4c5c(cc3c(-c3c(Cl)c(Cl)c(Cl)c(Cl)c3C(=O)O)c-2c2ccccc12)CCCCN5CCC4] | 4464 | 641 | 611 | 644 |
| 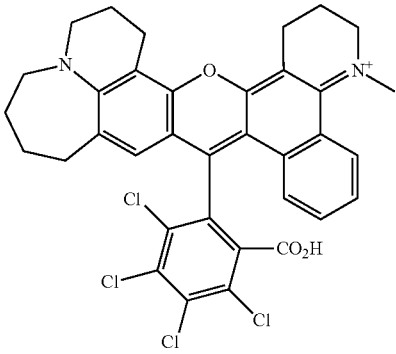 [SMILES: C[N+]1=c2c(c3c(c4ccccc24)=C(c2c(Cl)c(Cl)c(Cl)c(Cl)c2C(=O)O)c2cc4c5c(c2O3)CCCN5CCCC4)CCC1] | 4484 | 667 | 614 | 646 |
| 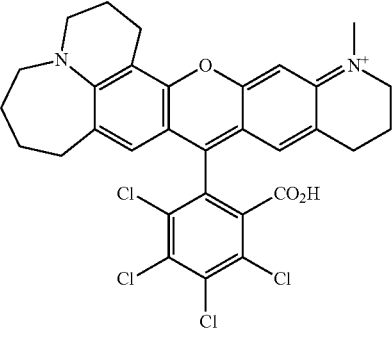 [SMILES: C[N+]1=c2cc3c(cc2CCC1)=C(c1c(Cl)c(Cl)c(Cl)c(Cl)c1C(=O)O)c1cc2c4c(c1O3)CCCN4CCCC2] | 4490 | 617 | 592 | 616 |
| 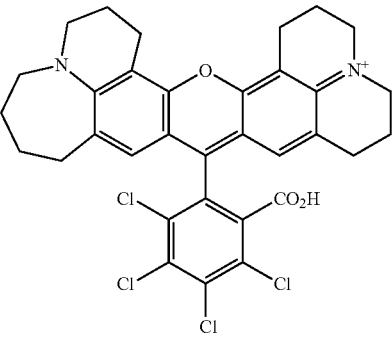 [SMILES: O=C(O)c1c(Cl)c(Cl)c(Cl)c(Cl)c1C1=c2cc3c4c(c2Oc2c1cc1c5c2CCCN5CCCC1)CCC[N+]=4CCC3] | 4496 | 643 | 601 | 621 |

-continued

| Structure | PBI Number | MS | $\lambda_{max}$Abs | $\lambda_{max}$Em |
|---|---|---|---|---|
| 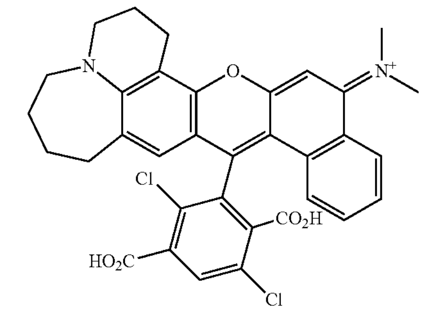 [SMILES: C[N+](C)=c1cc2oc3c4c5c(cc3c(-c3c(Cl)c(C(=O)O)cc(Cl)c3C(=O)O)c-2c2ccccc12)CCCCN5CCC4] | 4497 | 616 | 598 | 637 |
| 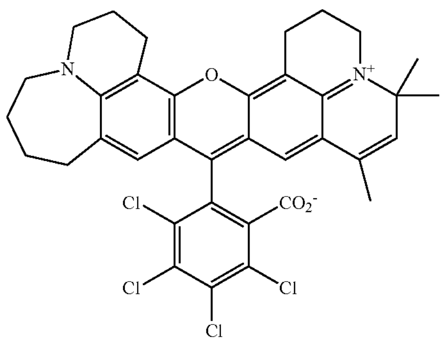 | 4553 | 682 | 619 | 637 |
| | 575 | 602 | 642 | |
| | 617 | 617 | 638 | |

| Structure | PBI Number | MS | $\lambda_{max}$Abs | $\lambda_{max}$Em |
|---|---|---|---|---|
| 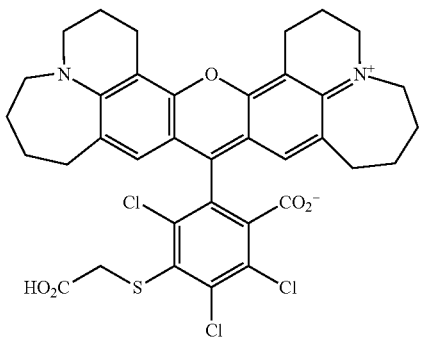 | 4624 | 497 | 571 | 601 |

Example 18. Bis(piperidineazepino)-trichlororhodamine mercaptoacetic Acid (PBI 3769)

To a solution of bis(piperidineazepino)-tetrachlororhodamine (PBI 3738, 0.60 g) and diisopropylethylamine (0.32 mL) in DMF (10 mL), mercaptoacetic acid (0.13 mL) was added. After stirring for 2 hours, the resulting product was purified by preparative HPLC (gradient of ACN in 0.1% TFA in H$_2$O) to provide the title compound (0.35 g) as a blue solid: MS expected 712 (C$_{36}$H$_{33}$Cl$_3$N$_2$O$_5$S$^+$, M+), found 712; $\lambda$maxAbs=606 nm (MeOH), $\lambda$maxEm=627 nm (MeOH).

Example 19. Synthesis of Additional Compounds

The following compounds were synthesized in the same manner as PBI 3769 using the appropriate halorhodamine:

| Structure | PBI Number | MS | $\lambda_{max}$Abs | $\lambda_{max}$Em |
|---|---|---|---|---|
| (structure) | | 662 | 610 | 633 |
| (structure) | 3865 | 637 | 617 | 642 |

-continued
| Structure | PBI Number | MS | $\lambda_{max}$Abs | $\lambda_{max}$Em |
|---|---|---|---|---|
| 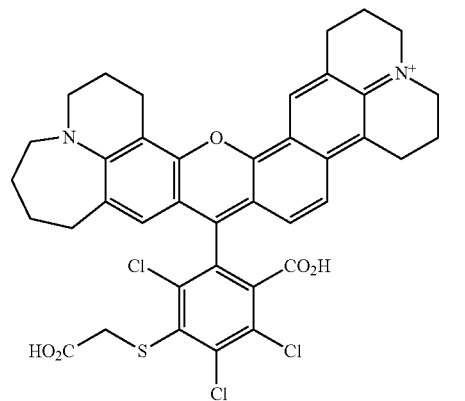 [SMILES: O=C(O)CSc1c(Cl)c(Cl)c(C(=O)O)c(C2=c3ccc4c5c6c(cc4c3Oc3c2cc2c4c3CCCN4CCCC2)CCC[N+]=6CCC5)c1Cl] | 749 | | | |
| 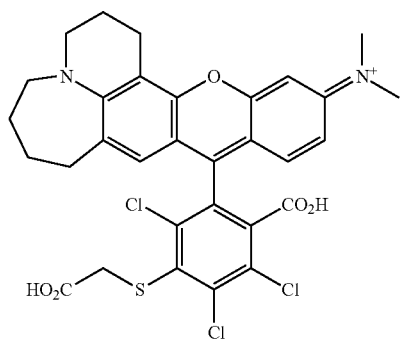 [SMILES: C[N+](C)=c1ccc2c(-c3c(Cl)c(SCC(=O)O)c(Cl)c(Cl)c3C(=O)O)c3cc4c5c(c3oc-2c1)CCCN5CCCC4] | | 647 | 589 | 613 |
| 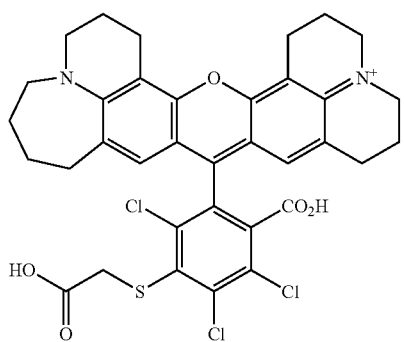 [SMILES: O=C(O)CSc1c(Cl)c(Cl)c(C(=O)O)c(C2=c3cc4c5c(c3Oc3c2cc2c6c3CCCN6CCCC2)CCC[N+]=5CCC4)c1Cl] | 4577 | 699 | 600 | 620 |
| 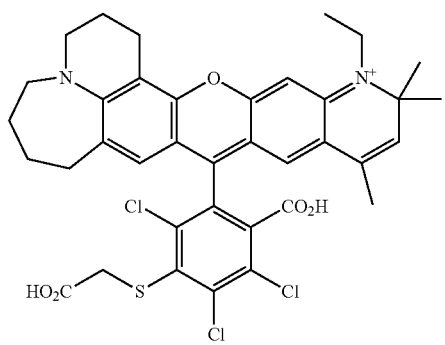 [SMILES: CC[N+]1=c2cc3c(cc2C(C)=CC1(C)C)=C(c1c(Cl)c(SCC(=O)O)c(Cl)c(Cl)c1C(=O)O)c1cc2c4c(c1O3)CCCN4CCCC2] | 4555 | 727 | 610 | 629 |

-continued

| Structure | PBI Number | MS | $\lambda_{max}$Abs | $\lambda_{max}$Em |
|---|---|---|---|---|
| 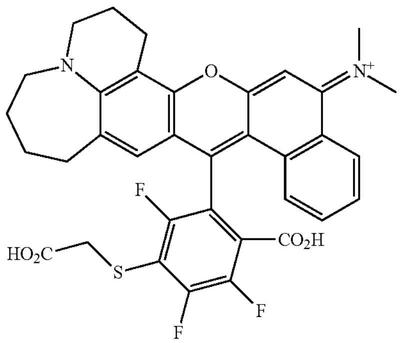 [SMILES: C[N+](C)=c1cc2oc3c4c5c(cc3c(-c3c(F)c(SCC(=O)O)c(F)c(F)c3C(=O)O)c-2c2ccccc12)CCCCN5CCC4] | 4559 | 647 | 604 | 645 |
| 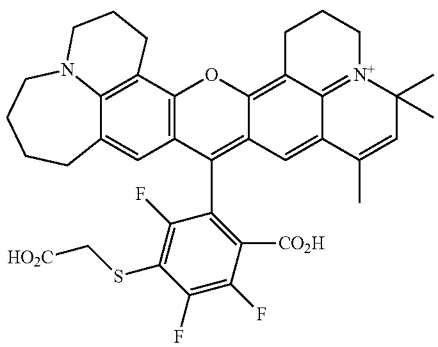 [SMILES: CC1=CC(C)(C)[N+]2=c3c1cc1c(c3CCC2)Oc2c(cc3c4c2CCCN4CCCC3)C=1c1c(F)c(SCC(=O)O)c(F)c(F)c1C(=O)O] | 4568 | 689 | 613 | 633 |
| 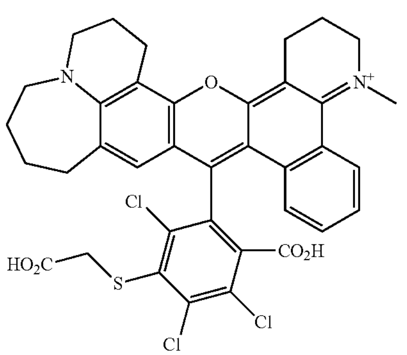 [SMILES: C[N+]1=c2c(c3c(c4ccccc24)=C(c2c(Cl)c(SCC(=O)O)c(Cl)c(Cl)c2C(=O)O)c2cc4c5c(c2O3)CCCN5CCCC4)CCC1] | 4681 | 721 | 614 | 652 |

Example 20. Bis(piperidinoazepino)-pentafluororosamine (PBI 3860)

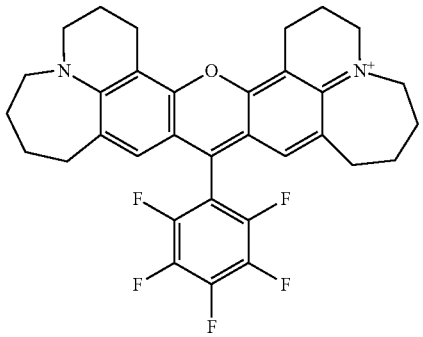 [SMILES: Fc1c(F)c(F)c(C2=c3cc4c5c(c3Oc3c2cc2c6c3CCCN6CCCC2)CCC[N+]=5CCCC4)c(F)c1F]

A solution of pentafluorobenzaldehyde (40 mg) and 11-hydroxy-2,3,5,6,7,8-hexahydro-1H-azepino[3,2,1-ij]quinolone (50 mg) in $H_2SO_4$ (60% aqueous, 2 mL) was stirred at 150° C. for 10 minutes. The resulting solution was purified by preparative HPLC (gradient of ACN in 0.1% TFA in $H_2O$) to provide the title compound (20 mg) as a blue solid: MS expected 565 ($C_{33}H_{30}F_5N_2O^+$, M+), found 565; $\lambda_{max}$Abs=620 nm (MeOH), $\lambda_{max}$Em=642 nm (MeOH).

Example 21. Bis(piperidineazepino)-6-((2-(2-((6-chlorohexyl)oxy)ethoxy)ethyl)-carbamoyl)rhodamine (PBI 3781)

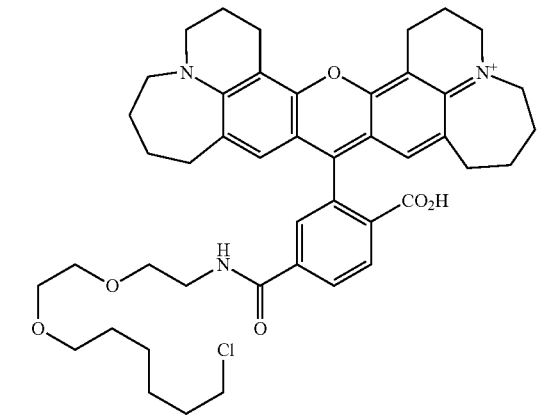 [SMILES: O=C(NCCOCCOCCCCCCCl)c1ccc(C(=O)O)c(C2=c3cc4c5c(c3Oc3c2cc2c6c3CCCN6CCCC2)CCC[N+]=5CCCC4)c1]

To a solution of bis(piperidineazepino)-6-carboxyrhodamine (10 mg) and diisopropylethylamine (0.02 mL) in DMF (1 mL), TSTU (8 mg) was added. After stirring for 15 minutes, 2-(2-((6-chlorohexyl)oxy)ethoxy)ethylamine HCl (7 mg) was added, which was synthesized according to the procedure described in H. Benink, M. McDougall, D. Klaubert, G. Los, BioTechniques 2009, 47, 769-774 (which is incorporated by reference herein). After stirring another 30 minutes, the reaction mixture was purified by preparative HPLC (gradient of ACN in 0.1% TFA in $H_2O$) to provide the title compound (1 mg) as a blue solid: MS expected 769 ($C_{45}H_{55}ClN_3O_6^+$, M+), found 769.

Example 22. Synthesis of Additional Compounds

The following compounds were synthesized in the same manner as PBI 3781 using the appropriate dye carboxylic acid and amine.

| Structure | PBI Number | MS |
|---|---|---|
| 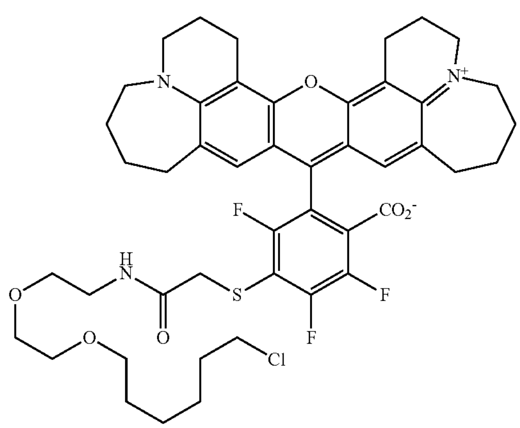 | 3780 | 868 |

-continued
| Structure | PBI Number | MS |
|---|---|---|
| 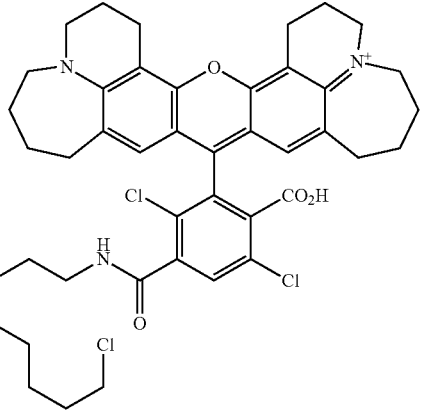 | 3782 | 838 |
| 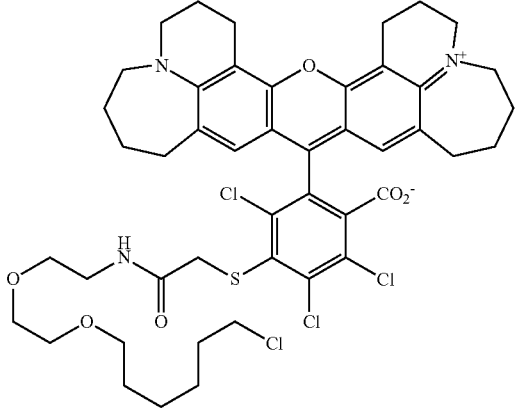 | 3783 | 917 |
| 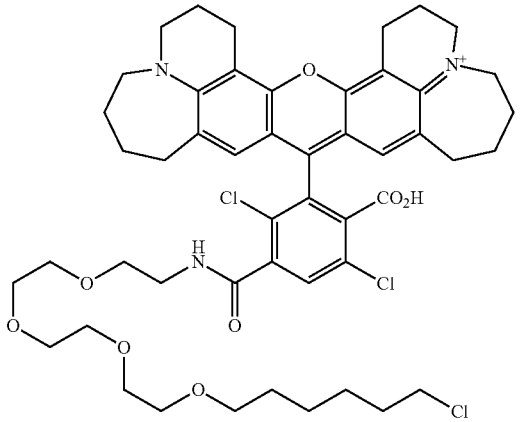 [SMILES: O=C(NCCOCCOCCOCCOCCCCCCCl)c1cc(Cl)c(C(=O)O)c(C2=c3cc4c5c(c3Oc3c2cc2c6c3CCCN6CCCC2)CCC[N+]=5CCCC4)c1Cl] | 3905 | 926 |

-continued
| Structure | PBI Number | MS |
|---|---|---|
| 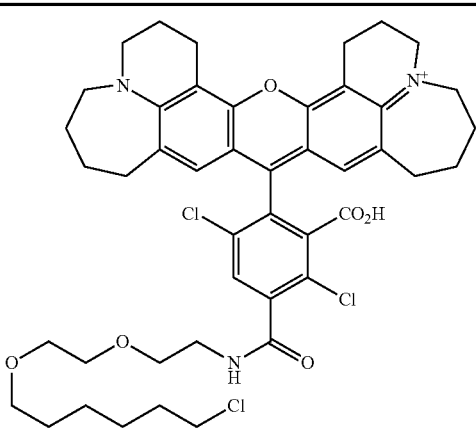 | 3906 | 838 |
| 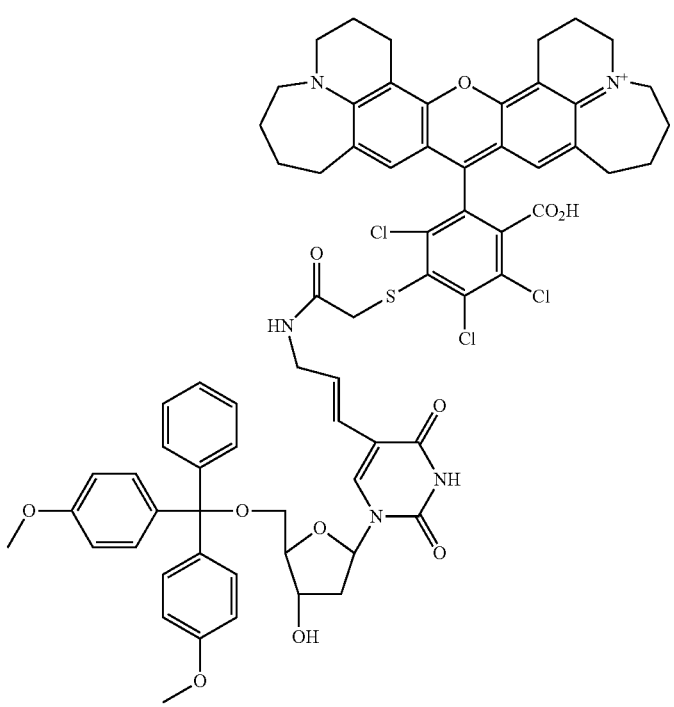 [SMILES: COc1ccc(C(OCC2OC(n3cc(/C=C/CNC(=O)CSc4c(Cl)c(Cl)c(C(=O)O)c(C5=c6cc7c8c(c6Oc6c5cc5c9c6CCCN9CCCC5)CCC[N+]=8CCCC7)c4Cl)c(=O)[nH]c3=O)CC2O)(c2ccccc2)c2ccc(OC)cc2)cc1] | 1280 | |
| 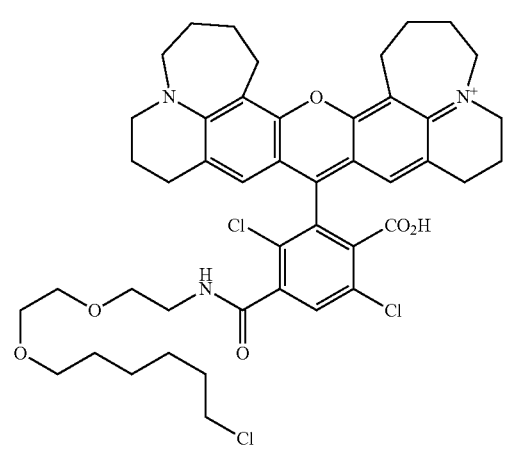 [SMILES: O=C(NCCOCCOCCCCCCCl)c1cc(Cl)c(C(=O)O)c(C2=c3cc4c5c(c3Oc3c2cc2c6c3CCCCN6CCC2)CCCC[N+]=5CCC4)c1Cl] | 3954 | 838 |

-continued

| Structure | PBI Number | MS |
|---|---|---|
| 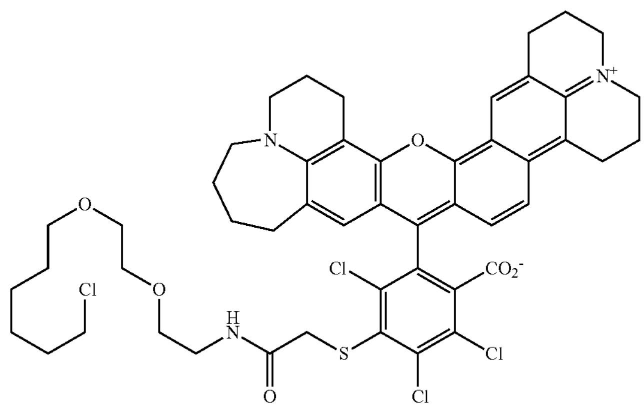 | 4356 | 953 |
| 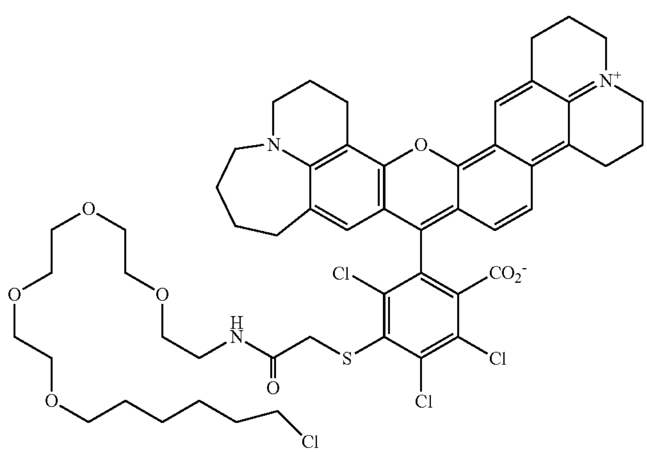 | 4357 | 1042 |
| 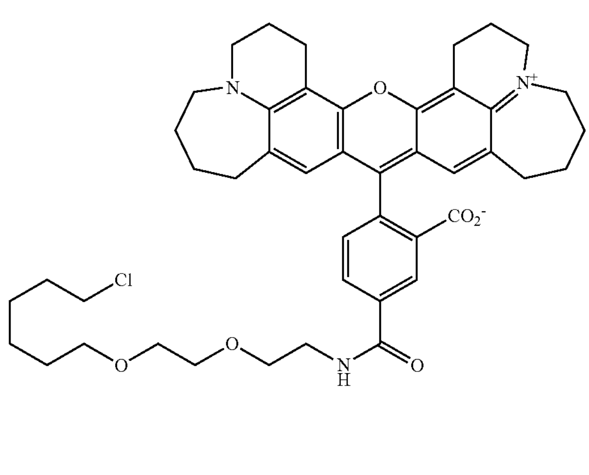 | 4830 | 769 |

| Structure | PBI Number | MS |
|---|---|---|
| 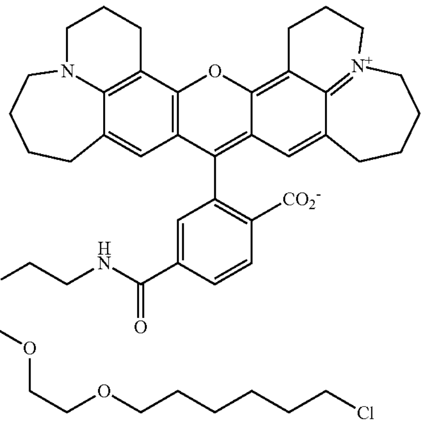 | 4839 | 857 |
| 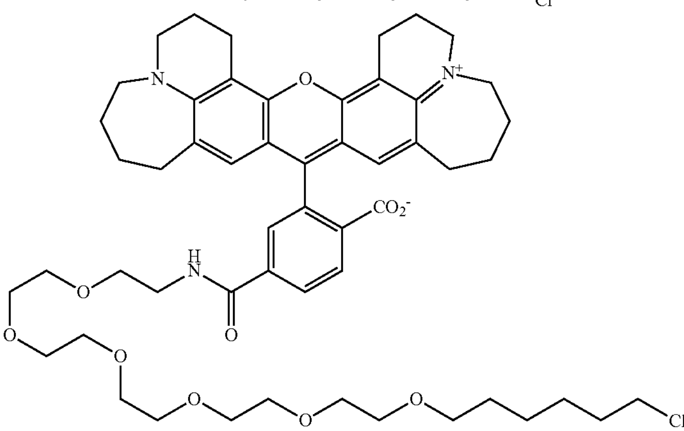 | 4840 | 945 |

Example 23.
Bis(piperidineazepino)trichlororhodamine acetoallylaminodU 5'-DMT 3'-phosphoramidite (PBI 3885)

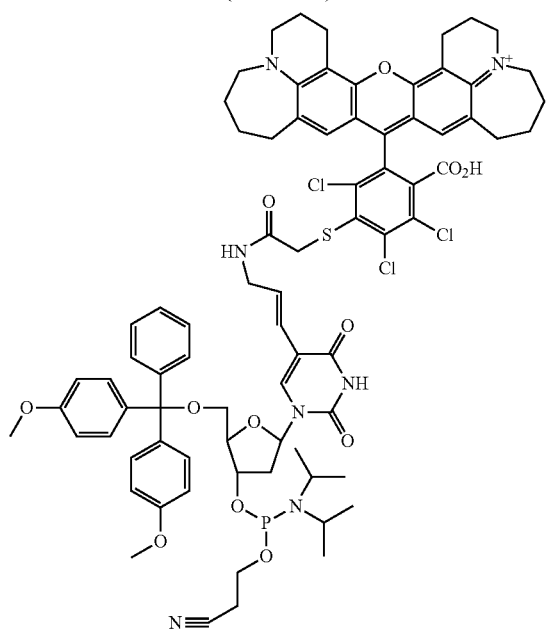

Solid bis(piperidineazepino)trichlororhodamine acetoallylaminodU 5'-DMT (1.0 g) was flushed with $N_2$ and dissolved in dry $CH_2Cl_2$ (10 mL). To this solution, 5-ethylthiotetrazole (30 mg) followed by 2-cyanoethyl-N,N,N',N'-tetraisopropylphosphordiamidite (0.31 mL) was added. After stirring for 90 minutes, the reaction mixture was added to heptane dropwise. The slurry was stirred for 5 minutes and filtered to provide the title compound (1.0 g) as a blue solid: MS expected 1480 ($C_{78}H_{84}Cl_3N_7O_{12}PS+$, M+), found 1480.

Example 24.
Bis(piperidineazepino)-trichlororhodamine mercaptoacetic Acid SE (PBI 4574)

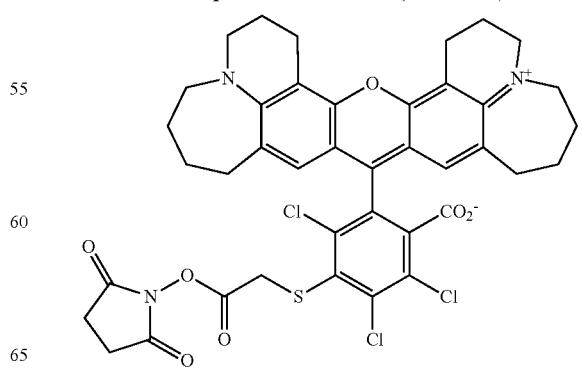

To a solution of bis(piperidineazepino)-trichlororhodamine mercaptoacetic acid (10 mg) and diisopropylethylamine (0.02 mL) in CH$_2$Cl$_2$ (0.5 mL), 2-succimido-1,1,3,3-tetramethyluronium tetrafluoroborate (TSTU) (8 mg) was added. After stirring for 1 hour, the reaction mixture was poured into monosodium citrate (250 mM, 15 mL), extracted with CH$_2$Cl$_2$ (10 mL) three times, and the combined organic layers dried (Na$_2$SO4) and concentrated to provide the title compound (5 mg) as a blue solid: MS expected 809 (C$_{40}$H$_{36}$Cl$_3$N$_3$O$_2$S$^+$, M+), found 809.

Example 25.
Bis(piperidineazepino)-3,5-bissulforhodamine (PBI 3904)

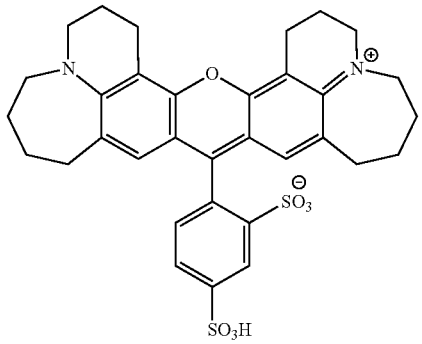

A mixture of 11-hydroxy-2,3,5,6,7,8-hexahydro-1H-azepino[3,2,1-ij]quinoline (50 mg) and 4-formylbenzene-1,3-disulfonic acid disodium salt hydrate (38 mg) in 1 mL of concentrated sulfuric acid was heated with stirring in an open vessel to 100° C. by means of an oil bath for five hours. After this time, the reaction was removed from the oil bath, and ice was slowly added while stirring until liquefied. The acidified water was then decanted from an oily residue which was further washed 2 more times with water. The residue was then dissolved in methanol, and the solvent evaporated depositing the residue onto celite. The crude product was purified by silica gel chromatography (gradient of MeOH in CH$_2$Cl$_2$) to provide the title compound as a red solid (78 mg): MS expected 635 (C$_{33}$H$_{35}$N$_2$O$_7$S$_2$, M+), found 635; λmaxAbs=590 nm (MeOH), λmaxEm=613 nm (MeOH).

Example 26.
Bis(piperidineazepino)-5-sulfonylchloride sulforhodamine

A solution of bis(piperidineazepino)-3,5-bissulforhodamine (PBI 3904, 70 mg) in POCl$_3$ (2 mL) and THF (2 mL) was stirred for 1 hour and then concentrated under reduced pressure. After stirring another 30 minutes, the reaction mixture was purified by preparative HPLC (gradient of ACN in 0.1% TFA in H$_2$O) to provide the title compound (1 mg) as a blue solid: MS expected 769 (C$_{45}$H$_{55}$ClN$_3$O$_6$$^+$, M+), found 769.

Example 27. Bis(piperidineazepino)-5-((2-(2-((6-chlorohexyl)oxy)ethoxy)ethyl)sulfonyl)sulforhodamine (PBI 3909)

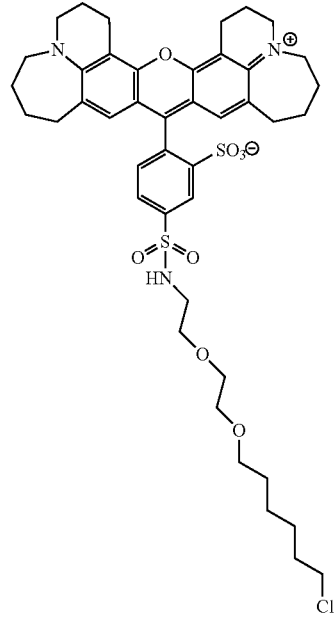

A solution of bis(piperidineazepino)-3,5-bissulforhodamine (PBI 3904, 70 mg) in POCl$_3$ (2 mL) and THF (2 mL) was stirred for 1 hour and then concentrated under reduced pressure. This crude sulfonyl chloride was dissolved in CH$_2$Cl$_2$ (5 mL), and triethylamine (0.23 mL) and 2-(2-((6-chlorohexyl)oxy)ethoxy)ethylamine HCl (43 mg) were added. After stirring for 3 days, the reaction mixture was concentrated. The crude product was dissolved in DMF and purified by preparative HPLC (gradient of ACN in 0.1% TFA in H$_2$O) to provide the title compound (6 mg) as a blue solid: MS expected 840 (C$_{43}$H$_{54}$ClN$_3$O$_8$S$_2$$^+$, M+), found 840.

Example 28. 5-methoxy-2-aminonaphthalene

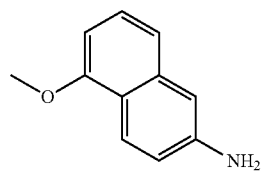

To a solution of 6-aminonaphth-1-ol (1.0 g) in DMF (50 mL), NaH (60% in mineral oil, 0.17 g) was added, and the reaction was stirred for 1 hour. Iodomethane (0.39 mL) was added, and the reaction was stirred for another 1 hour. The reaction was then partitioned between NaHCO$_3$ (aq., 150 mL) and EtOAc (100 mL), the layers separated, and the organic layer washed with brine, dried (Na$_2$SO$_4$) and concentrated. The crude reaction was purified over silica gel (gradient of EtOAc in heptane) to provide the title compound (0.8 g) as an orange oil: 1H NMR (DMSO-d6) δ 7.81 (d, 1H); 7.16 (dd, 1H), 7.04 (d, 1H), 6.85 (dd, 1H), 6.75 (d, 1H), 6.53 (dd, 1H), 5.32 (s, 2H), 3.86 (s, 3H).

Example 29.
5-hydroxy-2-(dimethylamino)naphthalene

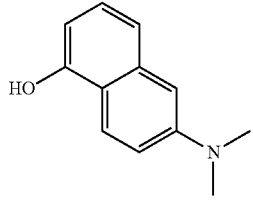

From the purification of 5-methoxy-2-aminonaphthalene 5-methoxy-2-(dimethylamino)naphthalene was also isolated. This compound was demethylated in the same manner as 8-hydroxy-2,3,4,5-tetrahydro-1-ethylbenzo[b]azepine to give the title compound: 1H NMR (DMSO-d6) δ 9.72 (s, 1H), 7.93 (d, 1H); 7.10-7.05 (m, 3H), 6.82 (d, 1H), 6.52 (dd, 1H), 2.96 (s, 6H); MS expected 188 ($C_{12}H_{13}NO$, M+1), found 188.

Example 30. 9-hydroxy-1,2,3,5,6,7-hexahydrobenzo[f]pyrido[3,2,1-u]quinolone

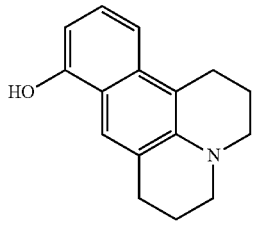 [SMILES: Oc1cccc2c3c4c(cc12)CCCN4CCC3]

The title compound was synthesized in a similar manner as 11-hydroxy-2,3,5,6,7,8-hexahydro-1H-azepino[3,2,1-ij]quinolone starting from 5-methoxy-2-aminonaphthalene: 1H NMR (DMSO-d6) δ 9.55 (s, 1H), 7.55 (s, 1H); 7.08-7.00 (m, 2H), 6.48 (dd, 1H), 3.14 (q, 4H), 2.86 (q, 2H), 2.02-1.86 (m, 4H); MS expected 240 ($C_{16}H_{18}NO$, M+1), found 240.

Example 31.
3-methoxy-1-(dimethylamino)naphthalene

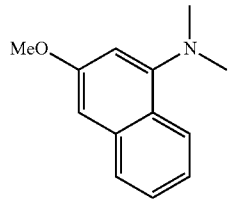

To a solution of 3-methoxy-1-aminonaphthalene (U.S. Pat. No. 7,018,431 B2, 0.13 g) in DMF (5 mL), $K_2CO_3$ (0.31 g) and iodomethane (0.09 mL) were added. After stirring for 24 hours, the reaction was partitioned between water (30 mL) and EtOAc (30 mL), the layers separated, and the organic layer washed with brine, dried ($Na_2SO_4$) and concentrated. The crude reaction purified over silica gel (gradient of EtOAc in heptane) to provide the title compound (0.14 g) as a clear oil: 1H NMR (DMSO-d6) δ 7.99 (d, 1H); 7.74 (d, 1H), 7.40 (ddd, 1H), 7.30 (ddd, 1H), 6.95 (d, 1H), 6.67 (d, 1H), 3.83 (s, 3H), 2.78 (s, 6H); MS expected 202 ($C_{13}H_{16}NO$, M+1), found 202.

Example 32.
3-hydroxy-1-(dimethylamino)naphthalene

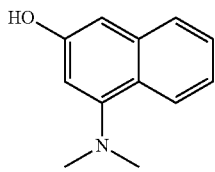

The title compound was synthesized in a similar manner as 11-hydroxy-2,3,5,6,7,8-hexahydro-1H-azepino[3,2,1-ij]quinolone starting from 3-methoxy-1-(dimethylamino)naphthalene: 1H NMR (DMSO-d6) δ 9.53 (s, 1H), 7.95 (d, 1H); 7.60 (d, 1H), 7.32 (ddd, 1H), 7.21 (ddd, 1H), 6.75 (d, 1H), 6.64 (d, 1H), 2.77 (s, 6H).

Example 33. Bis(piperidineazepino)-6-((2-(2-(2-(2-(6-carboxyamido-2-cyanobenzothiazolyl)ethoxy)ethoxy)ethoxy)ethyl)carbamoyl)rhodamine (PBI 5122)

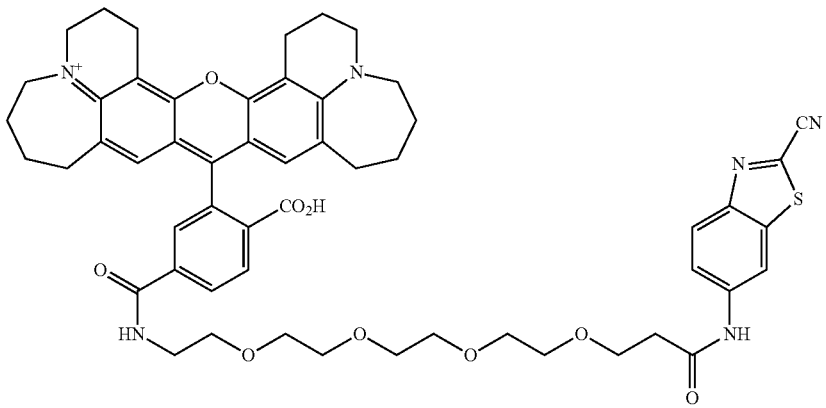 [SMILES: N#Cc1nc2ccc(NC(=O)CCOCCOCCOCCOCCNC(=O)c3ccc(C(=O)O)c(C4=c5cc6c7c(c5Oc5c4cc4c8c5CCCN8CCCC4)CCC[N+]=7CCCC6)c3)cc2s1]

To a solution of t-boc-N-amido-dPEG®4-acid (Quanta BioDesign, 1 g) and N-methylmorpholine (0.3 mL) in THF (25 mL), isobutyl chloroformate (0.36 mL) was added. After stirring for 30 min, 6-amino-2-cyanobenzothiazole (White et. al., J. Am. Chem. Soc. 88, 2015 (1966), 0.48 g) was added, and the reaction stirred overnight. The reaction was then filtered, and the eluent concentrated. The crude reaction purified over silica gel (gradient of MeOH in $CH_2Cl_2$) to provide a clear oil (1.4 g).

The oil from the previous step was dissolved in 15% thioanisole in trifluoroacetic acid (25 mL) at 0° C. The reaction was stirred for 3 hours, diluted with diethyl ether and then concentrated to dryness. The reaction was then filtered, and the eluent concentrated. The crude reaction purified over silica gel (gradient of MeOH in $CH_2Cl_2$) and immediately carried on to the next step.

To a solution of bis(piperidineazepino)-6-carboxyrhodamine (76 mg) and diisopropylethylamine (0.04 mL) in CH2Cl2 (1 mL) was added TSTU (8 mg). After stirring for 15 min, the crude amine from the previous step (62 mg) was added. After stirring another 30 min, the reaction mixture was purified by preparative HPLC (gradient of ACN in 0.1% TFA in $H_2O$) to provide the title compound (6 mg) as a blue solid: MS expected 967 (C54H59N6O9S+, M+1), found 967.

Example 34. General Procedures for Labeling Oligonucleotides with the Dyes of the Present Invention A. Oligonucleotide labeling with N-Hydroxysuccinimidyl Ester Dyes i. 1 µMole Scale A 5'-amino labeled oligonucleotide was synthesized on an ABI 394 DNA synthesizer (1 µmole) using 5' Amino modifier C6 TFA amidite from Glen Research. Deprotection was performed in concentrated ammonium hydroxide overnight at 60° C. to yield a 5'-aminohexyl labeled oligonucleotide. The resulting oligonucleotide was evaporated to dryness, redissolved in 1 ml 0.5 M NaCl (performed for counter-ion exchange) and desalted on NAP-10 size exclusion cartridge (GE Healthcare). After desalting, the oligonucleotide was evaporated to dryness followed by re-dissolution in 200 µl 0.5 M sodium carbonate buffer, pH 9.0. The succinimidyl ester dyes (PBI 4451, 4510, 4574, 4563, 4566 and 4509) were dissolved in DMF at a concentration of 20 µl/mg. 2×20 µl aliquots of the dye/DMF solution were added to the dissolved oligonucleotide at 30 minutes apart. After the second addition of the dye/DMF solution, the reaction was mixed for 1 hour at 20° C. After one hour, it was diluted to 1 ml with water and desalted on a NAP-10 column (GE Healthcare). The NAP-10 eluate was purified by reversed phase HPLC on a Phenomonex Jupiter C18 column using an acetonitrile/0.1M TEAA buffer system. The HPLC purified oligonucleotide was evaporated to dryness redissolved in 0.01M triethylammonium bicarbonate and desalted on a NAP-10 column. After final desalt step, the oligonucleotide was evaporated to dryness and stored at −20° C.

ii. 100 µMole Scale

A 5'-amino labeled oligonucleotide was synthesized on an AKTA OligoPilot (100 µmole) DNA synthesizer using 5' Amino modifier C6 TFA amidite from Glen Research. Deprotection was performed in concentrated ammonium hydroxide overnight at 60° C. to yield a 5'-aminohexyl labeled oligonucleotide. The resulting oligonucleotide was evaporated to dryness, redissolved in 75 ml 2 M NaCl and desalted on a 500 ml G-25 column (GE Healthcare). After desalting, the oligonucleotide was evaporated to dryness followed by re-dissolution in 50 ml 0.5 M sodium carbonate buffer, pH 9.0. The succinimidyl ester dyes (PBI 4451, 4510, 4574, 4563, 4566 and 4509) were dissolved in DMF at a concentration of 20 µl/mg. 2400 µl of the dye/DMF solution was added drop wise to the dissolved oligonucleotide. The reaction was mixed for 1 hour at room temperature. The dye conjugated oligonucleotide was neutralized with sodium acetate, pH 5.5, solution and precipitated from 2× volume of ethanol. The precipitated oligonucleotide was centrifuged at 9000 rpm for 60 minutes, the supernatant decanted to waste, and the resulting solid dissolved in 70 ml water and purified by ion-exchange chromatography. The oligonucleotide was concentrated and desalted using tangential flow ultrafiltration and subsequently evaporated to dryness. It was stored at −20° C.

B. Oligonucleotide Labeling with Phosphoramidites Dyes i. 1 µMole Scale

A 5'-labeled oligonucleotide was synthesized on an ABI 394 DNA synthesizer (1 µmole) using the phosphoramidite dye (PBI 3885) of the present invention dissolved to 0.1M in acetonitrile. Deprotection was performed in t-butylamine/MeOH/water (25/25/50) overnight at 60° C. to yield a 5'-labeled oligonucleotide. The resulting oligonucleotide was evaporated to dryness, redissolved in 0.01 M triethylammonium bicarbonate and purified by reversed phase HPLC on a Phenomonex Jupiter C18 column using an acetonitrile/0.1 M TEAA buffer system. The HPLC purified oligonucleotide was evaporated to dryness, redissolved in 0.01 M triethylammonium bicarbonate and desalted on a NAP-10 column (GE Healthcare). After final desalt step, the oligonucleotide was evaporated to dryness and stored at −20 C.

ii. 100 µMole Scale

A 5'-labeled oligonucleotide was synthesized on an AKTA OligoPilot DNA synthesizer (100 µmole) using the phosphoramidite dye (PBI 3885) of the present invention dissolved to 0.1 M in acetonitrile. Deprotection was performed in t-butylamine/MeOH/water (25/25/50) overnight at 60° C. to yield a 5'-labeled oligonucleotide. The resulting oligonucleotide was evaporated to dryness, redissolved in 0.01M triethylammonium bicarbonate and purified by ion-exchange HPLC. The resulting purified oligonucleotide was concentrated and desalted using tangential flow ultrafiltration and evaporated to dryness. The labeled oligonucleotide was stored at −20° C.

Example 35. PCR and Multiplex PCR Using Oligonucleotides Labeled with the Dyes of the Present Invention To demonstrate the ability to perform a 6-dye multiplex PCR with the dyes of the present invention, multiplex reactions were performed containing primer pairs for 24 STR loci.

For the multiplex reactions, a 5× primer pair master mix for 21 STR loci ("5×21-STR Primer Mix") as outlined in Table 1 and a 5× reaction master mix ("5× Reaction Master Mix") containing reaction buffer and GoTaq® Hot Start DNA polymerase were made. Also, in addition to the 21 STR loci primer pairs, additional primer pairs were prepared as described in Table 2 using dyes of the present invention. These additional primer pairs were made to 150 µM in 1 mM MOPS with 0.1 mM EDTA with final ~pH 7.5 at 25° C.

TABLE 1

| Locus | Dye | Primer Pair Concentration (uM in 5x) |
|---|---|---|
| Amelogenin | 5FAM | 2.88 |
| D3S1358 | 5FAM | 0.88 |
| D1S1656 | 5FAM | 1.42 |
| D6S1043 | 5FAM | 1.32 |
| D13S317 | 5FAM | 1.6 |
| Penta E | 5FAM | 7.88 |
| Penta D | JOE | 3.68 |
| D16S539 | JOE | 2.4 |
| D18S51 | JOE | 1.18 |
| D2S1338 | JOE | 2.04 |
| CSF1PO | JOE | 1.4 |
| TH01 | ET TMR | 1.38 |
| vWA | ET TMR | 1.8 |
| D21S11 | ET TMR | 1.55 |
| D7S820 | ET TMR | 2.4 |
| D5S818 | ET TMR | 2.02 |
| TPOX | ET TMR | 1.89 |
| D8S1179 | ET ROX | 1.7 |
| D12S391 | ET ROX | 3.75 |
| D19S433 | ET ROX | 1.05 |
| FGA | ET ROX | 1.28 |

TABLE 2

| Locus | Dye |
|---|---|
| D22S1045 | 6FAM ET PBI 4510 (624 nm) |
| D2S441 | 6FAM ET PBI 4510 (624 nm) |
| DYS391 | 6FAM ET PBI 4510 (624 nm) |
| D22S1045 | 6FAM ET PBI 4563 (640 nm) |
| D2S441 | 6FAM ET PBI 4563 (640 nm) |
| DYS391 | 6FAM ET PBI 4563 (640 nm) |
| D22S1045 | 6FAM ET PBI 4574 (634 nm) |
| D2S441 | 6FAM ET PBI 4574 (634 nm) |
| DYS391 | 6FAM ET PBI 4574 (634 nm) |

Multiplex reactions were then set up as follows:
A. Multiplex 1 Mix (for 10 Reactions):
5× 21-STR Primer Mix: 50 µl
5× Reaction Master Mix: 50 µl
4510-D22S1045 primer pair (0.6 µM): 1 µl
4510-D2S441 primer pair (0.6 µM): 1 µl
4510-DYS391 primer pair (0.6 µM): 1 µl
Nuclease free water: 137 µl
B. Multiplex 2 Mix (for 10 Reactions):
5× 21-STR Primer Mix: 50 µl
5× Reaction Master Mix: 50 µl
4563-D22S1045 primer pair (0.6 µM): 1 µl
4563-D2S441 primer pair (0.6 µM): 1 µl
4563-DYS391 primer pair (0.6 µM): 1 µl
Nuclease free water: 137 µl
C. Multiplex 3 Mix (for 10 Reactions):
5× 21-STR Primer Mix: 50 µl
5× Reaction Master Mix: 50 µl
4574-D22S1045 primer pair (0.6 µM): 1 µl
4574-D2S441 primer pair (0.6 µM): 1 µl
4574-DYS391 primer pair (0.6 µM): 1 µl
Nuclease free water: 137 µl D. Multiplex 4 Mix (for 10 Reactions):
5× 21-STR Primer Mix: 50 µl
5× Reaction Master Mix: 50 µl
4510-D22S1045 primer pair (2.4 µM): 4 µl
4510-D2S441 primer pair (2.4 µM): 4 µl
4510-DYS391 primer pair (2.4 µM): 4 µl
Nuclease free water: 128 µl
E. Multiplex 5 Mix (for 10 Reactions):
5× 21-STR Primer Mix: 50 µl
5× Reaction Master Mix: 50 µl
4563-D22S1045 primer pair (2.4 µM): 4 µl
4563-D2S441 primer pair (2.4 µM): 4 µl
4563-DYS391 primer pair (2.4 µM): 4 µl
Nuclease free water: 128 µl
F. Multiplex 3 Mix (for 10 Reactions):
5× 21-STR Primer Mix: 50 µl
5× Reaction Master Mix: 50 µl
4574-D22S1045 primer pair (2.4 µM): 4 µl
4574-D2S441 primer pair (2.4 µM): 4 µl
4574-DYS391 primer pair (2.4 µM): 4 µl
Nuclease free water: 128 µl 24 µl of each multiplex mix was then added to a well of a 96-well PCR plate. 1 µl of 1 ng/µL male DNA (2800M Promega Cat. # DD7101 or 9948 Promega Cat. # DD206A) or 0.5 ng/µL male DNA (C274 or QC2; Promega) was added to each well. Various single-source male DNA samples were used to determine variability in balance and bleedthrough/bridging of the dyes with various allele patterns. Reactions were then run on an Applied Biosystems 9700 thermal cycler using the following cycling conditions: 96° C. for 1 minutes; then 30 cycles of 94° C. for 10 seconds, 59° C. for 1 minutes and 72° C. for 30 seconds; 60° C. for 10 minutes; and a 4° C. soak. Reactions were then analyzed on an Applied Biosystems 3500xL Genetic Analyzer (FIGS. 4-8).

This example demonstrates that the dyes of the present invention work very well with respectable signals and very little bleedthrough or bridging in multiplex PCR.

Example 36. Cell Labeling Using the Dyes of the Present Invention

To determine the ability of the dyes of the present invention to be used for labeling in cells, the dyes were conjugated to a HaloTag® ligand (Promega) to monitor activity/movement of the HaloTag® protein or HaloTag® fusion protein. For cell labeling, the ligands #3780, 3781, 3782, 3783, 3905, 3906, 3954, 4356 and 4357 (Table 3) were used. U2OS cells stably expressing HaloTag® protein in the nucleus (HT-NLS) were used to test for the cell permeability of the ligands. In some cases, the efficiency of the removal of unbound ligand was also determined Ligands for which HT-NLS imaging did not show obvious ligand removal issues were further tested in cells stably expressing HaloTag® protein in their cytoplasm using a p65-HaloTag® fusion (p65-HT) and U2OS cells not expressing HaloTag® protein. The U2OS p65-HT stable cells were used to establish the imaging parameters for a medium to low expressing fusion protein. These same parameters were then used to assess removal of unbound ligand in U2OS cells not expressing HaloTag. All ligands were diluted in DMSO to 10 mM prior to use with cells.

TABLE 3
| Ligand Number | Ligand Structure | Dye Number |
|---|---|---|
| 3780 | 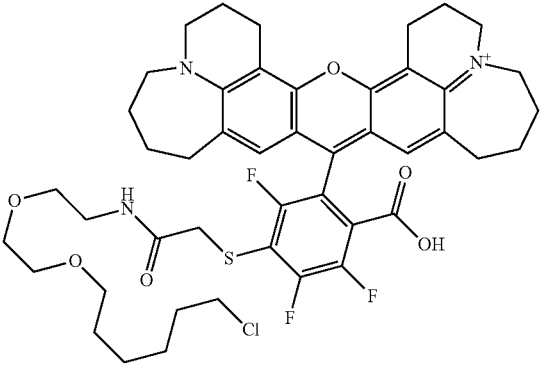 [SMILES: O=C(CSc1c(F)c(F)c(C(=O)O)c(C2=c3cc4c5c(c3Oc3c2cc2c6c3CCCN6CCCC2)CCC[N+]=5CCCC4)c1F)NCCOCCOCCCCCCCl] | |
| 3781 | 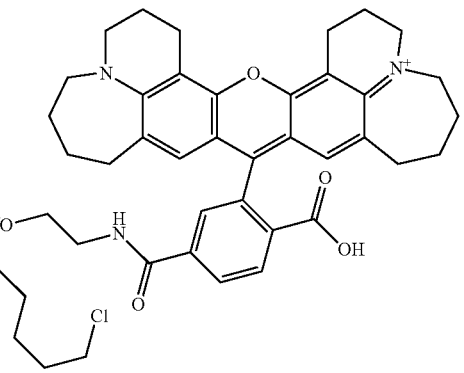 | PBI 3739 |
| 3782 | 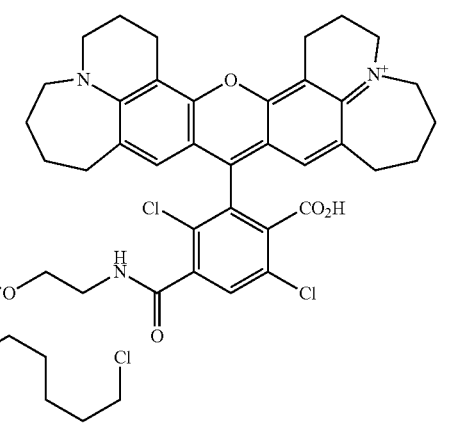 | PBI 3762 |
| 3783 | 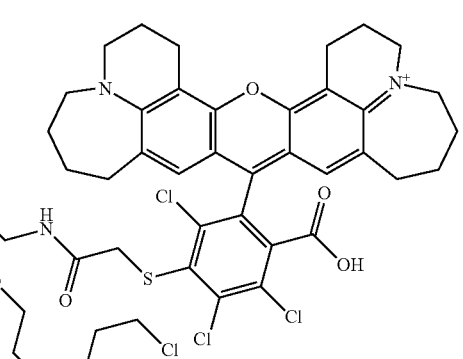 | PBI 3769 |

TABLE 3-continued
| Ligand Number | Ligand Structure | Dye Number |
|---|---|---|
| 3905 | 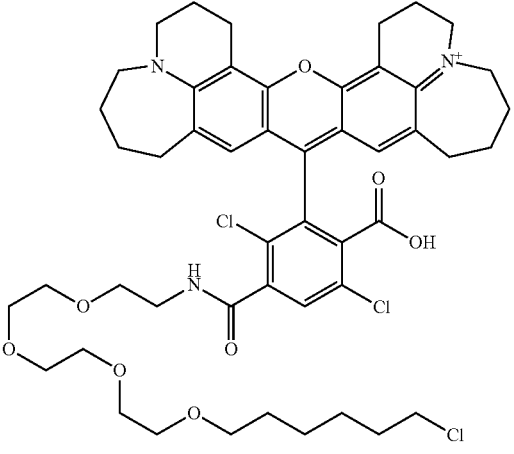 [SMILES: O=C(NCCOCCOCCOCCOCCCCCCCl)c1cc(Cl)c(C(=O)O)c(C2=c3cc4c5c(c3Oc3c2cc2c6c3CCCN6CCCC2)CCC[N+]=5CCCC4)c1Cl] | PBI 3762 |
| 3906 | 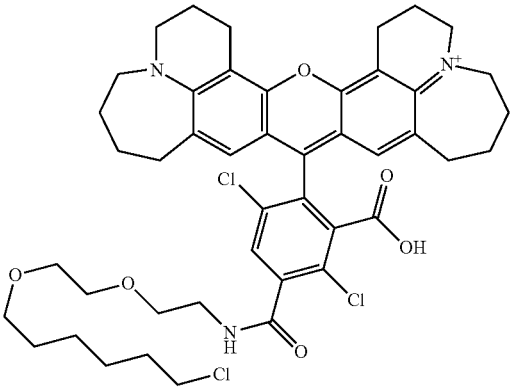 [SMILES: O=C(NCCOCCOCCCCCCCl)c1cc(Cl)c(C2=c3cc4c5c(c3Oc3c2cc2c6c3CCCN6CCCC2)CCC[N+]=5CCCC4)c(C(=O)O)c1Cl] | PBI 3763 |
| 3954 | 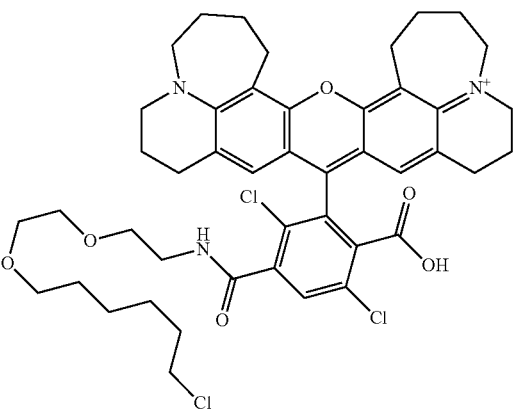 [SMILES: O=C(NCCOCCOCCCCCCCl)c1cc(Cl)c(C(=O)O)c(C2=c3cc4c5c(c3Oc3c2cc2c6c3CCCCN6CCC2)CCCC[N+]=5CCC4)c1Cl] | PBI 3954 |

TABLE 3-continued

| Ligand Number | Ligand Structure | Dye Number |
|---|---|---|
| 4356 | | |
| 4357 | | |

For all imaging experiments, U2OS cells were plated in Lab-Tek II CG (Nunc) chambered coverslips and left overnight at 37° C.+5% $CO_2$ to attach. Cells were exposed to 1 µM ligand by a rapid label protocol. Briefly, cells were exposed to the ligand for 15 minutes in the presence of ATCC-recommended complete media at 37° C.+5% $CO_2$ and 800 µg/ml G418 (Promega). After labeling, cells were rinsed 3 times with complete media and incubated for 30 minutes at 37° C.+5% $CO_2$. The media was then replaced with fresh complete media, and cells transferred to a confocal microscope for imaging.

In some cases, U2OS cells stably expressing HT-NLS were labeled by a no-wash protocol. Briefly, cells were exposed to 100 nM ligand overnight at 37° C.+5% $CO_2$. In these cases, the ligand was added at the time of cell plating. On the following day, the ligand containing media was replaced with fresh complete media, and cells were transferred to a confocal microscope for imaging.

Confocal images were acquired using an Olympus Fluoview FV500 confocal microscope (Olympus, USA) outfitted with a 37° C.+$CO_2$ environmental chamber (Solent Scientific Ltd., UK) and appropriate filter sets. See FIGS. 9-16.

Figures 17A, 17B:
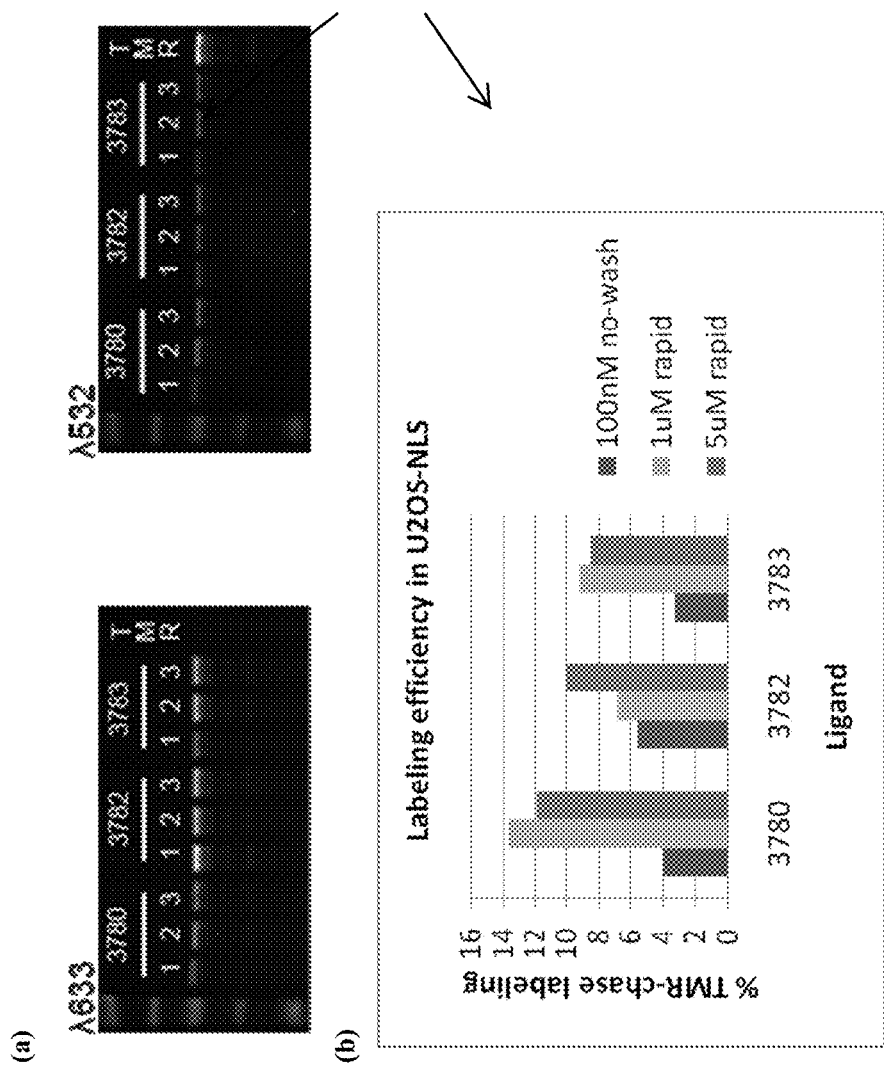
FIGS. 17(a)-17(b) shows the labeling efficiency of ligands 3780, 3782 and 3783 in U2OS cells stably expressing HT-NLS.

In order to quantify labeling efficiency of the ligands, SDS-PAGE analysis was performed. Briefly, cells were plated as above for imaging and were first labeled with 1 µM of ligand for 15 minutes at 37° C.+5% $CO_2$. The ligand-containing media was then replaced with media containing 5 µM HaloTag® TMR ligand (Promega; Cat. No. G8252) and incubated for 15 minutes at 37° C.+5% $CO_2$. Cells were then rinsed 3 times and washed for 30 minutes at 37° C.+5% $CO_2$. The cells were then rinsed once with 1×PBS, collected in 1× SDS gel loading buffer (4× buffer (0.24M Tris, 2% SDS, 50.4% Glycerol, 0.4M DTT, 3 mM Bromophenol Blue and Hydrochloric Acid to pH6.8) diluted in water), placed at 95° C. for 5 minutes and loaded on a 4-20% Tris-Glycine precast gel (Invitrogen). The gel was then scanned using a Typhoon 9410 (Amersham Biosciences) (FIG. 17).

To determine cell viability after labeling, cells were plated in white tissue culture treated Costar 96-well plates (Fisher Scientific). Both the CellTiter-Glo® Luminescent Cell Viability Assay and HaloTag® protein arrays were performed as per manufacturer protocols (Promega). Briefly, for the CellTiter-Glo assay, 100 µl of the CellTiter-Glo reagent was added to the 100 µl of media containing cells. The contents were mixed on an orbital shaker for 2 minutes and incubated at room temperature for 10 minutes. Luminescence was measured using a GloMax® Multi Detection System (Promega). The luminescent signal generated is directly proportional to the amount of ATP present in the sample which is directly proportional to the number of cells present in the culture.

Figure 18:
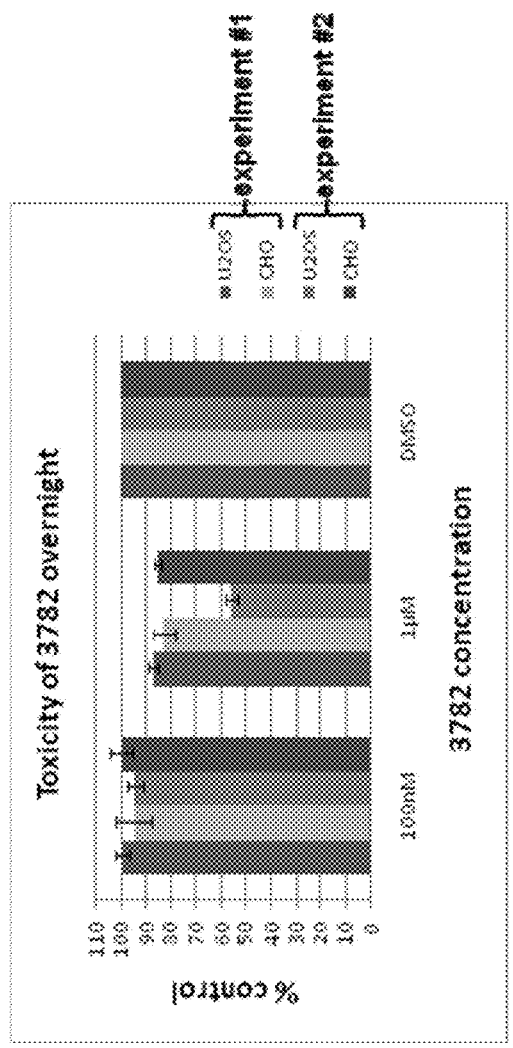
FIG. 18 shows viability of U2OS and CHO cells in the presence of ligand 3782. Graph shows results of CellTiter-Glo® Luminescent Cell Viability Assay after 24 hour incubation with ligand 3782 or DMSO carrier (control). Each bar represents n=6 wells, ±SEM.
Figure 19:
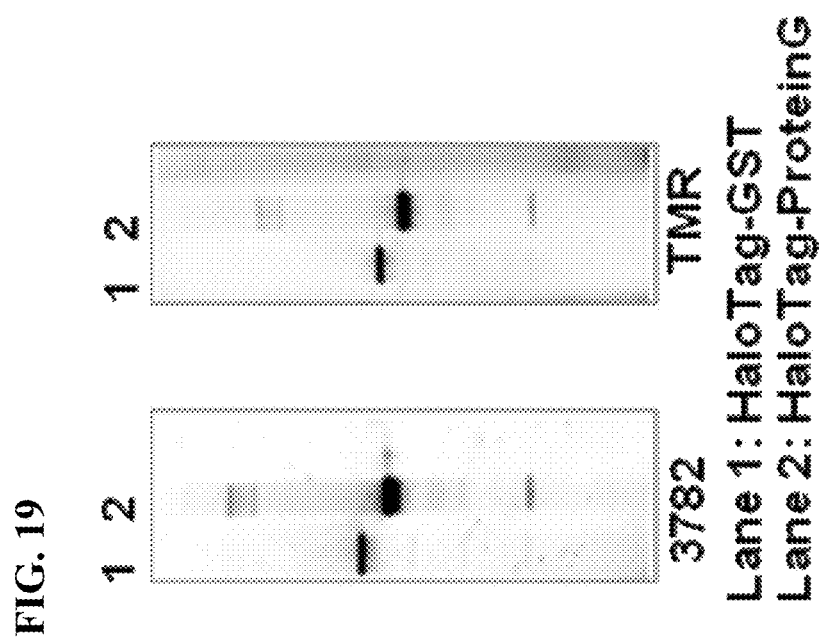
FIG. 19 shows the performance of ligand 3782 in a gel-based analysis as an alternative to the HaloTag® TMR ligand.

In order to assess the use of ligand 3782 for gel based analysis, its performance was compared to that of the HaloTag® TMR Ligand (Promega Cat. No. G8252). To do this, the standard Promega protocol for labeling proteins expressed in a cell-free system was used. Briefly, each ligand was diluted to 10 μM in 1×PBS, and 1 μl of each ligand added to 2 μl each of HaloTag®-GST Standard Protein (Promega) or HaloTag®-protein G purified from *E. coli*. 7 μl of 1×PBS was then added to each labeling reaction for a total volume of 10 μl, and reactions were incubated for 30 minutes at room temperature protected from light. 5 μl of each labeling reaction was then added to 5 μl of 2×SDS gel loading buffer and heated to 70° C. for 2 minutes. The samples were then loaded and run on a SDS-polyacrylamide gel and visualized using a fluorescent scanner as described above (FIGS. 18 and 19).

Example 37. Synthesis of 5-((2-(4-(3-tert-Butyl-5-(3-phenylureido)-1H-pyrazol-1-yl)benzylamino)-2-oxoethyl)carbamoyl)-2-bis(piperidineazepino)rhodamine (PBI-4838)

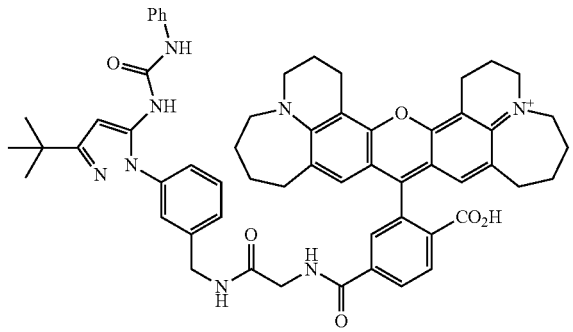

PBI-4838

The title compound was synthesized using bis(piperidineazepino)-6-carboxyrhodamine and 1-(1-(4-((2-aminoacetamido)methyl)phenyl)-3-tert-butyl-1H-pyrazol-5-yl)-3-phenylurea (Tecle et al. 2009, Chem. Biol. Drug Des., 74:547-559) in a manner similar to PBI-3781 (Example 21): MS expected 815 ($C_{58}H_{61}N_8O_6^+$, M+), found 815.

Example 38. Bioluminescence Resonance Energy Transfer (BRET) Using PBI 4828

Figure 20:
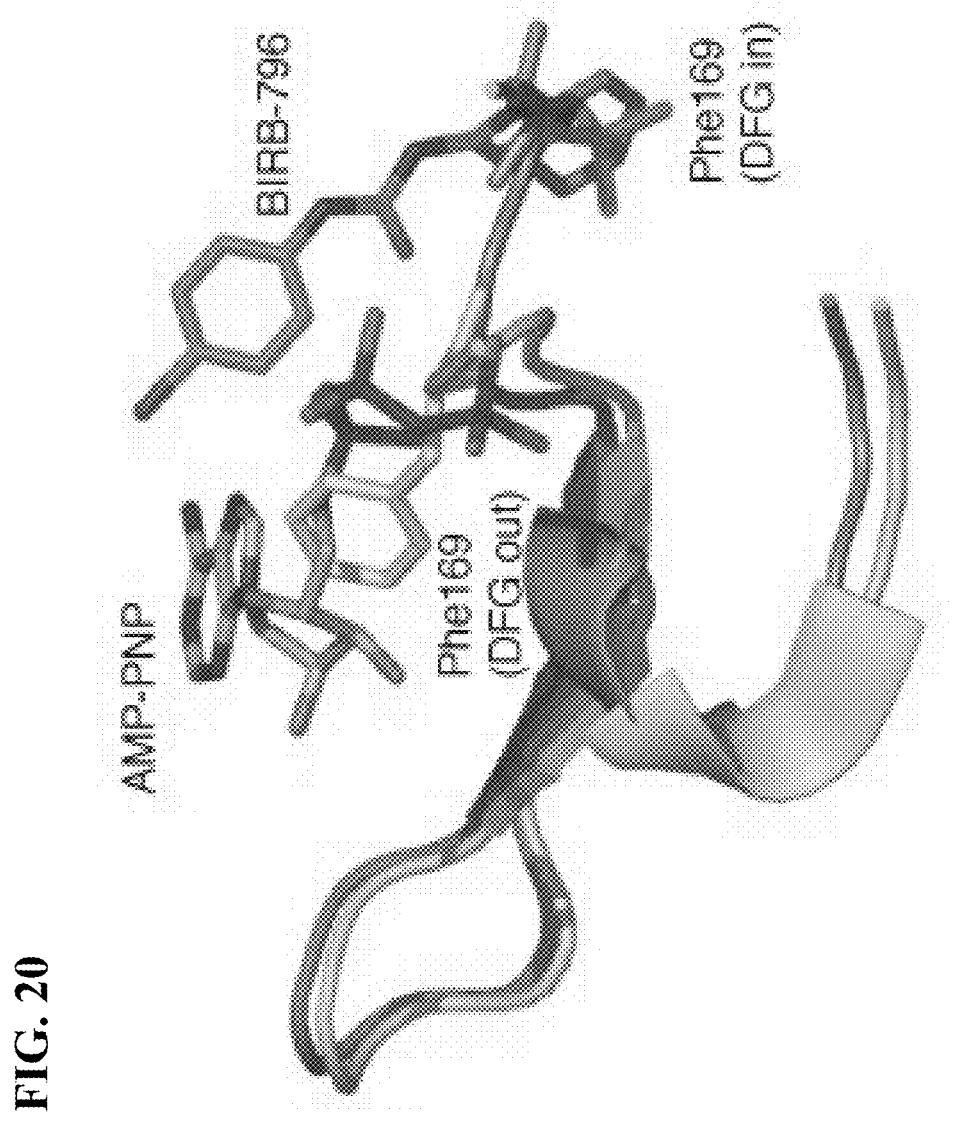
FIG. 20 shows a schematic representation of a p38alpha kinase fluorescent tracer PBI 4838 binding to an inactive p38alpha kinase.

To demonstrate the ability of the dyes of the present invention to be used in BRET applications, a fluorescent dye tracer comprising a dye of the present invention, PBI 4838, was generated to monitor binding of a known drug to a kinase target in living cells. In this example, a p38alpha kinase inhibitor, BIRB796, was used as a scaffold to generate a fluorescent tracer for inactive p38alpha kinase comprising PBI 4838 (Tecle et al. 2009. Chem Biol Drug Des: 74: 547-559; FIG. 20). The tracer was then applied to living or lysed cells expressing a NanoLuc luciferase-p38alpha kinase fusion protein. Upon addition of a furimazine substrate for the NanoLuc luciferase, dose-dependent BRET was then measured in both living and lysed cells.

HEK293 cells (20,000 cells per well in 96-well format) were transiently transfected (Fugene HD, Promega Corporation) with pF5 plasmid DNA (Promega Corporation) encoding a NanoLuc® luciferase-p38alpha kinase fusion protein. As a negative control, some cells were transfected with a pF5 plasmids DNA encoding a NanoLuc luciferase-PKC alpha fusion protein. On the second day post transfection, the cell medium was replaced with serum-free Opti-MEM (Life Technologies) with or without 50 ug/ml digitonin.

For tracer saturation experiments, cells were treated with serially diluted PBI 4838 in the presence or absence of a molar excess of BIRB796 (10 uM final).

For BIRB796 competition experiments, serially-diluted BIRB796 was applied to cells in the presence or absence of 0.5 uM PBI 4838 (final concentration).

Figure 21A:
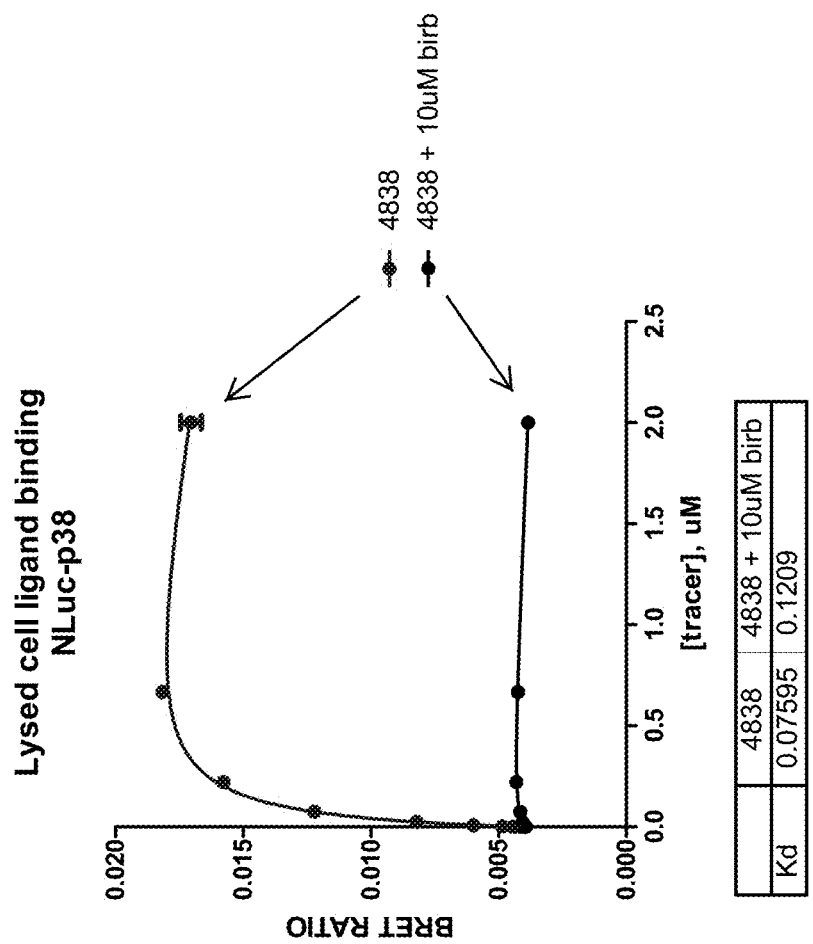
FIGS. 21A-21B shows a titration of the dye tracer PBI 4838 with cells expressing a NanoLuc-p38 fusion protein monitored using BRET. In addition, the figure shows that the interaction of the tracer and NanoLuc-p38 fusion can be inhibited by BIRB796. Binding was monitored using BRET in lysed cells FIG. 21A and live cells FIG. 21B.
Figure 21B:
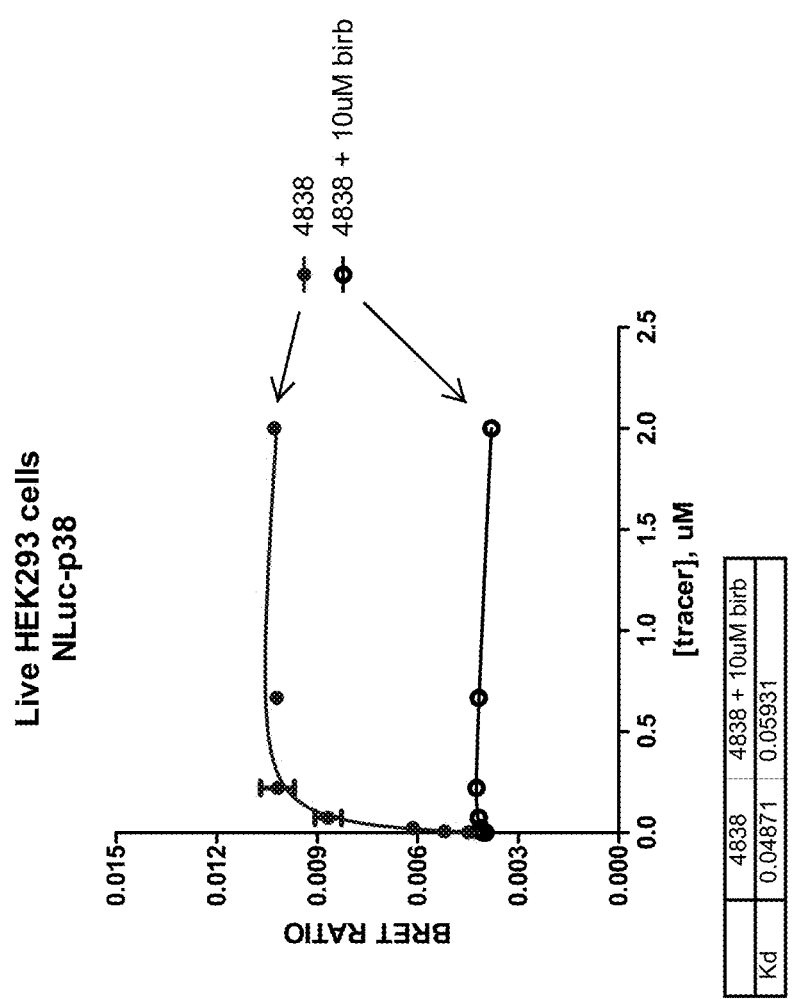
Figure 22A:
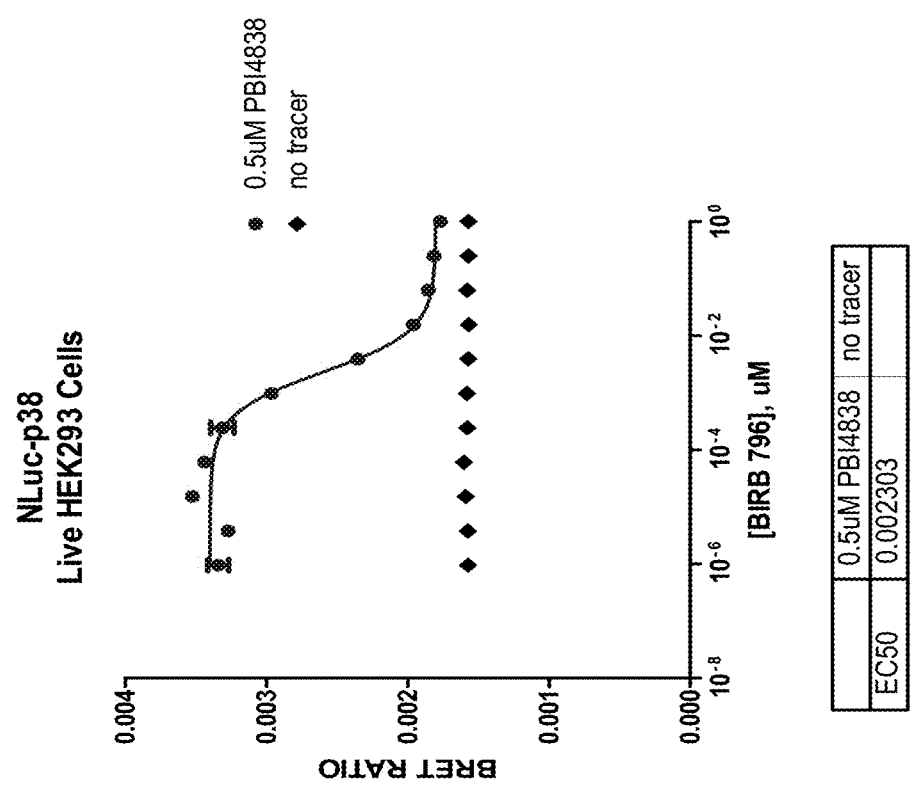
FIGS. 22A-22B shows monitoring of the binding of a known drug, BIRB796, to a kinase target, p38, in living cells using a fluorescent dye tracer PBI 4838. Binding was monitored using BRET and the EC50 value determined for p38 FIG. 21A and PKCa (negative control) FIG. 21B.
Figure 22B:
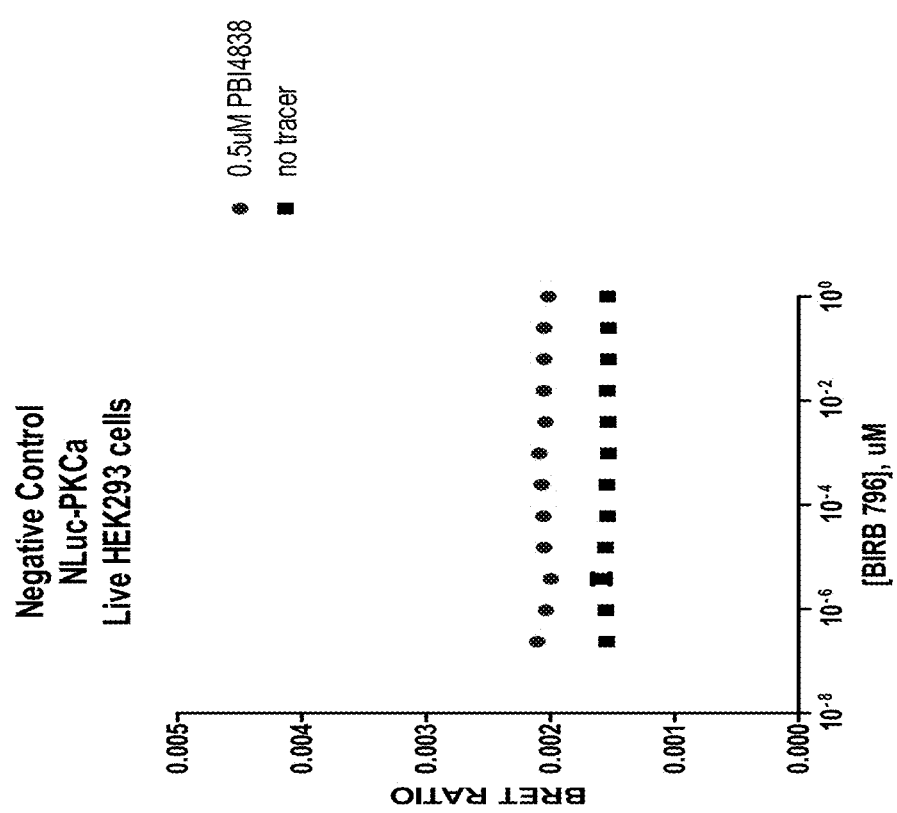

Cells were then allowed to equilibrate with tracer and BIRB796 for 2 hours at 37° C. A furimazine substrate (PBI 3939), a substrate for the NanoLuc luciferase, then was added to cells to a final concentration of 20 uM. BRET ratios were recorded using a Varioskan luminometer at the following wavelengths: 630 nm (acceptor)/450 nm (donor). Acceptor/donor values were used to determine BRET ratio (FIGS. 21 and 22).

The data demonstrates that the dyes of the present invention can be used in BRET applications. In the tracer saturation experiments, live or permeablized cells expressing NanoLuc-p38alpha were incubated with serially diluted PBI 4838 resulting in dose-dependent increase in BRET. The results indicate binding of PBI 4838 to NanoLuc fusion proteins in living cells. In the presence of a vast molar excess of unlabeled BIRB796, the BRET signal was inhibited completely, indicating that nearly the entire BRET signal between NanoLuc-p38alpha and PBI 4838 is specific. For the BIRB796 competition experiments, the data shows the ability to competitively displace a fixed concentration of PBI-4838 in a dose-dependent manner with unlabeled BIRB796. The control experiments further support the specificity of the specific BRET signal between PBI 4838 and NanoLuc p38alpha. This demonstrates the use of cells expressing NanoLuc fused to an irrelevant kinase. In the control experiments, cells expressing NanoLuc-PKCalpha show only a trace amount of BRET signal in the presence of PBI 4838, which is not affected by unlabeled BIRB796.

Example 39. Bioluminescence Resonance Energy Transfer (BRET) Using PBI 3781

To demonstrate the ability of the dyes of the present invention to be used in BRET applications, a fluorescent dye of the present invention was conjugated to a chloroalkane as in Example 21. The dye-chloroalkane conjugate PBI 3781 covalently binds to a HaloTag® protein or a HaloTag® fusion protein allowing detection and/or measurement of the HaloTag or HaloTag® fusion protein. PBI 3781 was used in combination with HaloTag® and NanoLuc fusion proteins to measure protein-protein interactions in living cells via BRET.

Figures 23A, 23B:
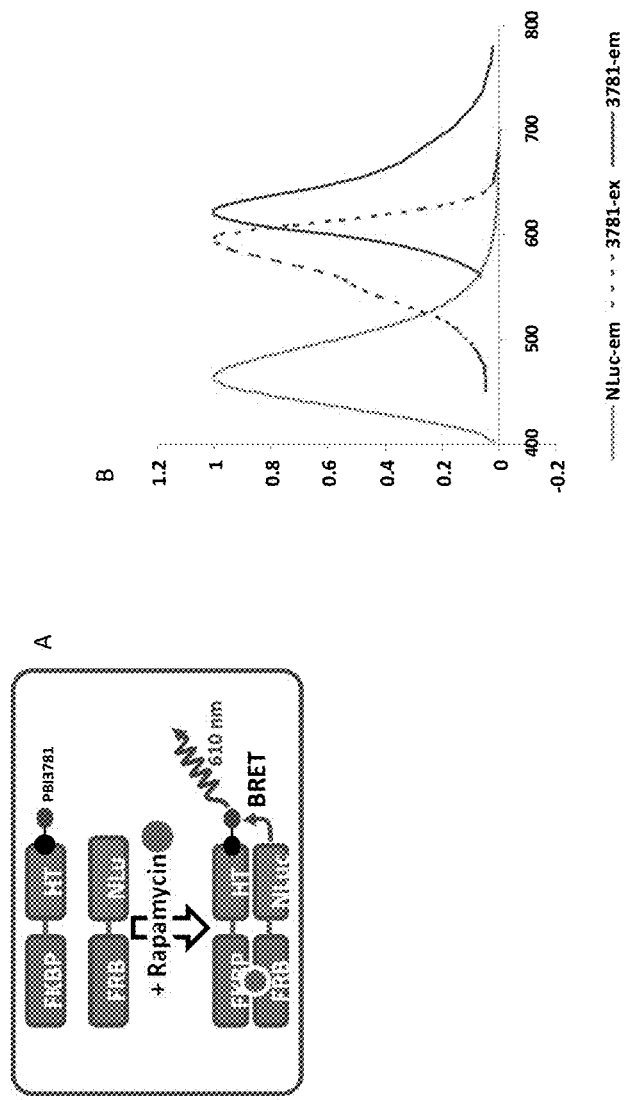
FIGS. 23A-23B shows a rapamycin-dependent increase of BRET occurring between a NanoLuc-Frb fusion (donor) and a HaloTag-FKBP12 fusion bound to PBI 3781, a dye conjugated HaloTag® ligand FIG. 23A.

In this example, the rapamycin-mediated interaction between a NanoLuc luciferase-FK506 binding domain of mTOR (Frb) fusion and a HaloTag-FKBP12 fusion (FK506 binding protein) was used to demonstrate an inducible protein-protein interaction. The interaction was measured as a rapamycin-dependent increase of BRET occurring between the NanoLuc-FRB fusion (donor) and HaloTag-FKBP12 fusion bound to PBI 3781 (acceptor) (FIG. 23A).

HeLa cells were co-transfected with pF5-based constructs (Promega Corporation) for the expression of Frb-NanoLuc or FRKBP12-HaloTag® fusion proteins using FuGENE® HD Transfection Reagent according to the manufacturer's instructions (Promega Corporation). The cells were then incubated overnight at 37° C., 5% $CO_2$.

One day following transfection, the cells were collected and re-plated into wells of a white, 96-well tissue culture plate at 200,000 cells/well in 100 μL DMEM+10% FBS and incubated for 24 hours at 37° C., 5% $CO_2$.

Figure 24:
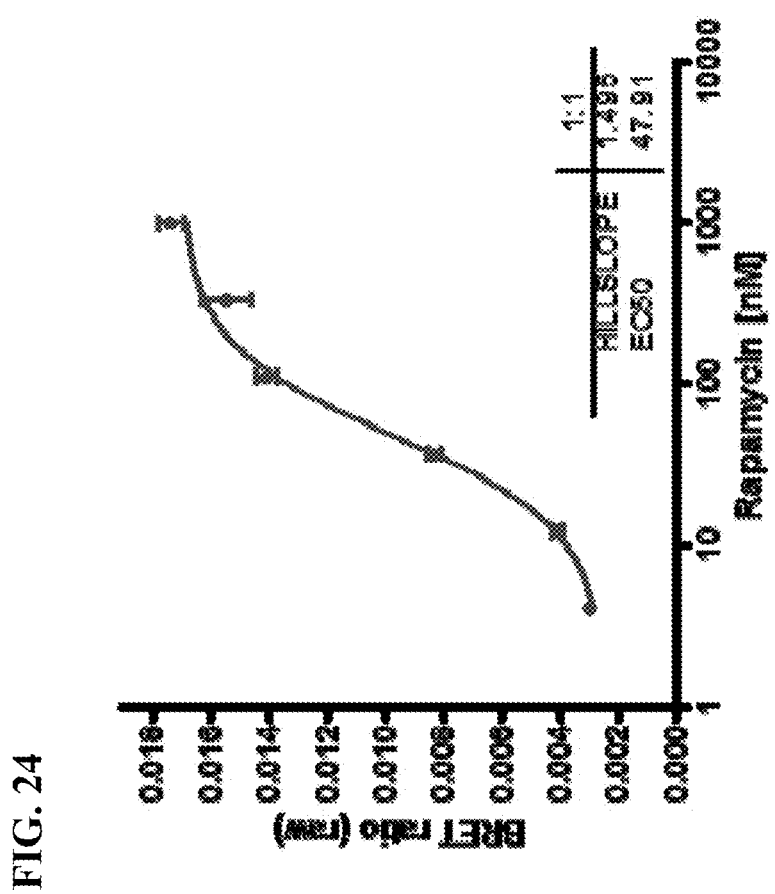
FIG. 24 shows the monitoring of the rapamycin-mediated interaction between a NanoLuc-Frb fusion and HaloTag-FKPf12 fusion using BRET and a dye conjugated HaloTag® ligand (PBI 3781).

Two days after transfection, the growth medium was replaced with phenol red-free DMEM+5% FBS containing 500 nM of PBI 3781, and the cells incubated for 120 minutes 37° C., 5% $CO_2$. The cells were then treated with 50 μL of a serial dilution of rapamycin in phenol-red-free DMEM and incubated for 15 minutes at room temperature. 50 μL, 40 mM furimazine in phenol-red-free DMEM was added, and BRET measured using a Thermo Varioskan plate reader (500 msec integration time; donor channel emission 450/60 bandpass filter; acceptor channel emission 610 nm longpass color glass filter) (FIG. 24).

This experiment demonstrates a concentration-dependent change of absolute BRET signal following the addition of a serial dilution of rapamycin. The experiment also demonstrates that a dye of the present invention can be used to detect other intracellular protein-protein interactions using suitable pairs of NanoLuc and HaloTag® fusion proteins in combination with dye-chloroalkane HaloTag® ligand, e.g., PBI 3781.

Example 40. Prophetic Example of Using a Dye-Cyanobenzothiazole Conjugate

The interaction of a ligand, such as epidermal growth factor (EGF) to epidermal growth factor receptor (EGFR), can be measured in whole cell populations. In such an example, a HaloTag-EGF fusion protein, which contains a TEV protease cleavage site between the HaloTag and EGF protein domains in which the last residue of TEV protease cleavage site encodes a cysteine residue, can be used. Upon cleavage with TEV protease, a Cys-EGF protein is generated and may be reacted with a CBT labeled compound such as PBI 5122 (Example 33). The PBI 5122-Cys-EGF can serve as a probe capable of binding to a NanoLuc-EGFR fusion protein expressed in living cells. Upon binding in close proximity, energy transfer (BRET) can occur, leading to increased dye emission. In another configuration, unlabeled EGF, or ligands of similar binding mechanism, may disrupt the PBI 5122-EGF: NanoLuc-EGFR complex, leading to a decrease in energy transfer. The compatibility of these labeling chemistries and energy transfer methods could allow for the quantification of ligand binding events from ligands and receptors generated in whole cells.

The invention claimed is:

1. A method to detect a selected molecule in a sample, comprising:
a) contacting a sample suspected of containing the selected molecule with a composition comprising a dye conjugate according to formula (IIIa), (IIIb) or (IIIc) so as to yield a mixture:

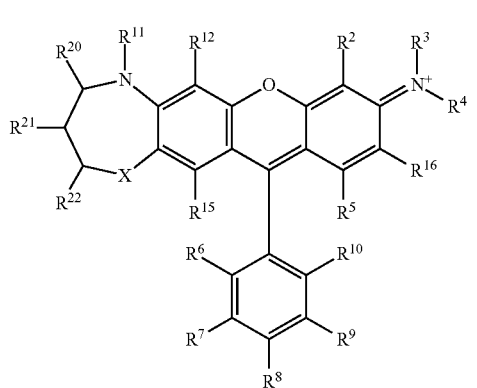

(IIIa)

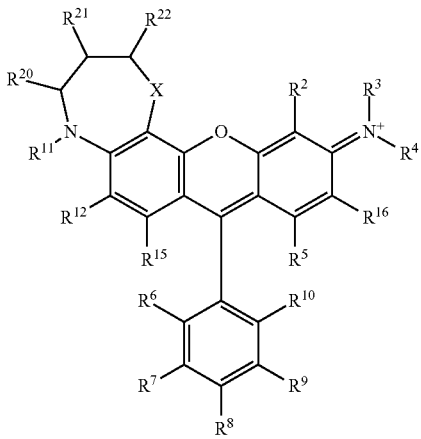

(IIIb)

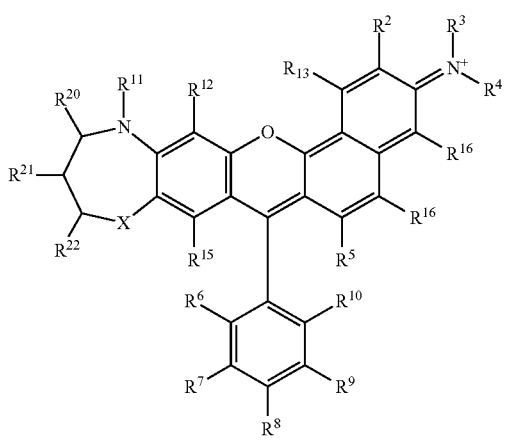

(IIIc)

wherein
$R^{11}$ is independently H or $C_{1-4}$ alkyl or L-$C_s$;
L is a covalent linkage that is linear or branched, cyclic or heterocyclic saturated or unsaturated, having 1-16 non hydrogen atoms such that the linkage contains any combination of ester, acid, amine, amide, alcohol, ether, thioether or halide groups or single, double, triple or aromatic carbon-carbon bond;
$C_s$ is a conjugated substance selected from the group consisting of solid supports, resin particles, beads, assay plates, proteins, nucleotides, polynucleotides, enzyme substrates, nanobodies, polypeptides, amino acids, lipids, carbohydrates, haptens, drugs, ion-complexing agents, microparticles, polymers, cells, viruses, fluorophores, chloroalkanes, and cyanobenzothiazoles;
$R^2$ and $R^{16}$ can be independently H, alkyl, aryl, heteroaryl, $CO_2H$, $SO_3H$, L-$CO_2H$, L-$SO_3H$, or L-$C_s$;
$R^3$ and $R^4$ are H, alkyl, L-$C_s$, L-$CO_2H$, L-$SO_3H$ or together form a carbocyclic, aryl, heteroaryl, or heterocyclic ring; alternatively, $R^2$ and $R^3$ and independently $R^4$ and $R^{16}$ together form a carbocyclic, heterocyclic, aryl or heteroaryl ring;
$R^5$, $R^{12}$, $R^{13}$, $R^{14}$ and $R^{15}$ are independently H, alkyl, aryl, heteroaryl, $CO_2H$, $SO_3H$, L-$CO_2H$, L-$SO_3H$, or L-$C_s$;
$R^{20}$, $R^{21}$, $R^{22}$ and $R^{23}$ are independently H or $C_{1-6}$ alkyl or one or more of $R^{20}$ and $R^{21}$, $R^{21}$ and $R^{22}$, $R^{22}$ and $R^{23}$, together form an aryl, heteroaryl, carbocyclic or heterocyclic ring;
alternatively $R^{11}$ and $R^{12}$ together form a carbocyclic, heterocyclic, aryl or heteroaryl ring;

$R^{6-10}$ are independently H, F, Cl, Br, I, OH, alkyl, aryl, heteroaryl, $CO_2H$, $SO_3H$, $L-CO_2H$, $L-SO_3H$, or $L-C_s$;

X is $CHR^{23}$, O, S or $NR^{30}$; and $R^{30}$ is H, C1-4 alkyl or $—C(O)C1-4$ alkyl; and b) detecting the presence or amount of the dye conjugate in the mixture, thereby detecting the selected molecule in the sample.

2. The method of claim 1, wherein at least one of $R^{2-16}$ is $-L-C_s$.

3. The method of claim 1, wherein $C_s$ is a polynucleotide.

4. A method of detecting the presence of a nucleic acid polymer in a sample comprising:

a) contacting a sample suspected of containing a nucleic acid polymer with a composition comprising a dye conjugate according to formula (IIIa), (IIIb) or (IIIc) so as to yield a mixture:

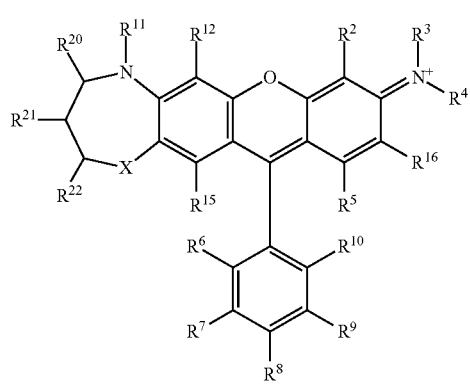

(IIIa)

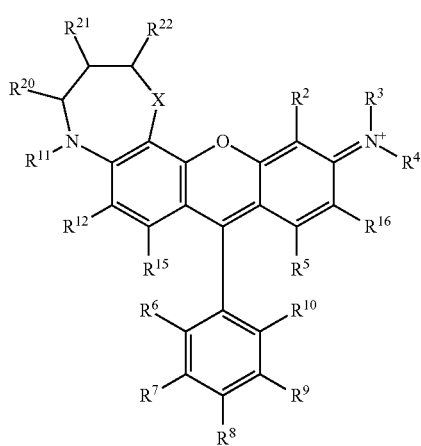

(IIIb)

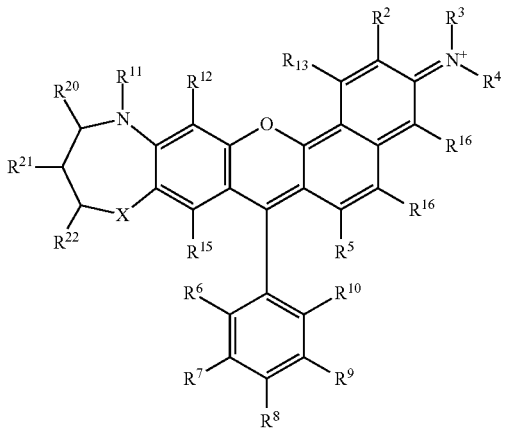

(IIIc)

wherein $R^{11}$ is independently H, $C_{1-4}$ alkyl, or $L-C_s$;

L is a covalent linkage that is linear or branched, cyclic or heterocyclic saturated or unsaturated, having 1-16 non hydrogen atoms such that the linkage contains any combination of ester, acid, amine, amide, alcohol, ether, thioether or halide groups or single, double, triple or aromatic carbon-carbon bond;

$C_s$ is an oligonucleotide;

$R^2$ and $R^{16}$ can be independently H, alkyl, aryl, heteroaryl, $CO_2H$, $SO_3H$, $L-CO_2H$, $L-SO_3H$, or $L-C_s$;

$R^3$ and $R^4$ are H, alkyl, $L-C_s$, $L-CO_2H$, $L-SO_3H$ or together form a carbocyclic, aryl, heteroaryl, or heterocyclic ring;

alternatively, $R^2$ and $R^3$ and independently $R^4$ and $R^{16}$ together form a carbocyclic, heterocyclic, aryl or heteroaryl ring;

$R^5$, $R^{12}$, $R^{13}$, $R^{14}$ and $R^{15}$ are independently H, alkyl, aryl, heteroaryl, $CO_2H$, $SO_3H$, $L-CO_2H$, $L-SO_3H$, or $L-C_s$;

$R^{20}$, $R^{21}$, $R^{22}$ and $R^{23}$ are independently H or $C_{1-6}$ alkyl or one or more of $R^{20}$ and $R^{21}$, $R^{21}$ and $R^{22}$, $R^{22}$ and $R^{23}$, together form an aryl, heteroaryl, carbocyclic or heterocyclic ring;

alternatively, $R^{11}$ and $R^{12}$ together form a carbocyclic, heterocyclic, aryl or heteroaryl ring;

$R^{6-10}$ are independently H, F, Cl, Br, I, OH, alkyl, aryl, heteroaryl, $CO_2H$, $SO_3H$, $L-CO_2H$, $L-SO_3H$, or $L-C_s$;

X is $CHR^{23}$, O, S or $NR^{30}$; and $R^{30}$ is H, $C_{1-4}$ alkyl or $—C(O)C_{1-4}$ alkyl; and b) detecting the presence or amount of the dye conjugate in the mixture, thereby detecting the presence of the nucleic acid polymer in the sample.

5. The method of claim 4, wherein more than one nucleic acid polymer in a sample is detected in a single reaction.

6. The method of claim 5, wherein the more than one nucleic acid polymer is detected by capillary electrophoresis.

7. A method of labeling a biomolecule comprising:

a) contacting a sample suspected of containing the biomolecule with a composition comprising a dye conjugate according to formula (IIIa), (IIIb) or (IIIc) so as to yield a mixture:

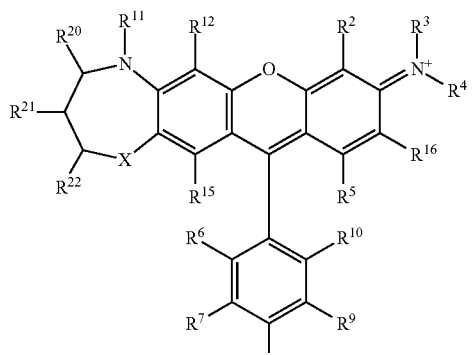
(IIIa)

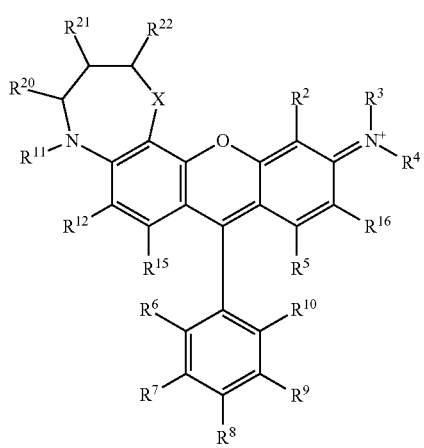
(IIIb)

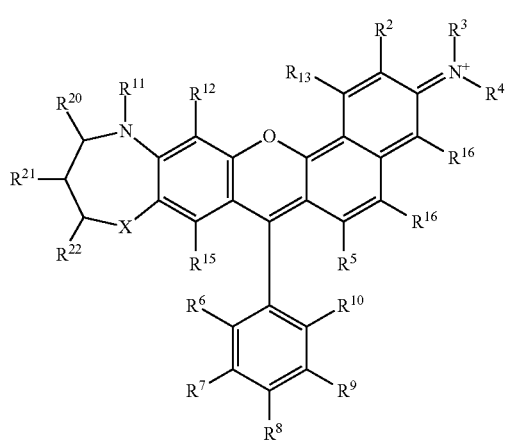
(IIIc)

wherein
$R^{11}$ is independently H or $C_{1-4}$ alkyl, or L-$C_s$;
L is a covalent linkage that is linear or branched, cyclic or heterocyclic saturated or unsaturated, having 1-16 non hydrogen atoms such that the linkage contains any combination of ester, acid, amine, amide, alcohol, ether, thioether or halide groups or single, double, triple or aromatic carbon-carbon bond;
$C_s$ is a conjugated substance selected from the group consisting of solid supports, resin particles, beads, assay plates, proteins, nucleotides, polynucleotides, enzyme substrates, nanobodies, polypeptides, amino acids, lipids, carbohydrates, haptens, drugs, ion-complexing agents, microparticles, polymers, cells, viruses, fluorophores, chloroalkanes, and cyanobenzothiazoles;

$R^2$ and $R^{16}$ can be independently H, alkyl, aryl, heteroaryl, $CO_2H$, $SO_3H$, L-$CO_2H$, L-$SO_3H$, or L-$C_s$;
$R^3$ and $R^4$ are H, alkyl, L-$C_s$, L-$CO_2H$, L-$SO_3H$ or together form a carbocyclic, aryl, heteroaryl, or heterocyclic ring;
alternatively, $R^2$ and $R^3$ and independently $R^4$ and $R^{16}$ together form a carbocyclic, heterocyclic, aryl or heteroaryl ring;
$R^5$, $R^{12}$, $R^{13}$, $R^{14}$ and $R^{15}$ are independently H, alkyl, aryl, heteroaryl, $CO_2H$, $SO_3H$, L-$CO_2H$, L-$SO_3H$, or L-$C_s$;
$R^{20}$, $R^{21}$, $R^{22}$ and $R^{23}$ are independently H or $C_{1-6}$ alkyl or one or more of $R^{20}$ and $R^{21}$, $R^{21}$ and $R^{22}$, $R^{22}$ and $R^{23}$, together form an aryl, heteroaryl, carbocyclic or heterocyclic ring;
alternatively $R^{11}$ and $R^{12}$ together form a carbocyclic, heterocyclic, aryl or heteroaryl ring;
$R^{6-10}$ are independently H, F, Cl, Br, I, OH, alkyl, aryl, heteroaryl, $CO_2H$, $SO_3H$, L-$CO_2H$, L-$SO_3H$, or L-$C_s$;
X is $CHR^{23}$, O, S or $NR^{30}$; and
$R^{30}$ is H, $C_{1-4}$ alkyl or —$C(O)C_{1-4}$ alkyl;
b) detecting the presence or amount of the dye conjugate, thereby detecting the presence or amount of the labeled biomolecule in the mixture.

8. The method of claim 7, wherein the dye conjugate contains a cyanobenzothiazole.
9. The method of claim 7, wherein the biomolecule is a protein.
10. The method of claim 9, wherein the protein comprises an N-terminal cysteine.
11. The method of claim 10, wherein the protein comprising an N-terminal cysteine is labeled with the dye conjugate comprising a cyanobenzothiazole.
12. The method of claim 4, wherein L is —CO—, —$SCH_2CO$—, or —$SO_2$—.
13. The method of claim 12, wherein L is —$SCH_2CO$— and L is bonded to a nucleotide base in the oligonucleotide to form a group

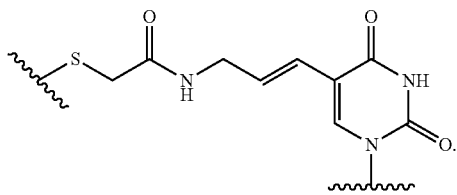 [SMILES: *SCC(=O)NC/C=C/c1cn(*)c(=O)[nH]c1=O]

14. The method of claim 4, wherein L is a group

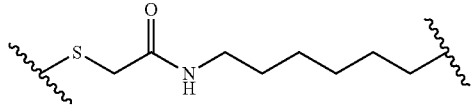 [SMILES: *CCCCCCNC(=O)CS*]

bonded to a 5'-position of the oligonucleotide.
15. The method of claim 4, wherein L is a self-immolative linker selected from the group consisting of

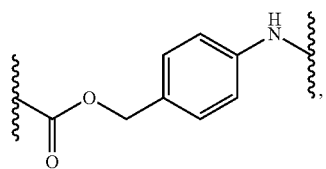

-continued
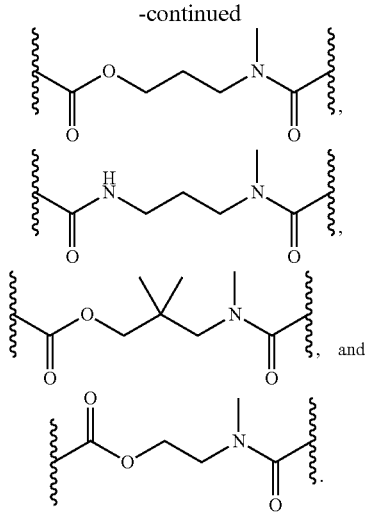
16. The method of claim 1, wherein the protein is an antibody.
17. The method of claim 1, wherein the polypeptide is a polypeptide-based toxin.
18. The method of claim 7, wherein the protein is an antibody.
19. The method of claim 7, wherein the polypeptide is a polypeptide-based toxin.
* * * * *